(12) United States Patent
Huang et al.

(10) Patent No.: US 8,147,865 B2
(45) Date of Patent: Apr. 3, 2012

(54) STEROID-CONTAINING SUSTAINED RELEASE INTRAOCULAR IMPLANTS AND RELATED METHODS

(75) Inventors: Glenn T. Huang, Fremont, CA (US); Thierry Nivaggioli, Atherton, CA (US); Lon T. Spada, Walnut, CA (US); Hiroshi Sugimoto, Huntington Beach, CA (US); Wendy M. Blanda, Tustin, CA (US); James N. Chang, Newport Beach, CA (US); Orest Olejnik, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 1375 days.

(21) Appl. No.: 11/474,149

(22) Filed: Jun. 23, 2006

(65) Prior Publication Data

US 2007/0031472 A1    Feb. 8, 2007

Related U.S. Application Data

(63) Continuation-in-part of application No. 11/118,288, filed on Apr. 29, 2005, which is a continuation-in-part of application No. 10/837,356, filed on Apr. 30, 2004.

(51) Int. Cl.
*A61F 2/14* (2006.01)
(52) U.S. Cl. ........................................... 424/427
(58) Field of Classification Search ..................... None
See application file for complete search history.

(56) References Cited

U.S. PATENT DOCUMENTS

| | | | |
|---|---|---|---|
| 3,396,081 A | 8/1968 | Billek | |
| 3,845,770 A | 11/1974 | Theeuwes et al. | |
| 3,916,899 A | 11/1975 | Theeuwes et al. | |
| 4,008,864 A | 2/1977 | Torphammar et al. | |
| 4,014,335 A | 3/1977 | Arnold | |
| 4,052,505 A | 10/1977 | Higuchi et al. | |
| 4,057,619 A | 11/1977 | Higuchi et al. | |

(Continued)

FOREIGN PATENT DOCUMENTS

CA    1333770    1/1995

(Continued)

OTHER PUBLICATIONS

Antcliff R., et al Marshall J., *The pathogenesis of edema in diabetic maculopathy*, Seminars in Ophthalmology, 1999; 14:223-232.

(Continued)

*Primary Examiner* — Carlos Azpuru
(74) *Attorney, Agent, or Firm* — Louis V. Wollenberger; Joel B. German; Debra D. Condino

(57) ABSTRACT

Biocompatible intraocular implants include a steroid and an auxiliary agent, where the auxiliary agent is present in an amount sufficient to lessen the severity of at least one side effect compared to the use of an otherwise identical implant lacking said auxiliary agent. The steroid and the auxiliary agent may be present on the same intraocular implant or on different implants. The steroid and auxiliary agent may be associated with a biodegradable polymer matrix, such as a matrix of a two biodegradable polymers. Or, the steroid may be associated with a polymeric coating having one or more openings effective to permit the steroid to be released into an external environment. The implants containing the steroid and an auxiliary agent may be placed in an eye to treat one or more ocular conditions while reducing the side effects otherwise accompanying steroid use.

15 Claims, 25 Drawing Sheets

U.S. PATENT DOCUMENTS

| | | |
|---|---|---|
| 4,063,064 A | 12/1977 | Saunders et al. |
| 4,088,864 A | 5/1978 | Theeuwes et al. |
| 4,144,317 A | 3/1979 | Higuchi et al. |
| 4,158,005 A | 6/1979 | Bodor et al. |
| 4,186,184 A | 1/1980 | Zaffaroni |
| 4,190,642 A | 2/1980 | Gale et al. |
| 4,200,098 A | 4/1980 | Ayer et al. |
| 4,281,654 A | 8/1981 | Shell et al. |
| 4,285,987 A | 8/1981 | Ayer et al. |
| 4,303,637 A | 12/1981 | Shell et al. |
| 4,304,765 A | 12/1981 | Shell et al. |
| 4,327,725 A | 5/1982 | Cortese et al. |
| 4,383,992 A | 5/1983 | Lipari |
| 4,396,625 A | 8/1983 | Yamamori et al. |
| 4,425,346 A | 1/1984 | Horlington |
| 4,474,451 A | 10/1984 | Mizokami |
| 4,478,818 A | 10/1984 | Shell et al. |
| 4,494,274 A | 1/1985 | Thurlow |
| 4,521,210 A | 6/1985 | Wong |
| 4,599,353 A | 7/1986 | Bito |
| 4,649,151 A | 3/1987 | Dougherty et al. |
| 4,656,186 A | 4/1987 | Bommer et al. |
| 4,668,506 A | 5/1987 | Bawa |
| 4,675,338 A | 6/1987 | Bommer et al. |
| 4,693,885 A | 9/1987 | Bommer et al. |
| 4,712,500 A | 12/1987 | Montandon |
| 4,727,064 A | 2/1988 | Pitha |
| 4,853,224 A | 8/1989 | Wong |
| 4,863,457 A | 9/1989 | Lee |
| 4,865,846 A | 9/1989 | Kaufman |
| 4,866,168 A | 9/1989 | Dougherty et al. |
| 4,920,104 A | 4/1990 | DeVore et al. |
| 4,932,934 A | 6/1990 | Dougherty et al. |
| 4,935,498 A | 6/1990 | Sessler et al. |
| 4,959,217 A | 9/1990 | Sanders et al. |
| 4,968,715 A | 11/1990 | Dougherty et al. |
| 4,981,871 A | 1/1991 | Abelson |
| 4,997,652 A | 3/1991 | Wong |
| 5,002,962 A | 3/1991 | Pandey et al. |
| 5,017,579 A | 5/1991 | Gubin et al. |
| 5,019,400 A | 5/1991 | Gombtz et al. |
| 5,028,621 A | 7/1991 | Dougherty et al. |
| 5,034,413 A | 7/1991 | Chan et al. |
| 5,075,115 A | 12/1991 | Brine |
| 5,077,049 A | 12/1991 | Dunn et al. |
| 5,089,509 A | 2/1992 | Chandraratna |
| 5,093,349 A | 3/1992 | Pandey et al. |
| 5,100,431 A | 3/1992 | Buster et al. |
| 5,106,615 A | 4/1992 | Dikstein |
| 5,164,188 A | 11/1992 | Wong |
| 5,166,331 A | 11/1992 | Della Valle et al. |
| 5,169,638 A | 12/1992 | Dennis et al. |
| 5,171,741 A | 12/1992 | Dougherty |
| 5,173,504 A | 12/1992 | Dougherty |
| 5,190,966 A | 3/1993 | Dougherty |
| 5,198,460 A | 3/1993 | Pandey et al. |
| 5,209,926 A | 5/1993 | Babcock et al. |
| 5,256,408 A | 10/1993 | Babcock et al. |
| 5,268,178 A | 12/1993 | Calhoun et al. |
| 5,300,114 A | 4/1994 | Gwon et al. |
| 5,314,905 A | 5/1994 | Pandey et al. |
| 5,324,519 A | 6/1994 | Dunn et al. |
| 5,324,718 A | 6/1994 | Loftsson |
| 5,332,582 A | 7/1994 | Babcock et al. |
| 5,356,629 A | 10/1994 | Sander et al. |
| 5,378,475 A | 1/1995 | Smith et al. |
| 5,385,887 A | 1/1995 | Yim et al. |
| 5,438,071 A | 8/1995 | Clauss et al. |
| 5,443,505 A | 8/1995 | Wong et al. |
| 5,459,159 A | 10/1995 | Pandey et al. |
| 5,466,233 A | 11/1995 | Weiner et al. |
| 5,487,897 A | 1/1996 | Polson et al. |
| 5,494,901 A | 2/1996 | Javitt et al. |
| 5,501,856 A | 3/1996 | Ohtori et al. |
| 5,504,074 A | 4/1996 | D'Amato et al. |
| 5,516,522 A | 5/1996 | Peyman et al. |
| 5,552,160 A | 9/1996 | Liversidge et al. |
| 5,565,188 A | 10/1996 | Wong et al. |
| 5,576,311 A | 11/1996 | Guy |
| 5,587,371 A | 12/1996 | Sessler et al. |
| 5,587,479 A | 12/1996 | Makovec et al. |
| 5,597,897 A | 1/1997 | Ron et al. |
| 5,655,832 A | 8/1997 | Pelka et al. |
| 5,656,297 A | 8/1997 | Bernstein et al. |
| 5,688,819 A | 11/1997 | Woodward et al. |
| 5,702,716 A | 12/1997 | Dunn et al. |
| 5,707,643 A | 1/1998 | Ogura |
| 5,717,030 A | 2/1998 | Dunn et al. |
| 5,747,061 A | 5/1998 | Amselem et al. |
| 5,766,242 A | 6/1998 | Wong et al. |
| 5,770,589 A | 6/1998 | Billson et al. |
| 5,776,699 A | 7/1998 | Klein et al. |
| 5,780,044 A | 7/1998 | Yewey et al. |
| 5,798,349 A | 8/1998 | Levy et al. |
| 5,824,072 A | 10/1998 | Wong |
| 5,824,074 A | 10/1998 | Koch |
| 5,869,079 A | 2/1999 | Wong et al. |
| 5,877,207 A | 3/1999 | Klein et al. |
| 5,882,682 A | 3/1999 | Rork et al. |
| 5,906,920 A | 5/1999 | Evans et al. |
| 5,913,884 A | 6/1999 | Trauner et al. |
| 5,919,970 A | 7/1999 | Song et al. |
| 5,922,773 A | 7/1999 | Lipton et al. |
| 5,958,954 A | 9/1999 | Klein et al. |
| 6,051,576 A | 4/2000 | Ashton et al. |
| 6,066,675 A | 5/2000 | Wen et al. |
| 6,074,661 A | 6/2000 | Olejnik et al. |
| 6,107,347 A | 8/2000 | Francese et al. |
| 6,143,314 A | 11/2000 | Chandrashekar et al. |
| 6,217,869 B1 | 4/2001 | Meyer et al. |
| 6,217,895 B1 | 4/2001 | Guo et al. |
| 6,225,303 B1 | 5/2001 | Miller et al. |
| 6,258,319 B1 | 7/2001 | Hearst et al. |
| 6,261,583 B1 | 7/2001 | Dunn et al. |
| 6,270,492 B1 | 8/2001 | Sinofsky |
| 6,270,749 B1 | 8/2001 | Blumenkranz et al. |
| 6,271,216 B1 | 8/2001 | Mello et al. |
| 6,271,220 B1 | 8/2001 | Garst et al. |
| 6,274,614 B1 | 8/2001 | Richter et al. |
| 6,290,713 B1 | 9/2001 | Russell |
| 6,294,361 B1 | 9/2001 | Horowitz et al. |
| 6,306,426 B1 | 10/2001 | Olejnik et al. |
| 6,317,616 B1 | 11/2001 | Glossop |
| 6,319,273 B1 | 11/2001 | Chen et al. |
| 6,331,313 B1 | 12/2001 | Wong et al. |
| 6,357,568 B1 | 3/2002 | Chen |
| 6,369,116 B1 | 4/2002 | Wong et al. |
| 6,387,409 B1 | 5/2002 | Khan et al. |
| 6,395,293 B2 | 5/2002 | Polson et al. |
| 6,395,294 B1 | 5/2002 | Peyman |
| 6,403,649 B1 | 6/2002 | Woodward et al. |
| 6,407,079 B1 | 6/2002 | Müller et al. |
| 6,455,062 B1 | 9/2002 | Olejnik et al. |
| 6,461,631 B1 | 10/2002 | Dunn et al. |
| 6,482,854 B1 | 11/2002 | Lipton et al. |
| 6,497,729 B1 | 12/2002 | Moussy et al. |
| 6,537,568 B2 | 3/2003 | Olejnik et al. |
| 6,548,078 B2 | 4/2003 | Guo et al. |
| 6,565,871 B2 | 5/2003 | Roser et al. |
| 6,565,874 B1 | 5/2003 | Dunn et al. |
| 6,573,280 B2 | 6/2003 | Dreyer |
| 6,595,945 B2 | 7/2003 | Brown |
| 6,699,493 B2 | 3/2004 | Wong |
| 6,713,081 B2 | 3/2004 | Robinson et al. |
| 6,723,353 B2 | 4/2004 | Beck et al. |
| 6,726,918 B1 | 4/2004 | Wong et al. |
| 6,765,012 B2 | 7/2004 | Andrews et al. |
| 2001/0023363 A1 | 9/2001 | Harth et al. |
| 2002/0040015 A1 | 4/2002 | Miller et al. |
| 2002/0094998 A1 | 7/2002 | Burke et al. |
| 2002/0198174 A1 | 12/2002 | Lyons |
| 2003/0018078 A1 | 1/2003 | Woodward et al. |
| 2003/0060763 A1 | 3/2003 | Penfold et al. |
| 2003/0069286 A1 | 4/2003 | Chen et al. |
| 2003/0095995 A1 | 5/2003 | Wong et al. |
| 2003/0171320 A1 | 9/2003 | Guyer |
| 2003/0199478 A1 | 10/2003 | Andrews et al. |

| | | | |
|---|---|---|---|
| 2003/0211123 | A1 | 11/2003 | Shukla et al. |
| 2003/0225152 | A1 | 12/2003 | Andrews et al. |
| 2004/0054374 | A1 | 3/2004 | Weber et al. |
| 2004/0077562 | A1 | 4/2004 | Chandavarkar et al. |
| 2004/0152664 | A1 | 8/2004 | Chang et al. |
| 2005/0181017 | A1 | 8/2005 | Hughes et al. |
| 2005/0244463 | A1 | 11/2005 | Huang |
| 2005/0244468 | A1 | 11/2005 | Huang et al. |
| 2005/0244474 | A1 | 11/2005 | Huang et al. |
| 2005/0250737 | A1 | 11/2005 | Hughes et al. |
| 2006/0009498 | A1 | 1/2006 | Whitcup |
| 2006/0141049 | A1 | 6/2006 | Lyons et al. |
| 2007/0298073 | A1 | 12/2007 | Whitcup et al. |
| 2007/0298074 | A1 | 12/2007 | Robinson et al. |

FOREIGN PATENT DOCUMENTS

| | | |
|---|---|---|
| EP | 0 197 718 A2 | 3/1986 |
| EP | 0 244 178 | 4/1987 |
| EP | 0364417 | 4/1990 |
| EP | 0430539 | 6/1991 |
| EP | 0 488 401 | 6/1992 |
| WO | WO 95/13765 | 5/1995 |
| WO | WO 96/38174 | 5/1996 |
| WO | WO 00/02564 | 1/2000 |
| WO | WO 01/30323 | 5/2001 |
| WO | WO 01/58240 | 8/2001 |
| WO | WO 02/02076 | 1/2002 |
| WO | WO 02/05815 | 1/2002 |
| WO | WO 02/43785 | 6/2002 |
| WO | WO 02/089815 | 11/2002 |
| WO | WO 02/100437 | 12/2002 |
| WO | WO 2004/069280 | 8/2004 |
| WO | WO 2004/087043 | 10/2004 |
| WO | WO 2005/110380 | 11/2005 |

OTHER PUBLICATIONS

Armaly M., *Statistical attributes of the steroid hypertensive response in the clinically normal eye*, Investigative Ophthalmology and Visual Science, 1965; 4:187-197.

Audren, F. et al., *Pharmacokinetic-Pharmacodynamic modeling of the effect of Triamcinolone Acetonide on Central Macular Thickness in Patients with Diabetic Macular Edema*, Investigative Ophthalmology and Visual Science, 45(10); 3435-3441: Oct. 2004.

Aukunuru et al., *In Vitro Delivery of Nano- and Micro-Particles to Human Retinal Pigment Epithelial (ARPE-19) Cells*, Drug Delivery Technologies, 2002; 2(2):50-57.

Becker B., *Intraocular pressure response to topical corticosteroid*, Investigative Ophthalmology and Visual Science, 1965; 4:198-205.

Beer et al., *Intraocular Concentration and Pharmacokinetics of Triamcinolone Acetonide after a Single Intravitreal Injection*, Ophthalmology, Apr. 2003; 110(4):681-686.

Butcher J. et al., *Bilateral cataracts and glaucoma induced by long term use of steroid eye drops* British Medical Journal, 1994; 309-343.

Challa, J.K. et al., *Exudative Macular Degeneration and Intravitreal Triamcinolone: 18month follow up*, Australian and New Zealand Journal of Ophthalmology 1998; 26:277-281.

Chang et al., *Development of a Topical Suspension Containing Three Active Ingredients*, Drug Development and Industrial Pharmacy, 2002; 28(1):29-39.

Crabb et al., *Cloning of the cDNAs encoding the cellular retinaldehyde-binding protein from bovine and human retina and comparison of the protein structures*, Journal of Biological Chemistry, 1988; 263(35):18688-18692.

Danis R. et al., *Intravitreal triamcinolone acetonide in exudative age-related macular degeneration*, Retina, 2000; 20:244-250.

Dea I. et al., *Hyaluronic acid: a novel, double helical molecule*, Science, Feb. 9, 1973; 179(73):560-562.

Dunn et al., *ARPE-19, a human retinal pigment epithelial cell line with differentiated properties*, Experimental Eye Research, 1996; 62:155-169.

Edelman et al., *Corticosteroids inhibit VEGF-induced vascular leakage in a rabbit model of blood-retinal and blood-aqueous barrier breakdown*, Experimental Eye Research, Feb. 2005; 80(2):249-258.

Einmahl et al., *Evaluation of a novel biomaterial in the suprachoroidal space of the rabbit eye*, Investigative Ophthalmology & Visual Science, May 2002; 43(5):1533-1539.

Einmahl et al., *Therapeutic applications of viscous and injectable poly(ortho esters)*, Advanced Drug Investigative Ophthalmology and Visual Science, May 2002; 43(5):1533-1539.

Enyedi, Laura et al., *An Intravitreal Device Providing Sustained Release of Cyclosporine and Dexamethasone*, Current Eye Research, 1995; 549-557.

Hainsworth, Dean P. et al., *Sustained Release Intravitreal Dexamethasone*, Journal of Ocular Pharmacology and Therapeutics, 1996; 12(1):57-63.

Hamel et al., *Molecular cloning and expression of RPE65, a novel retinal pigment epithelium-specific microsomal protein that is post-transcriptionally regulated in vitro*, Journal of Biological Chemistry, 1993; 268(21):15751-15757.

Helliwell P., *Use of an objective measure of articular stiffness to record changes in finger joints after intra-articular injection of corticosteroid*, Annals of the Rheumatic Diseases, 1997; 56:71-73.

Inoue, M. et al., *Vitreous Concentrations of Triamcinolone Acetonide in Human Eyes After Intravitreal or Subtenon Injection*, American Journal of Ophthalmology, 2004; 138(6):1046-8.

Jonas J. et al., *Intravitreal injection of crystalline cortisone as adjunctive treatment of diabetic macular edema*, American Journal of Ophthalmology, 2001; 132:425-427.

Jonas J. et al., *Intravitreal injection of crystalline cortisone as adjunctive treatment of proliferative vitreoretinopathy*, British Journal of Ophthalmology, 2000; 84:1064-1067.

Jonas J. et al., *Intravitreal injection of triamcinolone for diffuse diabetic macular edema*, Archives of Ophthalmology, 2003; 121:57-61.

Klimanskaya et al., *Derivation and comparative assessment of retinal pigment epithelium from human embryonic stem cells using transcriptomics*, Cloning and Stem Cells, 2004; 6(3):217-245.

Kompella et al., *Subconjunctival Nano- and Microparticles Sustain Retinal Delivery of Budesonide, a Corticosteroid Capable of Inhibiting VEGF Expression*, Investigative Ophthalmology and Visual Science, Mar. 2003; 44(3):1192-1201.

Martidis A. et al., *Intravitreal triamcinolone for refractory diabetic macular edema*, Ophthalmology, 2002; 109:920-927.

McCarty D. et al., *Inflammatory reaction after intrasynovial injection of microcrystalline adrenocorticosteroid esters*, Arthritis and Rheumatism, 1964; 7(4):359-367.

McCuen B. et al., *The lack of toxicity of intravitreally administered triamcinolone acetonide*, American Journal of Ophthalmology, 1981; 91:785-788.

McGhee et al., *Locally Administered Ocular Corticosteroids Benefits and Risks*; Drug Safety, 2002; 25(1):33-55.

Morita Y., et al., *Intravitreous delivery of dexamethasone sodium m-sulfobenzoate from poly (DL-lactic acid) implants*, Biological and Pharmaceutical Bulletin, Feb. 1998; 21(2): 188-90.

Nauck, M., et al., *Corticosteroids inhibit the expression of the vascular endothelial growth factor gene in human vascular smooth muscle cells*, European Journal of Pharmacology, 1998; 341:309-315.

Nauck, M., et al., *Induction of vascular endothelial growth factor by platelet-activating factor and platelet-derived growth factor is downregulated by corticosteroids*, American Journal of Respiratory Cell and Molecular Biology, 1997; 16 :398-406.

Nishimura et al., *Isolating Triamcinolone Acetonide Particles for Intravitreal Use with a Porous Membrane Filter*, Retina, The Journal of Retinal and Vitreous Diseases, 2003; 23(6):777-779.

Pe'er J. et al., *Vascular endothelial growth factor by platelet-activating factor and platelet-derived growth factor upregulation in human central retinal vein occlusion*, Ophthalmology, 1998; 105:412-416.

Penfold P. et al., *Exudative macular degeneration and intravitreal triamcinolone: A pilot study*, Australian and New Zealand Journal of Ophthalmology, 1995; 23:293-298.

Rao et al., *Preparation and Evaluation of Ocular Inserts Containing Norfloxacin*, Turkish Journal of Medical Science, 2004; 34:239-246.

Rechtman et al., *Intravitreal triaminolone with photodynamic therapy for subfoveal choroidal neovascularisation in age related macular degeneration*, British Journal of Ophthalmology, 2004; 88:344-347.

Rogojina et al., *Comparing the use of Afymetrix to spotted oligonucleotide microarrays using two retinal pigment epithelium cell lines*, Molecular Vision, 2003; 9:482-496.

Roth D. et al., *Noninfectious endophthalmitis associated with intravitreal triamcinolone injection*, Archives of Ophthalmology, 2003; 121:1279-1282.

Schindler, R.H. et al., *The Clearance of Intravitreal Triamcinolone Acetonide*, American Journal of Ophthalmology, 1982; 93: 415-417.

Scholes, G.N. et al., *Clearance of Triamcinolone From Vitreous*, Archives of Ophthalmololgy, 1985; 103:1567-1569.

Streilein et al., *Ocular immune privilege: therapeutic opportunities from an experiment of nature*, Nature Reviews Immunology, 2003; 3:879-889.

Sutter F. et al., *Pseudo-endophthalmitis after intravitreal injection of triamcinolone*, British Journal of Ophthalmology, 2003; 87;972-974.

Tan, D.T.H. et al., *Randomized Clinical Trial of a New Dexamethasone Delivery System (Surodex) for Treating of Post-Cataract Surgery Inflammation*, Ophthalmology, 1999; 106(2):223-231.

Yeung et al., *Cytotoxicity of Triamcinolone on Cultured Human Retinal Pigment Epithelial Cells: Comparison with Dexamethasone and Hydrocortisone*, Japanese Journal of Ophthalmology, 2004; 48:236-242.

WoldeMussie, "Neuroprotection of retinal ganglion cells in experimental models of glaucoma", Minerva Oftalmol, 42(2):71-8 (2000).

WoldeMussie et al., "Neuroprotective effects of memantine in different retinal injury models in rats", J Glaucoma 11(6):474-480 (2002).

Woodward et al., AGN 192024 (Lumigan®): A Synthetic Prostamide Analog that Lowers Primate Intraocular Pressure by Virtue of Its Inherent Pharmacological Activity, ARVO 2002;(CD-ROM):POS.

Woodward et al., The Pharmacology of Bimatoprost (Lumigan™), Surv Ophthalmol 45 (Suppl 4) S337-S345 (2001).

Zhou, T., et al. "Development of a multiple-drug delivery implant for intraocular management of proliferative vitreoretinopathy", *Journal of Controlled Release* 55: pp. 281-295.

Bito, L. Z. Biological Protection with Prostaglandins Cohen, M. M., ed., Boca Raton, Fla., CRC Press Inc., 1985, pp. 231-252.

Charles, et al., "Use of Bioerodible Polymers Impregnated with Mitomycin in Glaucoma Filtration Surgery in Rabbits," *Ophthalmology*, Apr. 1991, vol. 98, No. 4:503-508.

Jampel, et al, "Glaucoma Filtration Surgery in Monkeys Using 5-Fluorouridine in Polyanhydride Disks," *Arch Ophthalmol.*, Mar. 1990, vol. 108:430-435.

Lee et al., "Glaucoma Filtration Surgery in Rabbits Using Bioerodible Polymers and 5-Fluorouacil", *Ophthalmology*, Dec. 1987, vol. 94, No. 12, pp. 1523-1530.

Lee et al., "The Use of Bioerodible Polymers and 5-Fluorouracil in Glaucoma Filtration Surgery," *Investigative Ophthalmology & Visual Science*, Nov. 1988, vol. 29, No. 11:1692-1697.

Smith et al., "Sustained-Release Subconjunctival 5-Fluorouracil", *Ophthalmic Surgery and Laser*, Sep. 1996, vol. 27, No. 9, pp. 763-767.

ALPHAGAN® P, Product Information.

Company News on Call, "Oculex Announces Positive Clinical Results for Posurdex(R)—The First Biodegradable Ocular Implant in Clinical Trial". Copyright © 1996-2004 PR Newswire Association LLC.

Encyclopedia of Polymer Science and Technology, vol. 3, published by Interscience Publishers, Inc., New York, latest edition.

Handbook of Common Polymers by Scott, J. R. and Roff, W. J., published by CRC Press, Cleveland, Ohio, latest edition.

"Lumigan®: a new ocular hypotensive agent for achieving target intraocular pressures," Acta Ophthalmol Scand, Scientific Abstracts 2002; 80(4):457 (2002).

"Lumigan found effective in early phase 3", Ocul. Surg. News Mar. 1, 2001;19(5):1,35.

*Physician's Desk Reference*, product information on "Alphagan®P", 54 Edition, (2000) pp. 493-494.

*Physician's Desk Reference for Ophthalmic Medicines*, 30 Edition, (2002) p. 285.

Surv Ophthalmol 2002; 47(3): p. 295.

TAZORAC®, Allergan, Product Information.

"Tazarotene", *Drugs Future*, 2003; 28(2):208-209. Annual Update 2003: Dermatologic Drugs.

USP 23; NF 18 (1995) pp. 1790-1798.

Anderson et al., "An Injectable Sustained Release Fertility Control System", *Contraception* vol. 13, pp. 375-384, (1976).

Baker, R., "Controlled Release of Biologically Active Agents", A Wiley-Interscience Publication, p. 73-75 (1987).

Bito, L. Z., *Applied Pharmacology in the Medical Treatment*, Drance, S. M. and Neufeld, A. H. eds., New York, Grune & Stratton, 1984, pp. 477-505.

Bito, L. Z., "Prostaglandins, Old Concepts and News Perspectives" Arch. Ophthalmol. vol. 105, pp. 1036-1039 (1987).

Bodor, N. et al.. "A comparison of intraocular pressure elevating activity of loteprednoletabonate and dexamethasone in rabbits" *Current Eye Research* 11:525-30 (1992).

Brubaker, "Mechanism of Action of Bimatoprost (Lumigan™)", *Surv Ophthalmol* 45 (Suppl 4): S347-S351 (2001).

Busse et al., "Tyrosine kinase inhibitors: rationale, mechanisms of action, and implications for drug resistance", Semin Oncol 28(suppl 16) 47-55 (2001).

Phillips et al., "Penetration of timolol eye drops into human aqueous humour: the first hour", *British Journal of Ophthalmology*, vol. 69, pp. 217-218 (1985).

Chen et al., "Lumigan®: A Novel Drug for Glaucoma Therapy", *Optom In Pract*, 3:95-102 (2002).

Cheng C. K. et al.."Intravitreal sustained-release dexamethasone device in the treatment of experimental uveitis", *Invest. Ophthalmol. Vis. Sci.* 36:442-53 (1995).

Chiang et al., "Pharmacokinetics and Intraocular Pressure Lowering Effect of Timolol Preparations in Rabbit Eyes," *Journal of Ocular Pharmacology and Therapeutics*, vol. 12, No. 4, pp. 471-480, (1996).

Coleman et al., "A 3-Month Randomized Controlled Trial of Bimatoprost (LUMIGAN) versus Combined Timolol and Dorzolamide (Cosopt) in Patients with Glaucoma or Ocular Hypertension", *Ophthalmology* 110(12): 2362-8 (2003).

Conquelet et al, "Successful Photodynamic Therapy Combined with Laser Photocoagulation in Three Eyes with Classic Subfoveal Choroidal Neovascularization Affecting Two Patients with Multifocal Choroiditis: Case Reports", Bull. Soc. Belge Ophtalmol, 283, 69-73, 2002.

Di Colo, "Controlled drug release from implantable matrices based on hydrophobic polymers", *Biomaterials*, vol. 13, No. 12, pp. 850-856 (1992).

David L. Epstein, "Primary Open-Angle Glaucoma", *Chandler and Grant's Glaucoma, Lea & Febiger*, 1986, pp. 129-181.

Fabbro et al., "Protein tyrosine kinase inhibitors: new treatment modalities?", *Current Opinion in Pharmacology*, 2:374-381 (2002).

Fotsis, et. al., "The endogenous oestrogen metabolite 2-methoxyoestradiol inhibits angiogenesis and suppresses tumour growth", *Nature* 1994, 368, 237.

Gilman, A.G., et al., eds. (1990). *Goodman and Gilman's: The Pharmacological Basis of Therapeutics*. 8th Edition, Pergamon Press: New York, pp. 1447-1451.

Goel et al., "Tyrosine Kinase Inhibitors: A Clinical Perspective", *Current Oncology Reports*, 4:9-19 (2002).

Guenther, Lyn C., "Optimizing Treatment with Topical Tazarotene", *Am. J. Clin. Dermotol.*, 2003: 4(3):197-202.

Haluska et al., "Receptor tyrosine kinase inhibitors", Current Opinion in Investigational Drugs, 2(2):280-286 (2001).

Hare et al., "Efficacy and safety of memantine, an NMDA-Type Open-Channel Blocker, for reduction of retinal injury associated with experimental glaucoma in rat and monkey", Surv Ophthalmol 45(Suppl 3): S284-S289 (2001).

Hashizoe, Mototane et. al. "Scleral Plug of BiodegadablePolymers for Controlled Drug Release in the Vitreous", *Arch Ophthalmol.* 1994;112: 1380-1384.

Heller, "Biodegradable Polymers in Controlled Drug Delivery", in: *CRC Critical Reviews in Therapeutic Drug Carrier Systems*, vol. 1, (CRC Press, Boca Raton, FL, 1987), pp. 39-90.

Heller, *Hydrogels in Medicine and Pharmacy*, N. A. Peppes ed., vol. III, (CRC Press, Boca Raton, FL, 1987), pp. 137-149.

Hoyng et al., "Pharmacological Therapy for Glaucoma", Drugs, Mar. 2000, 59(3):411-34.

Hubbard et al., "Protein tyrosine kinase structure and function", Annu. Rev. Biochem., 69:373-98 (2000).

Jackanicz et al., "Polyactic Acid As A Biodegradable Carrier for Contraceptive Steriods" Contraception, vol. 8, No. 3:227-235 (1973).

Kimura, Hideya et. al. "A New Vitreal Drug Delivery System using an Implantable Biodegradable Polymeric Device", *Invest Ophthalmol Vis Sci*. 1994;35 : 2815- 2819.

Kochinke et al., "Biodegradable Drug Delivery System for Uveitis Treatment", *Investigative Ophthalmology & Visual Science*, Feb. 15, vol. 37, No. 3, (1996).

Kwak, H.W. and D'Amico, D. J. "Evaluation of the retinal toxicity and pharmacokinetics of dexamethasone after intravitreal injection", *Arch. Ophthalmol*. 110:259-66 (1992).

Lai et al, "Alpha-2 adrenoceptor agonist protects retinal function after acute retinal ischemic injury in the rat", *Vis Neurosci*, 19:175-185 (2002).

Marks, R., "Topical Tazarotene: Review and Re-Evaluation", *Retinoids*, 2001; 17(3):72-74.

Maurice, D.M. "Micropharmaceutics of the eye", *Ocular Inflammation Ther*. 1:97-102 (1983).

Miller et al., "Degradation Rates of Oral Resorbable Implants (Polylactates and Polyglycolates) : Rate Modification with Changes in PLA/PGA Copolymer Ratios", *J. Biomed. Materials Res*. vol. 11, pp. 711-719 (1977).

Miller et al., "Synthesis and Structure-Activity Profiles of A-Homoestranes, the Estratopones", J. Med. Chem., 40:3836-3841 (1997).

Olsen, T.W. et al. "Human scleral permeability: effects of age, cryotherapy, transscleral diode laser, and surgical thinning", *Invest. Ophthalmol. Vis. Sci*. 36:1893-1903 (1995).

Phillips et al., "Efficacy of 0.1% Tazarotene Cream for the Treatment of Photodamage", *Arch Dermatol*, Nov. 2002, 138(11): 1486-1493.

Pribluda et al., "2-Methoxyestradiol: An endogenous antiangiogenic and antiproliferative drug candidate", *Cancer and Metastasis Reviews*, 19: 173-179 (2000).

Quigley et al., "The mechanism of optic nerve damage in experimental acute intraocular pressure elevation", *Invest. Ophthalmol. Vis. Sci*. 19:505 (1980).

Rao, N.A. et al. (1997). "Intraocular inflammation and uveitis", in: *Basic and Clinical Science Course* (San Francisco: American Academy of Ophthalmology, 1997-1998), Section 9, pp. 57-80, 102-103, 152-156.

Renfro, L. et al. "Ocular effects of topical and systemic steroids", *Dermatologic Clinics* 10:505-12 (1992).

Schuettauf et al., "Effects of anti-glaucoma medications on ganglion cell survival: the DBA/2J mouse model", *Vision Res*., 42(20):2333-7 (2002).

Schumacher et al., "The Physiological Estrogen Metabolite 2-methoxyestradiol reduced tumor growth and induces apoptosis in human solid tumors", *J Cancer Res Clin Oncol*., 127:405-410 (2001).

Schwartz, B. "The response of ocular pressure to corticosteroids", *Ophthalmol. Clin. North Am*. 6:929-89 (1966).

Skalka, H.W. et al. "Effect of corticosteroids on cataract formation", *Arch. Ophthalmol*. 98:1773-7 (1980).

Starr, M. S., "Further Studies on the Effect of Prostaglandin on Intraocular Pressure in the Rabbit", *Exp. Eye Res*., vol. 11, pp. 170-177 (1971).

Siebold et al., *Prodrug* 5, 3 (1989).

Tracy et al., "Factors affecting the degradation rate of poly(lactide-co-glycolide) microspheres in vivo and in vitro", *Biomaterials*, vol. 20, pp. 1057-1062 (1999).

Watson et al., "A Six-month, Randomized, Double-masked Study Comparing Latanoprost with Timolol in Open—angle Glaucoma and Ocular Hypertension", *Ophthalmology* vol. 103:126-137 (1996).

Wheeler, "Experimental studies of agents with potential neuroprotective properties", Acta Ophthalmol Scand, 77(229):27-28 (1999).

Wheeler et al, "Role of Alpha-2 Agonists in Neuroprotection", Surv Ophthalmol, vol. 48 (Suppl 1): S47-S51 (Apr. 2003).

U.S. Appl. No. 10/246,884, filed Sep. 18, 2002.
U.S. Appl. No. 10/259,703, filed Sep. 27, 2002.
U.S. Appl. No. 10/327,018, filed Dec. 20, 2002.
U.S. Appl. No. 10/340,237, filed Jan. 9, 2003.
U.S. Appl. No. 10/836,880, filed Apr. 30, 2004.
U.S. Appl. No. 10/836,904, filed Apr. 30, 2004.
U.S. Appl. No. 10/836,908, filed Apr. 30, 2004.
U.S. Appl. No. 10/836,911, filed Apr. 30, 2004.
U.S. Appl. No. 10/837,142, filed Apr. 30, 2004.
U.S. Appl. No. 10/837,143, filed Apr. 30, 2004.
U.S. Appl. No. 10/837,260, filed Apr. 30, 2004.
U.S. Appl. No. 10/837,291, filed Apr. 30, 2004.
U.S. Appl. No. 10/837,348, filed Apr. 30, 2004.
U.S. Appl. No. 10/837,356, filed Apr. 30, 2004.
U.S. Appl. No. 10/837,361, filed Apr. 30, 2004.
U.S. Appl. No. 10/837,379, filed Apr. 30, 2004.
U.S. Appl. No. 10/966,764, filed Oct. 14, 2004.
U.S. Appl. No. 60/567,339, filed Apr. 30, 2004.
U.S. Appl. No. 60/567,423, filed Apr. 30, 2004.
U.S. Appl. No. 60/587,092, filed Jul. 12, 2004.
U.S. Appl. No. 11/118,288, filed Apr. 29, 2005.

STEROID-CONTAINING SUSTAINED RELEASE INTRAOCULAR IMPLANTS AND RELATED METHODS

CROSS REFERENCE

This application is a continuation-in-part of U.S. application Ser. No. 11/118,288, filed Apr. 29, 2005, which is a continuation-in-part of U.S. application Ser. No. 10/837,356, filed Apr. 30, 2004, the entire contents of each of which are hereby incorporated by reference.

BACKGROUND

The present invention generally relates to devices and methods to treat an eye of a patient, and more specifically to intraocular implants that provide extended release of a therapeutic agent to an eye in which the implant is placed.

Steroids, such as the corticosteroid, fluocinolone acetonide (1,4-pregnadien-6α, 9α-difluoro-11β,16α,17,21-tetrol-3,20-dione16,17-acetonide), are usually given topically, systemically, or periocularly, as an injection, to treat uveitis. All three methods of delivery have drawbacks, e.g., topical corticosteroids do not treat diseases in the back on the eye, systemic corticosteroids are often associated with many unwanted side effects, and periocular injections may sometimes cause globe perforation, periocular fibrosis and ptosis.

An alternative that may circumvent the drawbacks of the above-mentioned delivery methods is to use sustained-released drug delivery systems. In 2000, Jaffe et al. reported using compressed pure fluocinolone acetonide pellets coated with silicone and polyvinyl alcohol as a fluocinolone sustained delivery device (Jaffe, G. J. et al., Journal of Ophthalmology and Vision Surgery, Vol 41, No. 11, October 2000). They obtained release rates of 1.9±0.25 μg/day (6 months) and 2.2±0.6 μg/day (45 days) for the 2-mg device and 15-mg device, respectively. The duration of release for the 2-mg and 15-mg device was estimated to be 2.7 and 18.6 years, respectively. U.S. Pat. Nos. 6,217,895 and 6,548,078 disclose sustained release implants for delivering a corticosteroid, such as fluocinolone acetonide, to an eye. However, fluocinolone acetonide intravitreal implants made by Control Delivery Systems (the assignee of U.S. Pat. Nos. 6,217,895 and 6,548,078) were only partially successful and led to the development of cataracts and increased intraocular pressure.

In addition, intravitreal injection of triamcinolone acetonide (KENALOG®) for treatments of non-infectious uveitis, and macular edema due to various retinal diseases has appeared to be safe and effective.

Additional biocompatible implants for placement in the eye have been disclosed in a number of patents, such as U.S. Pat. Nos. 4,521,210; 4,853,224; 4,997,652; 5,164,188; 5,443,505; 5,501,856; 5,766,242; 5,824,072; 5,869,079; 6,074,661; 6,331,313; 6,369,116; 6,699,493, and 6,726,918.

Other intravitreal therapeutic approaches are described in U.S. application Ser. No. 10/966,764, filed Oct. 14, 2004; Ser. No. 11/039,192, filed Jan. 19, 2005; and Ser. No. 60/587,092, filed Jul. 12, 2004.

It would be advantageous to provide eye implantable drug delivery systems, such as intraocular implants, and methods of using such systems, that are capable of releasing a therapeutic agent at a sustained or controlled rate for extended periods of time and in amounts with few or no negative side effects.

SUMMARY

The present invention provides new drug delivery systems, and methods of using such systems, for extended or sustained drug release into an eye, for example, to achieve one or more desired therapeutic effects while minimizing an increase in ocular pressure in the eye. The drug delivery systems are in the form of implants or implant elements that may be placed in an eye.

Intraocular implants in accordance with the disclosure herein comprise a steroid and a antiglaucoma drug. The steroid and the antiglaucoma drug may be present in or on the same implant or different implants. The antiglaucoma drug may maintain the ocular pressure in the eye in an acceptable range.

Such intraocular implants may comprise a therapeutic component and a drug release sustaining component associated with the therapeutic component. In accordance with the present invention, the therapeutic component comprises, consists essentially of, or consists of, a steroid. The drug release sustaining component is associated with the therapeutic component to sustain release of a therapeutically effective amount of the steroid into an eye in which the implant is placed. The therapeutically effective amount of the steroid is preferably released into the eye for a period of time greater than about two months after the implant is placed in the eye.

In one embodiment, the intraocular implants comprise a steroid and a biodegradable polymer matrix. The steroid is associated with a biodegradable polymer matrix that releases drug, such as by degrading, at a rate effective to sustain release of a therapeutically effective amount of the steroid from the implant for a time greater or longer than about two months from a time the implant is placed in an ocular site or region of an eye. The intraocular implant is biodegradable or bioerodible and provides a sustained release of the steroid in an eye for extended periods of time, such as for more than two months, for example for about three months or more and up to about six months or more.

The biodegradable polymer component of the foregoing implants may be a mixture of biodegradable polymers, wherein at least one of the biodegradable polymers is a polylactic acid or poly(lactide-co-glycolide) polymer having a molecular weight less than 40 kiloDaltons (kD). Additionally or alternatively, the foregoing implants may comprise a first biodegradable polymer having terminal free acid groups, and a different second biodegradable polymer having terminal free acid groups. Furthermore, the foregoing implants may comprise a mixture of different biodegradable polymers, each biodegradable polymer having an inherent viscosity in a range of about 0.16 deciliters/gram (dl/g) to about 0.24 dl/g. Examples of suitable biodegradable polymers include polymers of lactic acid, glycolic acid, and mixtures thereof.

In another embodiment, intraocular implants comprise a therapeutic component that comprises a steroid, and a polymeric outer layer covering the therapeutic component. The polymeric outer layer may include one or more orifices or openings or holes that are effective to allow a liquid to pass into the implant, and to allow the steroid to pass out of the implant. The therapeutic component is provided in a core or interior portion of the implant, and the polymeric outer layer covers or coats the core. The polymeric outer layer may include one or more biodegradable portions. The implant can provide an extended release of the steroid for more or longer than about two months, and for more than about one year, and even for more than about five or about ten years.

In one embodiment, the polymeric outer layer of the implant may comprise two or more layers or coats of biodegradable material, with each such layer having a different composition or rate of degradation than the layer immediately adjoining it. For example, the polymeric outer layer of the implant may comprise concentric rings or nested coatings comprising a first layer, wherein the first layer may comprise, for example, a biodegradable polymer and the absence of a steroid, a biodegradable polymer comprising a therapeutically effective amount of a steroid, a biodegradable polymer comprising an amount of an auxiliary agent effective to reduce at least one side effect of a steroid, and a biodegradable polymer comprising a therapeutically effective amount of a steroid and an amount of an auxiliary agent effective to reduce at least one side effect of a steroid, and a biodegradable polymer without any added drug.

A second layer may also comprise, for example, a biodegradable polymer and the absence of a steroid, a biodegradable polymer comprising a therapeutically effective amount of a steroid, a biodegradable polymer comprising an amount of an auxiliary agent able to reduce at least one side effect of a steroid, and a biodegradable polymer comprising a therapeutically effective amount of a steroid and an amount of an auxiliary agent able to reduce at least one side effect of a steroid, and a biodegradable polymer without any added drug, with the additional provisos that the first and second layers are located adjoining one another in the biodegradable implant, that the first and second layers are not identical, and that the first layer is designed to erode substantially before the second layer.

Additional layers may be present; preferably, each such layer will not be identical to the layers immediately surrounding it.

It is well known that long-term ophthalmic treatment with corticosteroids must be monitored closely due to potential toxicity and long-term side effects. For example, adverse reactions listed for conventional ophthalmic dexamethasone preparations include: glaucoma (with optic nerve damage, visual acuity and field defects, and ocular hypertension), posterior subcapsular cataract formation, and secondary ocular infection from pathogens including herpes simplex. Additional hazardous side-effects upon conventional topical treatment with steroids may comprise hypertension, hyperglycemia, increased susceptibility to infection, and peptic ulcers.

An "auxiliary agent" is an agent able to reduce at least one side effect of a steroid. An auxiliary agent comprises a compound able, in the absence of the steroid, to reduce or prevent a condition associated with at least one side effect of a steroid. Thus such a compound may include, for example, one or more neuroprotective agent such as, without limitation, memantine (and other NMDA receptor antagonists), brimonidine (and other alpha 2 adrenergic receptor agonists) can be therapeutically useful in the treatment of optic nerve and retinal damage affecting loss of visual acuity and diminution of visual field; and/or one or more ocular hypotensive agent such as, without limitation, beta blockers (such as timolol), a carbonic anhydrase inhibitor, an alpha 2 adrenergic agonist (such as clonidine, brimonidine and selective alpha 2B and/or 2C receptor agonists), and a prostaglandin or prostaglandin derivative or analog (such as bimatoprost, travoprost, and latanoprost) for the treatment of ocular hypertension; and/or one or more antiviral and antibiotic drug (for example, a quinolone antibiotic such as ofloxacin, ciprofloxacin and norfloxacin) for the prevention of secondary ocular infection.

In another embodiment, the implant may include a therapeutic agent such as a steroid, and an agent able to reduce at least one side effect of a steroid, wherein art least one of such agents is covalently joined via a biodegradable linkage to a biodegradable polymer. For example, the biodegradable polymer may comprise a plurality of hydroxyl groups to which said agent may be joined by a biodegradable linkage. Biodegradable or biocleavable linkages are defined as types of specific chemical moieties or groups that can be used within the chemical substances that covalently reversibly couple or cross-link a therapeutic agent and/or an auxiliary agent to a biodegradable polymer comprised in the implant. Thus, such linkages may be contained in certain embodiments of the instant invention that provide the function of controlled release of a steroid and/or auxiliary agent. In certain embodiments of the present invention an implant system comprising one or more implant is structured such that the therapeutic agent and the auxiliary agent are released at different rates or different times following implantation of the implant(s). Biocleavable linkages or bonds can be distinguishable by their structure and function and non-limiting examples are provided here under distinct categories or types.

One such category comprises the disulfide linkages that are well known for covalent coupling. Such linkages are stable under oxidizing conditions, but can be cleaved under reducing conditions. For drug delivery, they may be more useful for shorter periods in vivo since they are cleaved relatively easily. A simple ester bond is another preferred type that may easily be formed between an acid and an alcohol. Another preferred type is any imidoester formed from alkyl imidates. Also included are maleimide bonds as with sulfhydryls or amines used to incorporate a biocleavable linkage.

Another category in this invention comprises acid-cleavable biocleavable linkages. The preferred biocleavable linkages for such release of active agents and other moieties. One such type is an acid-sensitive (or acid-labile) hydrazone linkage as described by Greenfield, et al, Cancer Res. 50, 6600-6607 (1990), and references therein.

Another type of acid-labile linkage are the polyortho or diortho ester linkage; examples of such linkages are disclosed in J. Heller, et al., METHODS IN ENZYMOLOGY 112, 422-436 (1985), J. Heller, J. ADV. POLYMER SCI. 107, 41 (1993), M. Ahmad, et al., J. AMER. CHEM. SOC. 101, 2669 (1979) and references therein. Also useful may be acid labile phosphonamide linkages disclosed by J. Rahil, et al, J. AM. CHEM. SOC. 103, 1723 (1981) and J. H. Jeong, et al, BIOCONJ. CHEM. 14, 473 (2003).

The steroid of the implants disclosed herein may be corticosteroids, or other steroids that are effective in treating ocular conditions. One example of a suitable steroid is fluocinolone or fluocinolone acetonide. Another example of a suitable steroid is triamcinolone or triamcinolone acetonide. Another example of a suitable steroid is beclomethasone or beclomethasone dipropionate. Another example of a suitable steroid is dexamethasone or a pharmacologically acceptable salt thereof. In addition, the therapeutic component of the present implants may include one or more additional and different therapeutic agents that may be effective in treating an ocular condition.

The implants may be placed in an ocular region to treat a variety of ocular conditions, including conditions that affect an anterior region or posterior region of an eye. For example, the implants may be used to treat many conditions of the eye, including, without limitation, maculopathies and retinal degeneration, uveitis, retinitis, choroiditis, vascular diseases, and exudative diseases, proliferative disorders, infectious disorders, genetic disorders, tumors, trauma, and surgery, retinal tears or holes, and the like. In particular, treatment of retinal conditions are particularly advantageous by means if insertion, injection or other intravitreal delivery, or subconjunctival delivery of such implants.

Kits in accordance with the present invention may comprise one or more of the present implants, and instructions for using the implants. For example, the instructions may explain how to administer the implants to a patient, and types of conditions that may be treated with the implants.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying drawings and examples.

DESCRIPTION

Figure 1:
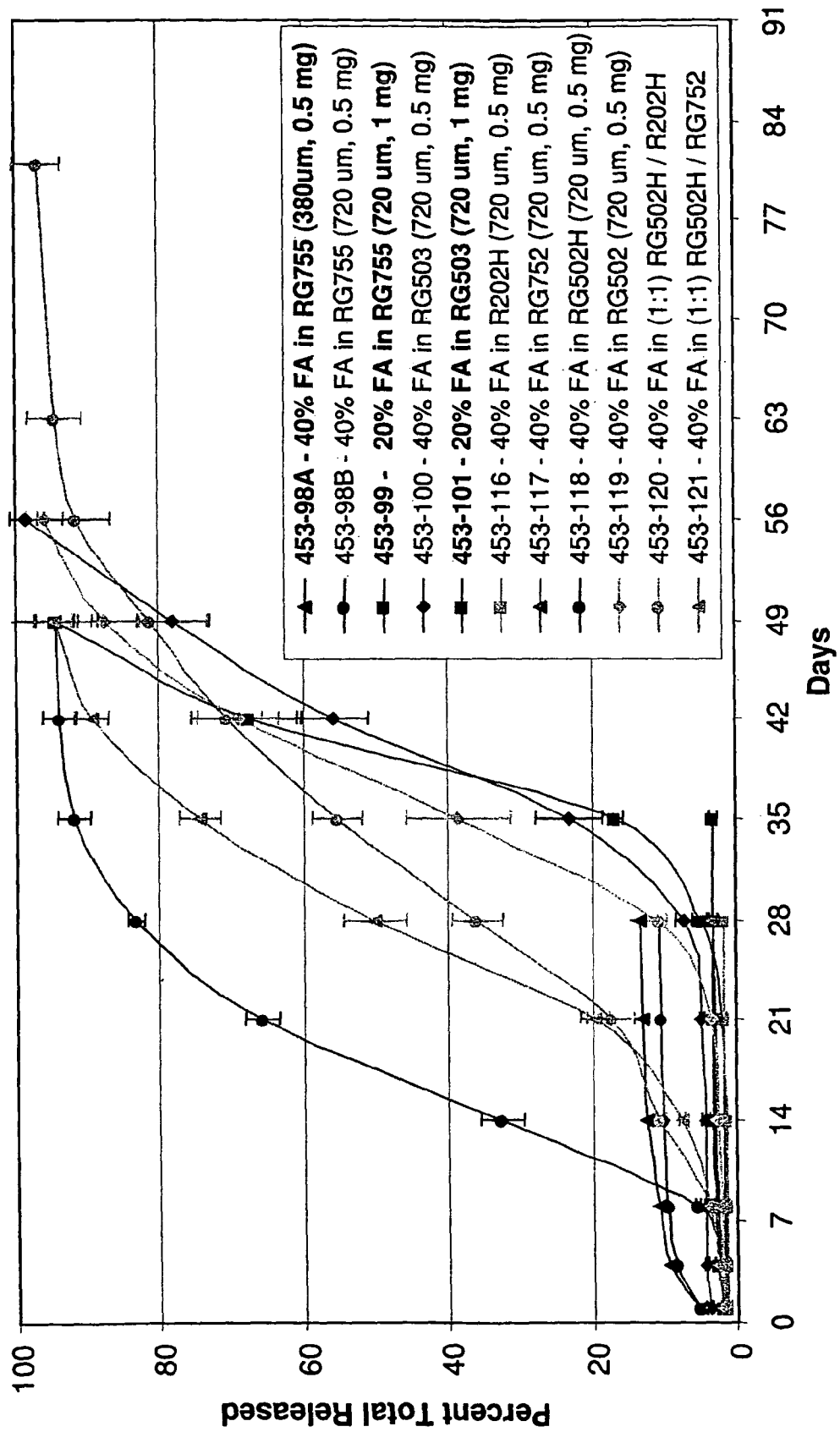
FIG. 1 is a graph showing the cumulative release profiles for biodegradable fluocinolone acetonide containing implants as determined in 0.9% saline at 37 degrees Celsius.

As described herein, controlled and sustained administration of a therapeutic agent through the use of one or more intraocular implants may improve treatment of undesirable ocular conditions. The implants comprise a pharmaceutically acceptable polymeric composition and are formulated to release one or more pharmaceutically active agents including at least one steroid and optionally at least one auxiliary agent, over an extended period of time. In certain embodiments involving the delivery of more than one agent, the dosage regiment may be formulated to provide two or more drugs to the posterior segment of the eye under different dosage regimens. For example, the dosage of the steroid in an implant may be made to be discontinuous over the treatment period while a non-discontinuous dosage of an auxiliary agent is administered in an implant over the same overall time period. The implant containing the steroid and the implant containing the auxiliary agent may be different implants or the same implant comprising means of differentially administering the steroid and auxiliary agent, such means including different coatings or shells which may contain, neither, one or both drugs (as discussed elsewhere herein), or covalent linkage of one or both drugs to a biodegradable polymer of the implant by way of a biodegradable linkage, thus permitting regulation of the delivery of one or more drug over the time of the treatment. The implants are effective to provide a therapeutically effective dosage of the agent or agents directly to a region of the eye to treat one or more undesirable ocular conditions. Thus, with a single administration, therapeutic agents will be made available at the site where they are needed and may be maintained for an extended period of time, rather than subjecting the patient to repeated injections or, in the case of self-administered drops, ineffective treatment with only limited bursts of exposure to the active agent or agents.

A preferred intraocular implant in accordance with the disclosure herein comprises a therapeutic component and a drug release sustaining component associated with the therapeutic component. In accordance with the present invention, the therapeutic component comprises, consists essentially of, or consists of, a steroid. The drug release sustaining component is associated with the therapeutic component to sustain release of a therapeutically effective amount of the steroid into an eye in which the implant is placed. The therapeutic amount of the steroid is released into the eye for a period of time greater than about two months after the implant is placed in the eye. Preferably the implant also comprises an agent able to reduce at least one side effect of a steroid (AARSS). For example, in one embodiment

DEFINITIONS

For the purposes of this description, we use the following terms as defined in this section, unless the context of the word indicates a different meaning.

As used herein, an "intraocular implant" refers to a device or element that is structured, sized, or otherwise configured to be placed "in an eye", including the subconjunctival space. Intraocular implants are generally biocompatible with physiological conditions of an eye and do not cause adverse side effects. Intraocular implants may be placed in an eye without disrupting vision of the eye.

As used herein, a "therapeutic component" refers to a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

As used herein, a "drug release sustaining component" refers to a portion of the intraocular implant that is effective to provide a sustained release of the therapeutic agents of the implant. A drug release sustaining component may be a biodegradable polymer matrix, or it may be a coating covering a core region of the implant that comprises a therapeutic component.

As used herein, "associated with" means mixed with, dispersed within, coupled to, covering, or surrounding. With respect to intraocular implants which comprise a therapeutic component associated with a biodegradable polymer matrix, "associated with" specifically excludes biodegradable polymeric coatings that may be provided on or around the matrix.

As used herein, an "ocular region" or "ocular site" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include the anterior chamber, the posterior chamber, the vitreous cavity, the choroid, the suprachoroidal space, the conjunctiva, the subconjunctival space, the episcleral space, the intracorneal space, the epicorneal space, the sclera, the pars plana, surgically-induced avascular regions, the macula, and the retina.

As used herein, an "ocular condition" is a disease, ailment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the retina but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular region or site.

Thus, a posterior ocular condition can include a disease, ailment or condition, such as for example, acute macular neuroretinopathy; Behcet's disease; choroidal neovascularization; diabetic uveitis; histoplasmosis; infections, such as fungal or viral-caused infections; macular degeneration, such as acute macular degeneration, non-exudative age related macular degeneration and exudative age related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic ophthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal cells or optic nerve cells (i.e. neuroprotection).

The term "biodegradable polymer" refers to a polymer or polymers which degrade in vivo, and wherein erosion of the polymer or polymers over time occurs concurrently with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

The term "treat", "treating", or "treatment" as used herein, refers to reduction or resolution or prevention of an ocular condition, ocular injury or damage, or to promote healing of injured or damaged ocular tissue.

The term "therapeutically effective amount" as used herein, refers to the level or amount of agent needed to treat an ocular condition, or reduce or prevent ocular injury or damage without causing significant negative or adverse side effects to the eye or a region of the eye.

Intraocular implants have been developed which can release drug loads over various time periods. These implants, which when inserted into an eye, such as, without limitation, the vitreous of an eye or the subconjunctival space, provide therapeutic levels of a steroid and/or auxiliary agent for extended periods of time (e.g., for about 2 months or more). The implants disclosed are effective in treating ocular conditions, such as posterior ocular conditions.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant may comprises a steroid and/or auxiliary agent associated with the biodegradable polymer matrix. Such association may be "passive", such as through co-extrusion of the active agent(s) with the biodegradable polymer, or "active", by being joined, or coupled to the polymer through covalent chemical bonds, chelation, strong hydrogen bonding, ionic interaction, and the like. The matrix degrades at a rate effective to sustain release of a therapeutically effective amount of the steroid for a time greater than about two months from the time in which the implant is placed in ocular region or ocular site, such as the vitreous of an eye.

The steroid of the implant may be a corticosteroid. In certain embodiments, the steroid may be a fluocinolone, a triamcinolone, or a mixture of fluocinolone and triamcinolone. In some embodiments, the fluocinolone is provided in the implant as fluocinolone acetonide, and the triamcinolone is provided in the implant as triamcinolone acetonide. Triamcinolone acetonide is publicly available under the tradename, KENALOG®. Another steroid useful in the present implants is beclomethasone or beclomethasone dipropionate. Thus, the present implants may comprise one or more of the following: fluocinolone, fluocinolone acetonide, triamcinolone, triamcinolone acetonide, beclomethasone, or beclomethasone dipropionate.

The steroid may be in a particulate or powder form and entrapped by the biodegradable polymer matrix. Usually, steroid particles will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The steroid of the implant is preferably from about 10 to 90% by weight of the implant. More preferably, the steroid is from about 50 to about 80% by weight of the implant. In a preferred embodiment, the steroid comprises about 50% by weight of the implant. In another embodiment, the steroid comprises about 70% by weight of the implant.

Suitable polymeric materials or compositions for use in the implant include those materials which are compatible, that is biocompatible, with the eye so as to cause no substantial interference with the functioning or physiology of the eye. Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, may find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyvinyl alcohol, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 60 kD, usually from about 10 to about 54 kD, more usually from about 12 to about 45 kD, and most usually less than about 40 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups. In certain implants, the matrix comprises a first biodegradable polymer having terminal acid groups, and a different second biodegradable polymer having terminal acid groups. The first biodegradable polymer may be a poly(D,L-lactide-co-glycolide). The second biodegradable polymer may be a poly(D, L-lactide).

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. As discussed herein, the matrix of the intraocular implant may release drug at a rate effective to sustain release of a therapeutically effective amount of the steroid for more than three months after implantation into an eye. In certain implants, therapeutic amounts of the steroid are released for more than four months after implantation. For example, an implant may comprise fluocinolone, and the matrix of the implant degrades at a rate effective to sustain release of a therapeutically effective amount of fluocinolone for about three months after being placed in an eye. As another example, the implant may comprise triamcinolone, and the matrix releases drug at a rate effective to sustain release of a therapeutically effective amount of triamcinolone for more than three months, such as from about three months to about six months.

The rate of release of a drug from an implant of the present invention may be related to the physical structure of the implant. In a simple but very useful embodiment, the biodegradable polymer of the present invention may comprise a substantially homogeneous matrix mixed with the active agent(s) upon drying and formulation of the matrix into an intraocular implant, the active agent may be substantially homogeneously distributed in the matrix. In such an embodiment, the release characteristics of the drug is largely determined by the nature of the solvent and the rate of degradation of the matrix.

In another embodiment the implant may comprise layers or shells of differently formulated biodegradable polymer with which the therapeutic agent and/or auxiliary agent may be associated and released. Concentrations of polymer, therapeutic agent and/or auxiliary agent may differ between layers, or the biodegradable polymer may be formulated to deliver such agents at different rates, according to different release profiles, or over different time periods that other layers, or than a core portion of the implant. Each layer may be formulated differently than at least one other layer, due, without limitation, to differences in drug concentration within different layers, absence or presence of the therapeutic agent and/or the auxiliary agent within different layers; differences in the means by which the drug(s) is associated with the polymer matrix in different layers, or the chemistry and density of the biodegradable materials.

Thus, release of a drug from the present implants can be related to the amount of a drug present in the implant and the properties of the polymers of the implant, such as polymer molecular weight and ratio of glycolic acid to lactic acid. In one embodiment of the present implants, the drug or drugs, such as the steroid and/or auxiliary agent, is released at a first rate for a first time period that is substantially independent of the polymer properties, and the drug or drugs is released at a second rate for a second time period after the first time period that is dependent on the polymer properties of the implant. For example, an implant comprises a steroid and a polymeric component that releases the steroid from the implant for a time period of about thirty days primarily due to steroid dissolution, and releases the steroid from the implant after thirty days primarily due to polymer properties.

One example of the biodegradable intraocular implant comprises a steroid (and/or auxiliary agent) associated with a biodegradable polymer matrix, which comprises a mixture of different biodegradable polymers. At least one of the biodegradable polymers is a polylactide having a molecular weight less than 40 kD. Such a mixture is effective in sustaining release of a therapeutically effective amount at least one agent(s) for a time period greater than about two months from the time the implant is placed in an eye. In certain embodiments, the polylactide has a molecular weight less than 20 kD. In other embodiments, the polylactide has a molecular weight of about 10 kD. The polylactide may be a poly(D,L-lactide), and the polylactide may include polymers having terminal free acid groups. In one particular embodiment, the matrix of the implant comprises a mixture of poly(lactide-co-glycolide) and polylactide. Each of the poly(lactide-co-glycolide) and polylactide may have terminal free acid groups.

Another example of a biodegradable intraocular implant comprises a steroid (and/or auxiliary agent) associated with a biodegradable polymer matrix, which comprises a mixture of different biodegradable polymers, each biodegradable polymer having an inherent viscosity from about 0.16 dl/g to about 0.24 dl/g. For example, one of the biodegradable polymers may have an inherent viscosity of about 0.2 dl/g. Or, the mixture may comprise two different biodegradable polymers, and each of the biodegradable polymers has an inherent viscosity of about 0.2 dl/g. The inherent viscosities identified above may be determined in 0.1% chloroform at 25° C.

Other implants may include a biodegradable polymer matrix of biodegradable polymers, at least one of the polymers having an inherent viscosity of about 0.25 dl/g to about 0.35 dl/g. Additional implants may comprise a mixture of biodegradable polymers wherein each polymer has an inherent viscosity from about 0.50 dl/g to about 0.70 dl/g.

The release of the steroid (and/or auxiliary agent) from the intraocular implant comprising a biodegradable polymer matrix may include an initial burst of release followed by a gradual increase in the amount of the agent released, or the release may include an initial delay in release of the steroid followed by an increase in release. When the implant is substantially completely degraded, the percent of the agent that has been released is about one hundred. Compared to existing implants, in one embodiment the implants disclosed herein do not completely release, or release about 100% of at least one agent (steroid and/or auxiliary agent), until after about two months of being placed in an eye. Thus, the implants exhibit a cumulative release profile that may have a shallower slope, or a lower rate of release, for longer periods of time than existing implants.

In at least one embodiment, the present implants release an active agent into the interior of the eye in an amount having a reduced toxicity relative to bolus or liquid injections of the same agent without a polymeric component. For example, it has been reported that a single or repeated 20 mg dose of Kenalog 40 results in substantial retinal changes, including changes in the retinal pigment epithelium. Such doses may be necessary in liquid formulations to provide prolonged therapeutic effects.

In comparison, the present implants can provide therapeutically effective amounts of the steroid for prolonged periods of time, or for a series of such time periods, without requiring such large doses. Thus, present implants may contain 1 mg, 2 mg, 3 mg, 4 mg, or 5 mg of a steroid, such as triamcinolone acetonide or fluocinolone acetonide, the steroid is gradually released over time without causing substantial ocular toxicity or other adverse side effects that are associated with injection of 20 mg of the steroid in a liquid formulation. The steroid may, in one embodiment, be alternated within different shells of the implant such that it is delivered only over particular time periods, with time periods of substantially less (or no) steroid being delivered intervening. In this way continued exposure of the eye to the steroid, and the side effects that may accompany such constant delivery, may be avoided or reduced. In another embodiment, an intravitreal implant comprises triamcinolone acetonide and a biodegradable polymer associated with the triamcinolone acetonide in the form of an intravitreal implant that releases the triamcinolone acetonide in amounts associated with a reduced toxicity relative to the toxicity associated with administering triamcinolone acetonide in a liquid composition.

It may be in certain cases desirable to provide a relatively constant rate of release of the steroid from the implant over the life of the implant. For example, it may be desirable for the steroid to be released in amounts from about 0.01 μg to about 2 μg per day for the live of the implant. However, the release rate may change to either increase or decrease depending on the formulation of the biodegradable polymer matrix. In addition, the release profile of the steroid may include one or more linear portions and/or one or more non-linear portions. Preferably, the release rate is greater than zero once the implant has begun to degrade or erode.

It may be desirable to include delivery of an auxiliary agent in conjunction with the intravitreal or subconjunctival delivery of a steroid in order to reduce or eliminate at least one side effect compared to the delivery of the steroid in an otherwise identical manner without the auxiliary agent. The auxiliary agent and steroid may be included in the same implant or coadministered in different implants during the same treatment period.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated or reservoir-type implant may be of benefit in some circumstances, where the therapeutic level of the drug falls within a narrow window. In addition, the therapeutic component, including the steroid, may be distributed in a non-homogenous pattern in the matrix. For example, the implant may include a portion that has a greater concentration of the steroid and/or auxiliary agent relative to a second portion of the implant.

In another embodiment of the present invention, an intraocular implant comprises a therapeutic component, including a steroid, and a drug release sustaining component including one or more coating covering a core region of the implant. The therapeutic component and/or auxiliary agent is provided in the core region. The polymeric outer layer may be relatively impermeable to the therapeutic component and ocular fluids. Or, the polymeric outer layer may be initially impermeable to the therapeutic component and ocular fluids, but then may become permeable to the therapeutic component or ocular fluids as the outer layer degrades. Thus, the polymeric outer layer may comprise a polymer such as polytetrafluoroethylene, polyfluorinated ethylenepropylene, polylactic acid, polyglycolic acid, silicone, or mixtures thereof.

The foregoing implant may be understood to include a reservoir of one or more therapeutic agents, such as a steroid and/or auxiliary agent. In certain implants, the steroid may be a corticosteroid, such as fluocinolone or triamcinolone, as discussed above. One example of an implant including a reservoir of a therapeutic agent is described in U.S. Pat. No. 6,331,313.

In some implants, the drug release sustaining component comprises a polymeric outer layer covering the therapeutic component and/or the auxiliary agent, the outer layer comprises a plurality of openings or holes through which the therapeutic component may pass from the drug delivery system to an external environment of the implant, such as an ocular region of an eye. The holes enable a liquid to enter into the interior of the implant and dissolve the agent contained therein. The release of the therapeutic agent and/or auxiliary agent from the implant may be influenced by the drug solubility in the liquid, the size of the hole(s), and the number of holes. In certain implants, the hole size and number of holes are effective in providing substantially all of the desired release characteristics of the implant. Thus, additional excipients may not be necessary to achieve the desired results. However, in other implants, excipients may be provided to further augment the release characteristics of the implant.

Various biocompatible substantially impermeable polymeric compositions may be employed in preparing the outer layer of the implant. Some relevant factors to be considered in choosing a polymeric composition include: compatibility of the polymer with the biological environment of the implant, compatibility of the drug with the polymer, ease of manufacture, a half-life in the physiological environment of at least several days, no significant enhancement of the viscosity of the vitreous, and the desired rate of release of the drug. Depending on the relative importance of these characteristics, the compositions can be varied. Several such polymers and their methods of preparation are well-known in the art. See, for example, U.S. Pat. Nos. 4,304,765; 4,668,506 4,959,217; 4,144,317, and 5,824,074, Encyclopedia of Polymer Science and Technology, Vol. 3, published by Interscience Publishers, Inc., New York, latest edition, and Handbook of Common Polymers by Scott, J. R. and Roff, W. J., published by CRC Press, Cleveland, Ohio, latest edition.

The polymers of interest may be homopolymers, copolymers, straight, branched-chain, or cross-linked derivatives. Some exemplary polymers include: polycarbamates or polyureas, cross-linked poly(vinyl acetate) and the like, ethylene-vinyl ester copolymers having an ester content of 4 to 80% such as ethylene-vinyl acetate (EVA) copolymer, ethylene-vinyl hexanoate copolymer, ethylene-vinyl propionate copolymer, ethylene-vinyl butyrate copolymer, ethylene-vinyl pentanoate copolymer, ethylene-vinyl trimethyl acetate copolymer, ethylene-vinyl diethyl acetate copolymer, ethylene-vinyl 3-methyl butanoate copolymer, ethylene-vinyl 3-3-dimethyl butanoate copolymer, and ethylene-vinyl benzoate copolymer, or mixtures thereof.

Additional examples include polymers such as: poly(methylmethacrylate), poly(butylmethacrylate), plasticized poly(vinylchloride), plasticized poly(amides), plasticized nylon, plasticized soft nylon, plasticized poly(ethylene terephthalate), natural rubber, silicone, poly(isoprene), poly(isobutylene), poly(butadiene), poly(ethylene), poly(tetrafluoroethylene), poly(vinylidene chloride), poly(acrylonitrile, cross-linked poly(vinylpyrrolidone), chlorinated poly(ethylene), poly(trifluorochloroethylene), poly(ethylene chlorotrifluoroethylene), poly(tetrafluoroethylene), poly(ethylene tetrafluoroethylene), poly(4,4'-isopropylidene diphenylene carbonate), polyurethane, poly(perfluoroalkoxy), poly(vinylidenefluoride), vinylidene chloride-acrylonitrile copolymer, vinyl chloride-diethyl fumarate copolymer, silicone, silicone rubbers (of medical grade such as Silastic® Medical Grade ETR Elastomer Q7-4750 or Dow Corning® MDX 4-4210 Medical Grade Elastomer); and cross-linked copolymers of polydimethylsilane silicone polymers.

Some further examples of polymers include: poly(dimethylsiloxanes), ethylene-propylene rubber, silicone-carbonate copolymers, vinylidene chloride-vinyl chloride copolymer, vinyl chloride-acrylonitrile copolymer, vinylidene chloride-acrylonitrile copolymer, poly(olefins), poly(vinyl-olefins), poly(styrene), poly(halo-olefins), poly(vinyls) such as polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasticized ethylene vinylacetate copolymer, polyvinyl alcohol, polyvinyl acetate, ethylene vinylchloride copolymer, polyvinyl esters, polyvinylbutyrate, polyvinylformal, poly(acrylate), poly(methacrylate), poly(oxides), poly(esters), poly(amides), and poly(carbonates), or mixtures thereof.

In some aspects, the implants with an outer layer coating with holes may be biodegradable wherein the outer layer degrades after the drug has been released for the desired duration. The biodegradable polymeric compositions may comprise any of the above-identified biodegradable polymers or combinations thereof. In some implants, the polymer is polytetrafluoroethylene, (commercially known as Teflon®), ethyl vinyl alcohol or ethylene vinyl acetate.

The steroid containing implants typically exhibited desirable release times with orifices configured to have a total area of less than 1% of the total surface area of the implant. A substantially cylindrically shaped implant has a first end, a second end, and a body portion between the first end and the second end. Typically, the implants disclosed herein are sealed at the first and second ends. One or more holes are formed in the body portion of the implant. The holes typically have a diameter of at least about 250 µm and less than about 500 µm. For example, holes may have a diameter of about 250 µm, 325 µm, 375 µm, or 500 µm. Smaller holes may be provided in other implants. Typically, two or three holes are provided in the implant outer layer. The holes may be spaced apart by a distance from about 1 mm to about 2 mm for implants having a length of about 7 mm to about 10 mm.

In one steroid-containing implant, the total area of the holes was about 0.311% of the total surface area of the implant. In another steroid-containing implant, the total area of the holes was about 0.9% of the total surface area of the implant. The area of an orifice or hole is determined by the following formula:

$$Area = 3.1416 \times r^2$$

where r is the radius of the orifice. The area for each orifice may be determined and added together to determine the total orifice area. The tubular implant surface area may be determined by the following formula:

$$Surface\ area = 3.1416 \times OD \times length + 2 \times 3.1416 r_{od}^2$$

where OD is the outer diameter of a cross-section of the tubular implant, length is the length of the tubular implant, and $r_{od}$ is the radius of the cross-section of the tubular implant.

In the configurations described above, the implant is capable of releasing the steroid at concentrations less than 2 µg/day. Some implants were capable of releasing the steroid at a concentration of about 0.5 µg/day. These implants are capable of providing therapeutically effective amounts of the steroid to an ocular region of an eye for more than one year, such as for more than five years, and even for about 13 years.

Examples of materials used and methods of making such implants are disclosed in U.S. Pat. No. 6,331,313. Briefly, a coating is formed around a core containing a therapeutic agent. The core may include a therapeutic agent (or a therapeutic component and an auxiliary agent) associated with a biodegradable polymer matrix, or the core may be formed by filling a preformed coating, such as a tube.

The therapeutic agent and auxiliary agent can each be deposited in a preformed coating as a dry powder, particles, granules, or as a compressed solid. The agent or agents may also be present in a solution. In addition, the core can comprise a mixture of a biodegradable polymer matrix and the agent or agents, such as the matrix containing implants described above. The polymers used in the matrix with the therapeutic agent and/or auxiliary agent are bio-compatible with body tissues and body fluids and can be biodegradable or substantially insoluble in the body fluids. Any of the above-described biocompatible polymer compositions can be used to prepare the matrix. The amount of polymer in the core may be from about 0% to 80 wt % by weight. These polymers are commercially available and methods for preparing polymer matrices are well-known in the art. See, for example, U.S. Pat. No. 5,882,682.

The biocompatible, substantially impermeable outer layer can be obtained by coating the core with a polymeric composition described above. The coat can be applied using organic solvents, and the solvents may then be vacuum stripped from the coat to leave a dry coat. The polymer, at a concentration of from about 10 to about 80 weight percent is dissolved or suspended in an organic solvent at the appropriate temperature, for example for polylactic polymer, between 60 degrees to 90 degrees C. The resulting mixture can be cut, molded, injection molded, extruded, or poured or sprayed onto a pre-formed core into any shape or size for implantation. The spraying can be accomplished in a rotating pan coater or in a fluidized bed coater until the desired coating thickness is achieved.

Alternatively, the core may be dip coated or melt coated. This type of coating is especially useful with waxes and oils. In another embodiment, the core may be compression coated, wherein a suitable polymeric composition may be pressed onto a preformed core. In another aspect, an adhesive coat such as shellac or polyvinyl acetate phthalate (PVAP) is applied to the core prior to applying the impermeable coating in order to improve adhesion of the impermeable coating to the core. These techniques are well-known in the art. See, for example, Handbook of Common Polymers, by J. R. Scott and W. J. Roff, Section 64, (1971) published by CRC Press, Cleveland, Ohio.

When the outer layer is injection molded or extruded into the desired shape, the cavity formed by the outer layer can be then filled with the therapeutic agent and/or auxiliary agent composition. Then, the ends are sealed with an end cap. At least one orifice is drilled in the device. Optionally, an orifice is drilled, or preformed in the wall, or an orifice is sealed with a break-off tab that is broken open, or cut open, or the like, at the time of use.

Alternatively, the core-free device may be loaded with therapeutic agent by, for example, immersing the device in a solution comprising the therapeutic agent for a time sufficient for absorption of the therapeutic agent. The device may be equipped with a hollow fiber and the therapeutic agent and/or auxiliary agent may be directly loaded into the fiber and the device subsequently sealed. Where the activity of the therapeutic agent and/or auxiliary agent will not be compromised, the therapeutic agent-filled device may then be dried or partially dried for storage until use. This method may find particular application where the activity of the therapeutic agent of choice is sensitive to exposure to solvents, heat or other aspects of the conventional solvent-evaporation, molding, extrusion or other methods described above.

The orifice may be formed using any technique known in the art. For instance, the orifice may be made using a needle or other form of boring instrument such as a mechanical drill or a laser to remove a section of the impermeable portion of the device. Alternatively, a specially designed punch tip may be incorporated into the compressing equipment, in order to pierce through the impermeable portion at the point of compaction.

The holes may be made by drilling the appropriate size hole through a wall of the device using a mechanical or laser-based process. In some implants, a digital laser marking system is used to drill the holes. This system allows for an array of apertures to be drilled on both faces of a dosage form simultaneously and at rates suitable for production of dosage forms. The process utilizes a digital laser marking system (for example the DigiMark™ variable marking system, available from Directed Energy, Inc.) to produce an unlimited number of holes through the surface or coating of the dosage form, at rates practically suitable for production of dosage forms.

The steps involved in this laser drilling process are as follows: a digital laser marking system is focused at a laser stage; the dosage form is moved onto the laser stage of the digital laser marking system is pulsed to energize those laser tubes needed to drill the desired apertures along a linear array on the dosage form, the dosage form is moved forward on the laser stage and the digital laser marking system is again pulsed as needed to produce an additional linear array of apertures; the dosage form is then removed from the laser stage.

Orifices and equipment for forming orifices are disclosed in U.S. Pat. Nos. 3,845,770; 3,916,899; 4,063,064 and 4,008,864. Orifices formed by leaching are disclosed in U.S. Pat. Nos. 4,200,098 and 4,285,987. Laser drilling machines equipped with photo wavelength detecting systems for orienting a device are described in U.S. Pat. No. 4,063,064 and in U.S. Pat. No. 4,088,864.

The intraocular implants disclosed herein may have a size of between about 5 µm and about 10 mm, or between about 10 µm and about 1 mm for administration with a needle, greater than 1 mm, or greater than 2 mm, such as 3 mm or up to 10 mm, for administration by surgical implantation. For needle-injected implants, the implants may have any appropriate length so long as the diameter of the implant permits the implant to move through a needle. For example, implants having a length of about 6 mm to about 7 mm have been injected into an eye. The implants administered by way of a needle should have a diameter that is less than the inner diameter of the needle. In certain implants, the diameter is less than about 500 µm. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants, particularly the implants with the steroid and/or auxiliary agent associated with a biodegradable polymer matrix, may be of any geometry including fibers, sheets, films, microspheres and microparticles, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 µm to 4 mm in diameter, with comparable volumes for other shaped particles.

In certain embodiments of the present invention the use if microsphere implants may be particularly advantageous. A method of making such microspheres involves combining, associating or mixing the therapeutic and/or auxiliary agent with a biodegradable polymer or polymers. The mixture may then be extruded or compressed to form a single composition. The single composition may then be processed to form microspheres suitable for placement intravitreally or subconjunctivally.

Alternatively, a method of making the present microspheres may also include using an oil-in-oil emulsion process to form the microspheres. Such methods may be particularly useful in forming microparticles, nanoparticles and the like. Thus, an embodiment of the present invention relates to the inserts comprising microparticles made using an oil-in-oil emulsion process.

The microspheres, which may include a population of microparticles or nanoparticles, may be placed in an ocular region such as, without limitation, intravitreally or subconjunctivally, to treat a variety of ocular conditions. For example, the microspheres may be administered intravitreally in a manner effective to delivering a therapeutic component and/or auxiliary agent to tissues of the posterior segment, thereby reducing damage to the tissues of the posterior segment while reducing at least one side effect as compared to the administration of the steroid alone in an otherwise identical manner. Alternatively, subconjunctival administration of the microspheres of the present invention are very effective at delivering the therapeutic component to the retina and other tissues of the posterior segment for the treatment of neurodegenerative conditions such as age related macular degeneration (ARMD), such as "wet" or "dry" ARMD, macular edema, etc.

The use of microspheres, microparticles and the like provides an excellent means of punctuated delivery of the steroid in the implants of the present invention. For example, in one embodiment different lots (comprising the same or different sizes of microparticles) are made, each having a different property, such as different rates of erosion; different drug content (for example some may contain a steroid and an auxiliary agent, while others may just contain the auxiliary agent; some may be made of one bioerodible polymer having a fast dissolution rate, while others may be made of a different biopolymer having a slower dissolution rate. By engineering the microparticles so that during the treatment period the dosage of steroid is "pulsed", for example, from an initial substantially optimal therapeutically effective dosage to a subsequent period lacking a substantially optimal therapeutically effective dosage of the steroid and optionally to another treatment time period in which a substantially optimal therapeutically effective dosage of the steroid is again administered, at least one of the deleterious side effects of long term steroid use can be lessened. Some microspheres may, for example, be loaded with the auxiliary agent, either alone or in combination with the steroid, to provide a substantially constant (or at least slowly decaying) dosage of the auxiliary agent to ocular tissues during the treatment period, while the dosage of steroid may vary.

Thus, the combination of different microspheres in a discretely administered intravitreal or subconjunctival injection or insertion provides a powerful way to separately tailor the administration of steroid and auxiliary agent. Methods of making microspheres are provided in U.S. application Ser. No. 11/303,462, and U.S. application Ser. No. 10/837,260, under common ownership with the present application, the entire contents of both of which prior applications are hereby incorporated by reference.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of steroid and/or auxiliary agent, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the steroid or steroids included in the intraocular implants disclosed herein, the intraocular implants may also include one or more additional ophthalmically acceptable therapeutic agents. For example, the implant may include one or more antihistamines, one or more antibiotics, one or more beta blockers, one or more different corticosteroids, one or more neuroprotectant agent, one or more anti-glaucoma agent, one or more antibiotic, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. No. 4,474,451, columns 4-6 and U.S. Pat. No. 4,327,725, columns 7-8.

Examples of antihistamines include, and are not limited to, loratadine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimeprazine doxylamine, pheniramine, pyrilamine, chlorcyclizine, thonzylamine, and derivatives thereof.

Examples of antibiotics include without limitation, cefazolin, cephradine, cefaclor, cephapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, ofloxacin, ciprofloxacin, norfloxacin, and derivatives thereof.

Examples of beta blockers include acebutolol, atenolol, labetalol, metoprolol, propranolol, timolol, and derivatives thereof.

Examples of other corticosteroids include cortisone, prednisolone, fluorometholone, dexamethasone, medrysone, loteprednol, fluazacort, hydrocortisone, prednisone, betamethasone, prednisone, methylprednisolone, triamcinolone hexacetonide, paramethasone acetate, diflorasone, fluocinonide, derivatives thereof, and mixtures thereof.

Examples of antineoplastic agents include adriamycin, cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Examples of immunosuppressive agents include cyclosporine, azathioprine, tacrolimus, and derivatives thereof.

Examples of antiviral agents include interferon gamma, zidovudine, amantadine hydrochloride, ribavirin, acyclovir, valaciclovir, dideoxycytidine, phosphonoformic acid, ganciclovir, and derivatives thereof.

Examples of antioxidant agents include ascorbate, alpha-tocopherol, mannitol, reduced glutathione, various carotenoids, cysteine, uric acid, taurine, tyrosine, superoxide dismutase, lutein, zeaxanthin, cryptoxanthin, astaxanthin, lycopene, N-acetyl-cysteine, carnosine, gamma-glutamyl-cysteine, quercetin, lactoferrin, dihydrolipoic acid, citrate, Ginkgo Biloba extract, tea catechins, bilberry extract, vitamins E or esters of vitamin E, retinyl palmitate, and derivatives thereof.

Other therapeutic agents include squalamine, carbonic anhydrase inhibitors, alpha agonists, prostamides, neuroprotectants such as NMDA receptor antagonists and alpha 2 adrenergic agonists, prostaglandins, antiparasitics, antifungals, and derivatives thereof.

The amount of active agent or agents employed in the implant, individually or in combination, will vary widely depending on the effective dosage required and the desired rate of release from the implant. Usually the agent will be at least about 1, more usually at least about 10 weight percent of the implant, and usually not more than about 80, more usually not more than about 40 weight percent of the implant.

In addition to the therapeutic component and/or auxiliary agent, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In some situations mixtures of implants may be utilized employing the same or different pharmacological agents. In this way, a cocktail of release profiles, giving a multiphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the glucocorticoid in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The implants of the present invention may be inserted into the eye, for example the vitreous chamber of the eye, by a variety of methods, including placement by forceps or by trocar following making a 2-3 mm incision in the sclera. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The implants of the present invention may also, or alternatively, be inserted into the subconjunctival space such as by injection or surgical insertion. Applicants are aware that effective retinal delivery is effectively provided by such subconjunctival administration.

Among the diseases/conditions which can be treated or addressed in accordance with the present invention include, without limitation, the following:

MACULOPATHIES/RETINAL DEGENERATION: Non-Exudative Age Related Macular Degeneration (ARMD), Exudative Age Related Macular Degeneration (ARMD), Choroidal Neovascularization, Diabetic Retinopathy, Acute Macular Neuroretinopathy, Central Serous Chorioretinopathy, Cystoid Macular Edema, Diabetic Macular Edema.

UVEITIS/RETINITIS/CHOROIDITIS: Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome.

VASCULAR DISEASES/EXUDATIVE DISEASES: Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease.

TRAUMATIC/SURGICAL: Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy.

PROLIFERATIVE DISORDERS: Proliferative Vitreal Retinopathy and Epiretinal Membranes, Proliferative Diabetic Retinopathy.

INFECTIOUS DISORDERS: Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associated with HIV Infection, Uveitic Disease Associated with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis.

GENETIC DISORDERS: Retinitis Pigmentosa, Systemic Disorders with Associated Retinal Dystrophies, Congenital Stationary Night Blindness, Cone Dystrophies, Stargardt's Disease and Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum.

RETINAL TEARS/HOLES: Retinal Detachment, Macular Hole, Giant Retinal Tear.

TUMORS: Retinal Disease Associated with Tumors, Congenital Hypertrophy of the RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

MISCELLANEOUS: Punctate Inner Choroidopathy, Acute Posterior Multifocal Placoid Pigment Epitheliopathy, Myopic Retinal Degeneration, Acute Retinal Pigment Epithelitis and the like.

In one embodiment, an implant, such as the implants disclosed herein, is administered to a posterior segment of an eye of a human or animal patient, and preferably, a living human or animal. In at least one embodiment, an implant is administered without accessing the subretinal space of the eye. For example, a method of treating a patient may include placing the implant directly into the posterior chamber of the eye. In other embodiments, a method of treating a patient may comprise administering an implant to the patient by at least one of intravitreal injection, subconjunctival injection, sub-tenon injections, retrobulbar injection, and suprachoroidal injection.

In at least one embodiment, a method of treating a posterior ocular condition comprises administering one or more implants containing one or more steroids, as disclosed herein to a patient by at least one of intravitreal injection, subconjunctival injection, sub-tenon injection, retrobulbar injection, and suprachoroidal injection. A syringe apparatus including an appropriately sized needle, for example, a 22 gauge needle, a 27 gauge needle or a 30 gauge needle, can be effectively used to inject the composition with the posterior segment of an eye of a human or animal. Repeat injections are often not necessary due to the extended release of the steroid from the implants.

The present implants provide prolonged therapy to patients in need of ocular therapy. As discussed herein, the present implants can release a steroid for at least about 2 months after placement in the vitreous of an eye of a patient. In certain implants, the steroid, and/or other therapeutic agents, can be released for at least about one year, for example for about three years. In additional implants, the steroid and/or auxiliary agent can be released at therapeutically effective amounts for more than three years, such as for about five years.

In another aspect of the invention, kits for treating an ocular condition of the eye are provided, comprising: a) a container comprising an extended release implant comprising a therapeutic component including a steroid, such as fluocinolone or triamcinolone, an auxiliary agent, and optionally a drug release sustaining component; and b) instructions for use. Instructions may include steps of how to handle the implants, how to insert the implants into an ocular region, and what to expect from using the implants.

In view of the disclosure herein, one embodiment of a biodegradable intraocular implant comprises a steroid, such as triamcinolone acetonide, fluocinolone acetonide, dexamethasone, and the like, optionally an auxiliary agent, and a biodegradable polymeric component, and substantially no polyvinyl alcohol. Such an implant may be useful in treating uveitis, including non-infectious uveitis, and other ocular disorders, including macular edema, age-related macular degeneration, and the disorders described herein. Advantageously, these implants can be placed in the vitreous of an eye of a patient, and can provide one or more therapeutic benefits with relatively few or no side effects. For example, the steroid, such as fluocinolone acetonide, can be released from the implant without the patient developing cataracts, vitreous hemorrhage, retinal neovascularization, and/or ocular hypertension.

In another embodiment, the implant can comprise a steroid, such as fluocinolone acetonide, optionally an auxiliary agent, and the implant can have a form other than a tablet. For example, the implant can be in the form of a rod, sphere, particle and the like. In certain implants, the implant is an extruded element as compared to a compressed tablet. The implant may include an adhesive component effective in retaining the implant in a fixed position in the eye. For example, certain implants, such as non-tablet implants, may include a polyvinyl alcohol suture. Other implants, including compressed tablets, may include an adhesive component that is free of polyvinyl alcohol. For example, a hydrogel material may be used to affix the implant in the eye of a patient.

In another embodiment, a steroid-containing intraocular tablet may comprise a polyvinyl alcohol coating over the tablet body, and be substantially free of a silicone component. Some examples of useful coatings include those described above.

In a further embodiment, an implant can comprise a steroid, such as fluocinolone acetonide or triamcinolone acetonide, and an intraocular pressure reducing agent or antiglaucoma drug. These implants may be particularly useful in preventing an increase in intraocular pressure associated with release of the steroid from the implant into the eye. The term antiglaucoma drug, as used herein, is meant to include both the terms intraocular pressure reducing agent and antiglaucoma drug.

It will be understood that antiglaucoma drugs need not necessarily be ocular hypotensive drugs. Although elevated intraocular pressure accompanies most cases of glaucoma, is not always present. Thus, for example, "low-tension" or "normal-tension" glaucoma is a condition that causes optic nerve damage and narrowed side vision in people with normal eye pressure. While lowering eye pressure helps at least 30 percent of these patients slow the progression of the disease, glaucoma may worsen in others despite low intraocular pressure.

Therefore, certain antiglaucoma drugs may have neuroprotective activity in addition to, or instead of ocular hypotensive activity.

A wide range of antiglaucoma drugs may be utilized in the ocular implants according to embodiments of the present invention. For example, six types of antiglaucoma drugs are listed on the website of the New York Glaucoma Research Institute (NYGRI), www.glaucoma.net/nygri/glaucoma/topics/drugs.html. It will be understood that this classification of antiglaucoma drugs contains some overlap, does not necessarily contain all classes of therapeutic agents useful for the treatment of glaucoma, and is not necessarily the sole classes of antiglaucoma agents. These types are: 1. Parasympathomimetics; 2. Sympathomimetics; 3. Alpha agonists; 4. Beta Blockers; 5. Carbonic anhydrase inhibitors; and 6. Prostaglandin analogs.

Implants according to embodiments of the present invention may comprise one or more types of antiglaucoma drugs. In addition to the 6 types of antiglaucoma drugs listed on the NYGRI website, other types of antiglaucoma drugs may be utilized in the implants in alternative embodiments.

Antiglaucoma drugs have been reviewed, for example, by Ivan Goldberg in *Aust. Preser.* 25, 142 (2002), and by S. D. Mathebula in *The South African Optometrist*, September, 2005, pages 89-95. The antiglaucoma drugs that are described in these reviews may be employed as antiglaucoma drugs in the implants according to embodiments of the present invention.

Intraocular pressure reducing agents or antiglaucoma drugs may reduce the intraocular pressure through various mechanisms. Although the following discussion generally follows the classification scheme of the six types of antiglaucoma drugs on the NYGRI website for convenience, the discussion is illustrative only and is not meant to be limiting.

1. Parasympathomimetics

Parasympathomimetics, also known as miotics, cholinomimetics, or cholinergic agents, may function by opening the trabecular meshwork and increase the rate of fluid outflow from the anterior chamber of the eye. Some nonlimiting examples of parasympathomimetics include pilocarpine, carbachol, and echothiophate and their derivatives.

2. Sympathomimetics

Sympathomimetics, also known as adrenergic agonists, may lower the intraocular pressure by increasing the rate of fluid outflow from the anterior chamber of the eye and may also decrease the rate of aqueous humor production.

Epinephrine (adrenaline) may be the most commonly used sympathomimetic antiglaucoma drug; it is a natural agonist at alpha 2 adrenergic receptors. Dipivefrin is a precursor of epinephrine and may be converted to epinephrine inside the eye. Dipivefrin may therefore also be considered to be a sympathomimetic.

Other sympathomimetics may also be suitable.

3. Alpha Agonists

Alpha-agonists, particularly those possessing alpha 2 adrenergic receptor activity, may reduce aqueous humor production and increase aqueous humor outflow. Apraclonidine, clonidine, p-aminoclonidine, oxymetazoline, epinephrine, norepinephrine, and cirazoline, dexmedetomidine, mivazerol, xylazine, medetomidine, and brimonidine are nonlimiting examples of such alpha 2 agonists. Compounds possessing selective alpha 2 activity, that is a minimum of alpha 1 agonist activity, are particularly helpful.

Additionally, newer classes of alpha 2 agonist compounds, such as those compounds possessing alpha 2B and/or alpha 2C selective activity, may be particularly useful in providing antiglaucoma activity without concomitant sedation or cardiovascular suppression.

Examples of such compounds, methods of their making, and methods of screening such compounds are provided, for example and without limitation, in the following publications, all of which are incorporated herein by reference in their entirety: U.S. Pat. Nos. 6,329,369; 6,545,182; 6,841,684 and U.S. Patent Publications Serial No US20020161051, entitled "(2-hydroxy)ethyl-thioureas useful as modulators of alpha2B adrenergic receptors"; US20030023098, entitled "Compounds and method of treatment having agonist-like activity selective at alpha 2B or 2B/2C adrenergic receptors"; US20030092766, entitled "Methods and compositions for modulating alpha adrenergic receptor activity"; US20040220402, entitled "4-(substituted cycloalkylmethyl) imidazole-2-thiones, 4-(substituted cycloalkenylmethyl)imidazole-2-thiones, 4-(substituted cycloalkylmethyl)imidazol-2-ones and 4-(substituted cycloalkenylmethyl)imidazol-2-ones and related compounds"; US20040266776, entitled "Methods of preventing and reducing the severity of stress-associated conditions"; US20050059664 entitled "Novel methods for identifying improved, non-sedating alpha-2 agonists"; US20050059721, entitled "Nonsedating alpha-2 agonists"; US20050059744 entitled "Methods and compositions for the treatment of pain and other alpha 2 adrenergic-mediated conditions"; and US20050075366 entitled "4-(2-Methyl-5,6,7,8-tetrahydro-quinolin-7-ylmethyl)-1,3-dihydro-imidazole-2-thione as specific alpha2B agonist and methods of using the same". Additional disclosure concerning non-sedating alpha 2 adrenergic agonists can be found in US20050058696, entitled Methods and Compositions for the Treatment of Pain and other Alpha 1 Adrenergic Mediated Conditions", and US20040132824, entitled "Novel Methods and Compositions of Alleviating Pain". All the patents and patent applications referenced above are incorporated by reference herein in their entirety.

These publications show that such non-sedating $\alpha 2$ receptor agonist compositions contain agents that have already been characterized in a wide variety of chemical classes, including the imidazole, thiourea, imidazoline, and imidazole thione, phenethylamine, amino thiazine, amino imidazoline, benzazepine, amino oxazoline, amino thiazoline, quinazoline, guanidine, piperazine, yohimbine alkaloid, and phenoxypropanolamine chemical classes. It is to be expected that future non-sedating $\alpha 2$ agents (or combinations of agents) will be found in additional chemical classes.

In particular, it has been found that non-sedating $\alpha 2$ adrenergic agonist compositions have certain biochemical properties in common, regardless of the chemical structure of the agents contained in the compositions. For example, in one embodiment such compounds, in addition to having $\alpha 2$ adrenergic agonist activity, particularly but not necessarily exclusively, $\alpha 2B$ and/or $\alpha 2C$ adrenoreceptor activity, also lack significant $\alpha 1$ adrenoreceptor activity. However, in another embodiment, a therapeutic composition comprising a non-sedating $\alpha 2$ adrenergic agonist may comprise a combination of an $\alpha 2$ adrenergic agonist with an $\alpha 1$ adrenergic antagonist. In each case, the reduced or absent $\alpha 1$ adrenergic activity results in a significant increase in the efficacy of the α2 adrenergic agonist activity (reduced EC50 or concentration at which half the maximum therapeutic effect for that compound is seen) with no significant increase in the potency of the sedative activity. Thus, at therapeutically effective concentrations, the α2 adrenergic agonist has little or no sedative effect, particularly as compared to a composition comprising an α2 adrenergic agonist at a dosage conferring the same therapeutic effect, but lacking significant α1A inhibitory activity.

Other classes of non-sedating alpha 2 receptor agonists may include those having alpha 2B and/or alpha 2C agonist activity, but lacking alpha 2A receptor activity. These compounds have greatly reduced or absent sedative activity, but retain the neuroprotective and ocular hypotensive activities characteristic of alpha 2 agonists.

4. Beta-Blockers

Beta-blockers, also known as sympatholytics or adrenergic antagonists, can decrease the rate at which fluid flows into the anterior chamber of the eye. According to the Mathebula review, beta blockers can inhibit aqueous humor formation while leaving the rate of aqueous humor outflow unchanged.

Nonlimiting examples of commonly used beta-blockers include timolol, levobunolol, metipranolol, carteolol, and betaxolol.

5. Carbonic Anhydrase Inhibitors

Carbonic anhydrase inhibitors (CAIs) inhibit the enzyme carbonic anhydrase. Carbonic anhydrase is an important enzyme in the body's formation of aqueous humor. Inhibiting the formation of aqueous humor may reduce the intraocular pressure by better modulating the rates of aqueous humor inflow and outflow. According to the Mathebula review, when the intraocular pressure needs to be lowered quickly, carbonic anhydrase inhibitors may be the drugs of choice to achieve this purpose.

Some nonlimiting examples of carbonic anhydrase inhibitors include dorzolamide, brinzolamide, and dichlorphenamide.

6. Prostaglandin Analogs and Derivatives

Prostaglandin analogs and derivatives may increase uveoscleral outflow of the aqueous humor. Prostaglandins were regarded as potent ocular hypertensives for many years; however, evidence accumulated in the last two decades shows that some prostaglandins are highly effective ocular hypotensive agents and are ideally suited for the long-term medical management of glaucoma. (See, for example, Starr, M. S. EXP. EYE RES. 1971, 11, pp. 170-177; Bito, L. Z. BIOLOGICAL PROTECTION WITH PROSTAGLANDINS Cohen, M. M., ed., Boca Raton, Fla., CRC Press Inc., 1985, pp. 231-252; and Bito, L. Z., APPLIED PHARMACOLOGY IN THE MEDICAL TREATMENT OF GLAUCOMAS, Drance, S. M. and Neufeld, A. H. eds., New York, Grune & Stratton, 1984, pp. 477-505). These references are hereby incorporated by reference in their entirety. Such prostaglandins include PGF2α, PGF1α, PGE2, and certain lipid-soluble esters, such as $C_1$ to $C_5$ alkyl esters, e.g. 1-isopropyl ester, of such compounds.

In U.S. Pat. No. 4,599,353 certain prostaglandins, in particular PGE2 and $PGF2_\alpha$ and the $C_1$ to $C_5$ alkyl esters of the latter compound, were reported to possess ocular hypotensive activity and were recommended for use in glaucoma management.

The precise mechanism by which prostaglandins exert their effects is not yet known. However, while not wishing to be limited by theory, recent experimental results indicate that the prostaglandin-induced reduction in intraocular pressure results from increased uveoscleral outflow [Nilsson et al., INVEST. OPHTHALMOL. VIS. SCI. 28(suppl), 284 (1987)].

The isopropyl ester of PGF2α has been shown to have significantly greater hypotensive potency than the parent compound, which was attributed to its more effective penetration through the cornea. In 1987, this compound was described as "the most potent ocular hypotensive agent ever reported." [See, for example, Bito, L. Z., Arch. Ophthalmol. 105, 1036 (1987), and Siebold et al., Prodrug 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular PGF2α and its prodrugs, e.g. its 1-isopropyl ester, in humans. The clinical potential of prostaglandins in the management of conditions associated with increased ocular pressure, e.g. glaucoma, has been limited by these side effects.

Certain prostaglandins and their analogs and derivatives, such as the $PGF2_\alpha$ derivative latanoprost, sold under the trademark Xalatan®, have been established as compounds useful in treating ocular hypertension and glaucoma. However, latanoprost, the first prostaglandin approved by the United States Food And Drug Administration for this indication, is a prostaglandin derivative possessing the undesirable side effect of producing an increase in brown pigment in the iris of 5-15% of human eyes. The change in color results from an increased number of melanosomes (pigment granules) within iridial melanocytes. See e.g., Watson et al., OPHTHALMOLOGY 103:126 (1996). While it is still unclear whether this effect has additional and deleterious clinical ramifications, from a cosmetic standpoint alone such side effects are usually undesirable.

Certain phenyl and phenoxy mono, tri and tetra prostaglandins and their 1-esters are disclosed in European Patent Application 0,364,417 as useful in the treatment of glaucoma or ocular hypertension.

In a series of U.S. patent applications assigned to Allergan, Inc. prostaglandin esters with increased ocular hypotensive activity accompanied with no or substantially reduced side-effects are disclosed. U.S. patent Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl PGF2α. Intraocular pressure reducing 15-acyl prostaglandins are disclosed in U.S. Ser. No. 357,394 (filed May 25, 1989). Similarly, 11,15-9,15- and 9,11-diesters of prostaglandins, for example 11,15-dipivaloyl PGF2α are known to have ocular hypotensive activity. See U.S. Pat. No. 4,494, 274; U.S. patent Ser. No. 584,370, and U.S. Pat. No. 5,034, 413; the parent applications were filed on Jul. 27, 1989.

Woodward et al U.S. Pat. Nos. 5,688,819 and 6,403,649 disclose certain cyclopentane heptanoic acid, 2-cycloalkyl or arylalkyl compounds as ocular hypotensives. These compounds, which can properly be characterized as hypotensive lipids, are effective in treating ocular hypertension.

As one example, the prostamide, bimatoprost, has been discovered to be effective in reducing intraocular pressure possibly by increasing the aqueous humour outflow of an eye (Woodward et al., AGN 2024 (Lumigan®): A Synthetic Prostamide Analog that Lowers Primate Intraocular Pressure by Virtue of Its Inherent Pharmacological Activity, ARVO 2002; (CD-ROM):POS; Chen et al., Lumigan®: A Novel Drug for Glaucoma Therapy, OPTOM IN PRACT, 3:95-102 (2002); Coleman et al., A 3-Month Randomized Controlled Trial of Bimatoprost (LUMIGAN) versus Combined Timolol and Dorzolamide (Cosopt) in Patients with Glaucoma or Ocular Hypertension, OPHTHALMOLOGY 110(12): 2362-8 (2003); Brubaker, Mechanism of Action of Bimatoprost (Lumigan™), SURV OPHTHALMOL 45 (Suppl 4):S347-S351 (2001);

and Woodward et al., The Pharmacology of Bimatoprost (Lumigan™), SURV OPHTHALMOL 45 (Suppl 4) S337-S345 (2001).

Bimatoprost is a structural derivative of a naturally occurring prostamide. Bimatoprost's chemical name is (Z)-7-[(1R, 2R,3R,5S)-3,5-Dihydroxy-2-[1E,3S)-3-hydroxy-5-phenyl-1-pentenyl]cyclopentyl]-5-N-ethylheptenamide, and it has a molecular weight of 415.58. Its molecular formula is $C_{25}H_{37}NO_4$. Bimatoprost is available in a topical ophthalmic solution under the tradename Lumigan® (Allergan, Inc.). Each mL of the solution contains 0.3 mg of bimatoprost as the active agent, 0.05 mg of benzalkonium chloride (BAK) as a preservative, and sodium chloride, sodium phosphate, dibasic; citric acid; and purified water as inactive agents.

In addition to latanoprost and bimatoprost, unoprostone is another example of a currently marketed prostaglandin inhibitors. Other prostaglandin inhibitors may be utilized in alternative embodiments.

Combinations of antiglaucoma drugs or intraocular pressure reducing agents may also be used in embodiments of the present invention.

It is commonly thought that drug combinations that act on different receptor sites or enzymes and that have different modes of action are preferred. Table 3 of the Mathebula reference provides a matrix of classes of antiglaucoma drugs showing some classes of antiglaucoma drugs that can have an additive or synergistic effect on one another compared to the use of a single class of antiglaucoma drugs.

As an example, beta blockers, which lower aqueous humor production, can be combined with miotics, which enhance aqueous trabecular outflow.

As another example, the beta blocker betaxolol can be combined with the sympathomimetics epinephrine or dipivefrin. The combination results in a significant reduction in intraocular pressure due to increased outflow of fluid from the eye.

Timolol may be used in combination with dorzolamide, brimonidine or latanoprost. Other combinations of antiglaucoma drugs may be utilized in other embodiments.

In an embodiment of the present invention, an ocular implant can comprise a steroid and an auxiliary agent, wherein said auxiliary agent comprises an antiglaucoma drug.

In another embodiment, a first ocular implant can comprise a steroid, and a second ocular implant can comprise an auxiliary agent comprising an antiglaucoma drug.

In yet another embodiment, mixtures of implants may be utilized, where the mixture of implants may be selected from the group consisting of an implant that comprises a steroid, an implant that comprises an antiglaucoma drug, an implant that comprises a mixture of a steroid and an antiglaucoma drug, and mixtures thereof.

The steroid may, without limitation, be selected from the group consisting of dexamethasone, fluocinolone, fluocinolone acetonide, triamcinolone, triamcinolone acetonide, beclomethasone, beclomethasone dipropionate, and mixtures thereof. Other steroids may be utilized in other embodiments.

It will be understood that the antiglaucoma drugs discussed herein comprise a specific example of an auxiliary agent.

In this embodiment of the invention the antiglaucoma drug (auxiliary agent) may, without limitation, be selected from the group consisting of a parasympathomimetic, a sympathomimetic, an alpha agonist, a beta blocker, a carbonic anhydrase inhibitor, a prostaglandin analog, an ocular neuroprotectant, and mixtures thereof. Other types of antiglaucoma drugs may be utilized in other embodiments.

The antiglaucoma drug may, without limitation, also be selected from the group consisting of pilocarpine, carbachol, echothiophate, epinephrine, dipivefrin, apraclonidine, timolol, levobunolol, metipranolol, carteolol, betaxolol, dorzolamine, brinzolamide, dichlorphenamide, latanoprost, bimatoprost, unoprostone, apraclonidine, clonidine, p-aminoclonidine, oxymetazoline, norepinephrine, cirazoline, dexmedetomidine, mivazerol, xylazine, medetomidine, and brimonidine and mixtures thereof. Other antiglaucoma drugs may also be suitable.

The ocular implants according to these embodiments of the present invention may comprise any of the polymeric matrices, geometric configurations, or other embodiments of implants that were previously described for ocular implants that comprise steroids.

In some embodiments, an implant that comprises a steroid and an antiglaucoma drug may comprise a first polymeric matrix that may be associated with the steroid and a second polymeric matrix that may be associated with the antiglaucoma drug. The first polymeric matrix may be the same as the second polymeric matrix, or the first polymeric matrix may be different than the second polymeric matrix.

Similarly, in an embodiment where a first implant comprises a steroid, and a second implant comprises an antiglaucoma drug, the first implant and the second implant may comprise the same polymeric matrix, or the first implant and the second implant may comprise different polymeric matrices.

The rate of release and the timing of release of the steroid and the antiglaucoma drug from the implant or implants may be optimized, for example, by adjusting the amounts and types of the polymeric formulations that form the polymeric matrices of the implant or implants.

In some embodiments, the implant comprising the steroid, the antiglaucoma drug, or both the steroid and the antiglaucoma drug may comprise at least one layer or coating covering a core region of the implant. In some embodiments, the covering may comprise a plurality of openings or holes through which the steroid, the antiglaucoma drug, or both the steroid and the antiglaucoma drug may pass to an external environment, for example to the ocular region of the eye.

The properties of the coating and the size or number of openings or holes in the coating may be adjusted to provide optimum delivery of the steroid and antiglaucoma drug.

The timing and the duration of release of the steroid and antiglaucoma drug may therefore be adjusted, for example, by changing the formulation of the polymeric matrix and/or the configuration of the implant or implants.

In some embodiments, the steroid may be released from the implant or implants simultaneously with the release of the antiglaucoma drug from the implant.

In other embodiments, the antiglaucoma drug may be released from the implant or implants at a different time than a time when the steroid is released.

For example, in some embodiments, the antiglaucoma drug may be released from the implant or implants before the steroid is released. In other embodiments, the antiglaucoma drug may be released from the implant or implants after the steroid is released.

In still other embodiment, the release of the steroid may be pulsed or otherwise varied while the antiglaucoma drug is delivered at a substantially constant rate by comparison over the same time period.

The relative effectiveness of releasing the steroid and antiglaucoma drug simultaneously or at different times may depend on the steroid, the antiglaucoma drug, the patient, the formulation of the polymeric matrix of the implant, the configuration of the implant, or many other factors.

In an embodiment in which the antiglaucoma drug is released from the implant before the steroid is released from the implant, the antiglaucoma drug that is already present when the steroid is released may sometimes be more effective in counteracting any increase in intraocular pressure that may be induced by the release of the steroid than if the antiglaucoma drug were released after the steroid is released.

In an alternative embodiment in which the antiglaucoma drug is released from the implant at a later time than the steroid, some antiglaucoma drugs may be effective at rapidly reducing the increase in intraocular pressure that may be caused by the prior release of the steroid from the implant. For example, as previously discussed, carbonic anhydrase inhibitors can rapidly reduce the intraocular pressure. Releasing a carbonic anhydrase inhibitor antiglaucoma drug after releasing the steroid may sometimes be an effective treatment for ocular diseases.

The steroid and the antiglaucoma drug may also be released from the implant or implants continuously or intermittently. Continuous or intermittent release of the steroid and the antiglaucoma drug may both be effective.

For example, if the steroid and the antiglaucoma drug are released continuously, the continuous release of the antiglaucoma drug may mitigate any increase in the intraocular pressure that may be caused by the continuous release of the steroid.

In an embodiment in which the steroid and the antiglaucoma drug may be released intermittently, halting the release of the steroid may allow the intraocular pressure in the eye to decline to a lower pressure. Releasing the antiglaucoma drug from the implant after the ocular pressure has declined somewhat after the release of the steroid has been halted may sometimes enhance the effectiveness of the antiglaucoma drug in lowering the ocular pressure in the eye.

In another embodiment, the steroid may be released from the implant continuously, and the antiglaucoma drug may be released intermittently. An intermittent release of the antiglaucoma drug may optimize the reduction of the intraocular pressure that may have been increased by the release of the steroid.

In some embodiments, the steroid and the antiglaucoma drug may be released alternately. For example, a pulse of steroid may be followed by a pulse of antiglaucoma drug, followed in turn by another pulse of steroid.

In some instances, the concentration of steroid in the vitreous fluid may be at a higher level when an implant comprising steroid is first contacted with the vitreous fluid in the eye than at later times. The "spike" in the concentration of steroid in the vitreous fluid when the implant is first introduced into the eye could potentially lead to a corresponding spike in the ocular pressure in the eye. The spike in ocular pressure may increase the likelihood that a patient could develop glaucoma. It may therefore be advantageous to avoid high levels of steroid in the vitreous fluid of the patient when the implant is introduced into the eye of the patient.

Further, a patient may be more likely to develop glaucoma if the vitreous fluid of the patient continuously contains steroid for an extended period of time than if the vitreous fluid contains high levels of steroid for only a short period of time. The time that the steroid may be present in the vitreous fluid in the eye of the patient continuously without having the patient having an increased risk of developing glaucoma may vary from patient to patient. Generally, exposing the vitreous fluid in an eye of a patient to steroid continuously for approximately six months or more may lead to increased rates of glaucoma. It may therefore be advantageous to avoid continuously releasing steroid into the vitreous fluid for extended periods of time of, for example, six months or more.

The relative timing and the length of time of release of the steroid and the antiglaucoma drug may be varied, for example, by varying the formulation of the polymeric matrix and/or the configuration of the implant or implants. The following examples are illustrative only and are not meant to be limiting.

For example, the implant may comprise a first polymeric formulation associated with a steroid, where the first polymeric formulation may release the steroid at a relatively rapid rate. The implant may also comprise a second polymeric formulation that is associated with an antiglaucoma drug, where the second polymeric formulation may release the antiglaucoma drug at a slower rate than the rate at which the steroid is released from the first polymeric formulation. The slower rate of release of the antiglaucoma drug from the second polymeric formulation may provide a longer period of time of protection in which the intraocular pressure may be lowered by the presence of the antiglaucoma drug.

In another embodiment, the implant may comprise a steroid in an exterior portion of the polymeric formulation and an antiglaucoma drug in an interior portion of the polymeric formulation. The steroid in the exterior portion of the polymer may be released quickly, and the antiglaucoma drug on the interior portion of the polymer may be released at a later time. Releasing the antiglaucoma drug after the steroid is released may aid in lowering any increase in intraocular pressure due to release of the steroid.

The implant may be configured to release steroid and antiglaucoma drug alternately in different ways. For example, an ocular implant may comprise alternating layers of steroid and antiglaucoma drug such that the steroid and the antiglaucoma drug may be released from the implant on an alternating basis.

The polymeric formulation or configuration of the implant comprising steroid may also be designed to avoid high initial levels of steroid in the vitreous fluid. For example, the polymer of the implant may be designed to have small pores. The small pores may slow the release of the steroid from the implant, mitigating the "spike" in the initial steroid concentration. In an alternative embodiment, the implant may comprise an impermeable coating having a plurality of holes in the coating, where the size of the plurality of holes may be relatively small. Other ways to avoid high initial levels of steroid will be apparent to those skilled in the art.

The manner and timing of the release of the steroid and the antiglaucoma drug (or auxiliary agent) may therefore be optimized by changing the formulation of the polymeric matrix and/or the configuration of the implant or implants. The optimal configurations and formulations for the implant or implants may depend on the quantities and types of the steroid and the antiglaucoma drug.

A method for treating ocular diseases in a patient comprises contacting an implant comprising a steroid and an implant comprising an antiglaucoma drug with the vitreous fluid in the eye of the patient. The implant comprising the antiglaucoma drug may be the same or different than the implant comprising the steroid. Contacting the implant comprising the steroid with the vitreous fluid may release a therapeutic amount of steroid into the vitreous fluid. Contacting the implant comprising the antiglaucoma drug with the vitreous fluid may release a therapeutic amount of antiglaucoma drug into the vitreous fluid.

Releasing the steroid into the vitreous fluid may sometimes increase the intraocular pressure in the eye of the patient. An increase in the intraocular pressure could increase the likelihood of the patient developing complications such as glaucoma.

Releasing antiglaucoma drug into the vitreous fluid from the implant comprising the antiglaucoma drug may lessen any increase in intraocular pressure that may be caused by releasing the steroid into the vitreous fluid.

The method may further comprise providing implants or mixtures of implants having configurations and formulations as previously described.

EXAMPLES

The following non-limiting examples provide those of ordinary skill in the art with specific preferred drug delivery systems, methods of making such systems, and methods to treat conditions within the scope of the present invention. The following examples are not intended to limit the scope of the invention.

Example 1

Manufacture and Testing of Implants Containing Fluocinolone and a Biodegradable Polymer Matrix Fluocinolone acetonide was combined with a polymer in a stainless steel mortar and mixed using the Turbula shaker set at 96 RPM for 15 minutes. The powder of the fluocinolone and polymer was scraped off the walls of the steel mortar and then mixed again for an additional 15 minutes. The powder blend was heated at temperatures ranging from 110° C. to 160° C., depending on the polymer used, for a total of 30 minutes, forming a polymer/drug melt. The melt was pelletized, then loaded into the barrel and extruded into filaments, and finally the filaments were cut into about 0.5 mg or about 1 mg size implants. The implants had a weight range from about 450 µg to about 550 µg, or from about 900 µg to about 1100 µg. The 1 mg size implants had a length of about 2 mm and a diameter of about 0.72 mm.

Each implant was placed in a 20 ml screw cap vial with 10 ml of 0.9% saline. The vials were placed in a shaking water bath at 37° C. 9 ml aliquots were removed and replaced with equal volume of fresh media on day 1, 4, 7 and every week thereafter. The in-vitro release testing was performed on each lot of implants in six replicates.

The drug assays were performed by HPLC, consisting of a Waters 2690 Separation Module (or 2696) and Waters 2996 Photodiode Array Detector. A Varian Microsorb-MV™ 100 Å C18 column was used for separation and the detector was set at 254 nm. The mobile phase was (50:50) acetonitrile/0.005M sodium acetate (pH=4.0). The flow rate was 1.00 ml/min and the total run time for was 6 minutes. The release rate was determined by calculating the amount of drug released in a given volume of medium over time in µg/day.

A total of 20 fluocinolone acetonide formulations were prepared, as shown in Table 1. The polymers used were Boehringer Ingelheim Resomers RG755, RG503, R202H, RG502H, and RG502. The inherent viscosities were about 0.6, 0.4, 0.2, 0.2, and 0.2 dl/g, respectively. The average molecular weights were 40000, 28300, 6500, 8400, and 11400 daltons, respectively.

TABLE 1

| | | | | | | | |
|---|---|---|---|---|---|---|---|
| Fluocinolone Acetonide Formulations | | | | | | | |
| Formulation | Lot | FA (w/w) | Polymer | I.V. (dl/g) | Melt T | Extru T (core) | Nozzle | DDS Size |
| 1 | 453-98A | 40% | RG755 | 0.6 | 160° C. | 122° C. | 380 µm | 0.5 mg |
| 2 | 453-98B | 40% | RG755 | 0.6 | 160° C. | 122° C. | 720 µm | 0.5 mg |
| 3 | 453-99 | 20% | RG755 | 0.6 | 160° C. | 116° C. | 720 µm | 1 mg |
| 4 | 453-100 | 40% | RG503 | 0.4 | 150° C. | 116° C. | 720 µm | 0.5 mg |
| 5 | 453-101 | 20% | RG503 | 0.4 | 150° C. | 106° C. | 720 µm | 1 mg |
| 6 | 453-116 | 40% | R202H | 0.2 | 110° C. | 90° C. | 720 µm | 0.5 mg |
| 7 | 453-117 | 40% | RG752 | 0.2 | 110° C. | 90° C. | 720 µm | 0.5 mg |
| 8 | 453-118 | 40% | RG502H | 0.2 | 110° C. | 84° C. | 720 µm | 0.5 mg |
| 9 | 453-119 | 40% | RG502 | 0.2 | 110° C. | 92° C. | 720 µm | 0.5 mg |
| 10 | 453-120 | 40% | (1:1)RG502H/R202H | 0.2 | 110° C. | 85° C. | 720 µm | 0.5 mg |
| 11 | 453-121 | 40% | (1:1)RG502H/RG752 | 0.2 | 110° C. | 83° C. | 720 µm | 0.5 mg |
| 12 | 453-128 | 60% | (3:1)RG502H/R202H | 0.2 | 110° C. | 95° C. | 720 µm | 0.5 mg |
| 13 | 453-129 | 60% | (3:1)RG502H/RG752 | 0.2 | 110° C. | 101° C. | 720 µm | 0.5 mg |
| 14 | 453-130 | 60% | (3:1)RG502H/RG502 | 0.2 | 110° C. | 101° C. | 720 µm | 0.5 mg |
| 15 | 453-131 | 60% | (1:1)RG502H/R202H | 0.2 | 110° C. | 101° C. | 720 µm | 0.5 mg |
| 16 | 453-137 | 40% | (1:2)RG502H/R202H | 0.2 | 110° C. | 88° C. | 720 µm | 1 mg |
| 17 | 453-138 | 40% | (1:2)RG502H/RG752 | 0.2 | 110° C. | 85° C. | 720 µm | 1 mg |
| 18 | 453-139 | 40% | (1:2)RG502H/RG502 | 0.2 | 120° C. | 85° C. | 720 µm | 1 mg |
| 19 | 453-140 | 40% | (1:2)RG502H/RG503 | n.a. | 120° C. | 99° C. | 720 µm | 1 mg |
| 20 | 453-141 | 40% | (1:2)RG502H/RG755 | n.a. | 120° C. | 99° C. | 720 µm | 1 mg |

FA = Fluocinolone Acetonide
I.V. = inherent viscosity
Melt T = melting temperature
Extru T = extrusion temperature
Nozzle = nozzle diameter (µm)
DDS size = drug delivery system size (i.e., the weight of an individual implant)

Figure 2:
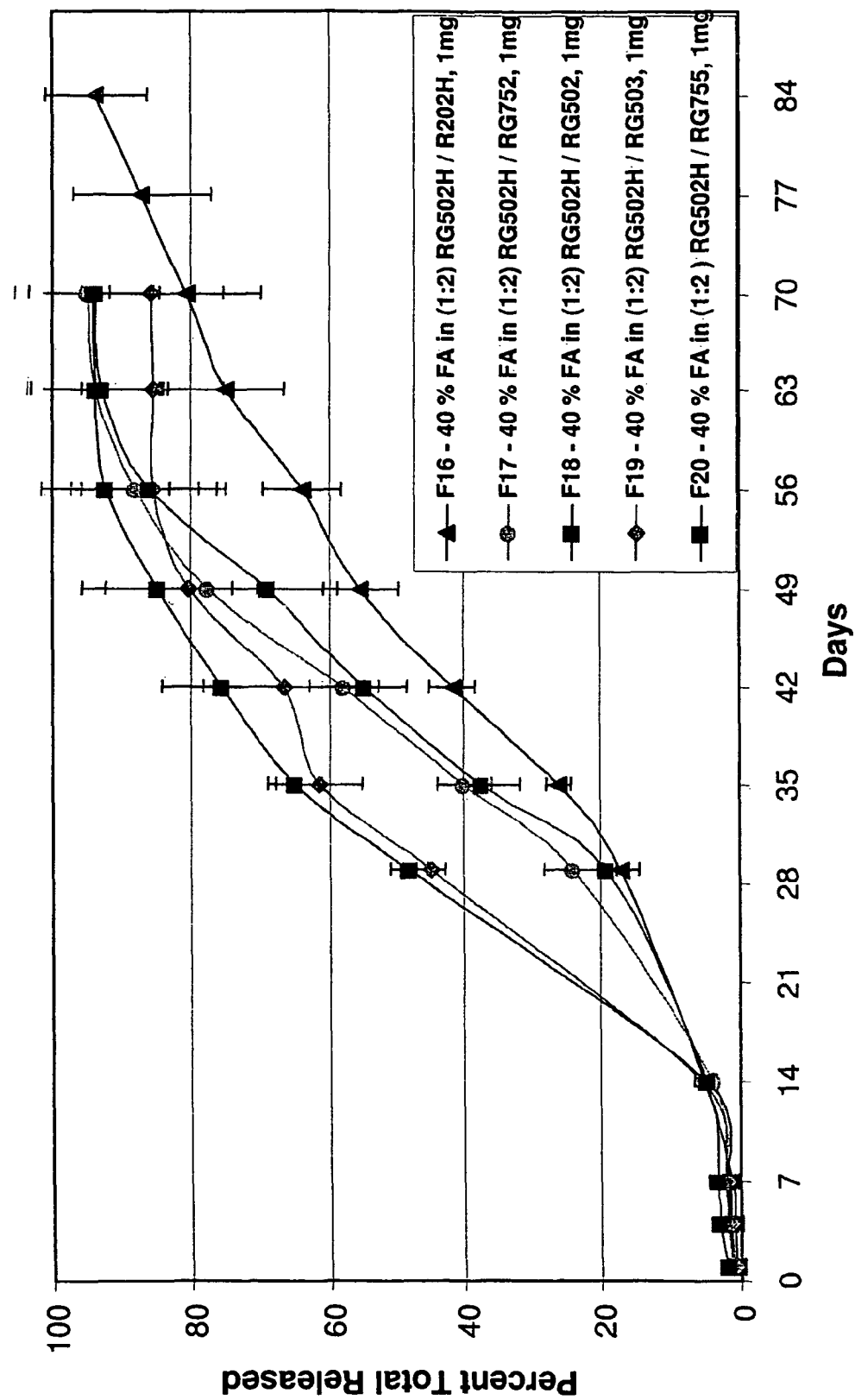
FIG. 2 is a graph similar to FIG. 1 showing the cumulative release profiles for biodegradable fluocinolone acetonide containing implants with different combinations of biodegradable polymers.

Of the 20 formulations prepared, 16 were screened for release testing (formulations #1-11 and 16-20). Initially, the release medium was 10 mL phosphate buffer-saline (PBS) with 1 mL replacement at each time point, but almost no release was observed up to three weeks. The release medium was subsequently changed to PBS with 9 mL replacement, but the release was inconsistent and with unacceptably high standard deviations. Finally, the release medium was switched to 0.9% saline with 9 mL replacement at each time point. The release profiles are shown in FIGS. 1 and 2.

Most of the fluocinolone acetonide formulations released the total drug load in approximately 2-3 months. Of the 16 formulations, 11 formulations exhibited release for about two months. Of the 11 formulations, 6 formulations exhibited release for about three months.

In particular, all formulations prepared with Resomer RG755 (453-98A, 453-98B, and 453-99) and RG752 (453-117) showed almost no release after day 4 and their release studies were stopped after 1 month.

Formulations prepared with RG503 (453-100 and 453-101) and RG502 (453-119) showed a delay of 3-4 weeks before releasing 100% between day 49 and day 56.

The formulation prepared with RG502H (453-118) appeared to be the fastest, on day 49.

The formulation prepared with a (1:1) mixture of RG502H and R202H led to the longest release, up to 84 days.

Finally, the formulation prepared with a (1:1) mixture of RG502H and RG752 appeared to be slower than the one prepared with RG502H (453-118) at first, but eventually ended up having complete release at day 49.

Based on these data, it was concluded that a mixture of RG502H and other polymers with slower release will provide a formulation with longer release and relatively closer to zero-order kinetics. One formulation with desirable release properties was a 1:2 mixture of RG502H and R202H, which led to a release of 94% of the fluocinolone after 84 days.

Example 2

Manufacture and Testing of Implants Containing Triamcinolone and a Biodegradable Polymer Matrix Triamcinolone acetonide was combined with a polymer in a stainless steel mortar and mixed using the Turbula shaker set at 96RPM for 15 minutes. The powder of the fluocinolone and polymer was scraped off the walls of the steel mortar and then mixed again for an additional 15 minutes. The powder blend was heated at temperatures ranging from 110° C. to 160° C., depending on the polymer used, for a total of 30 minutes, forming a polymer/drug melt. The melt was pelletized, then loaded into the barrel and extruded into filaments, and finally the filaments were cut into about 0.5 mg or about 1 mg size implants. The implants had a weight range from about 450 µg to about 550 µg, or from about 900 µg to about 1100 µg. The 1 mg size implants had a length of about 2 mm and a diameter of about 0.72 mm.

The testing of the triamcinolone implants was performed as described in Example 1.

A total of 16 triamcinolone acetonide formulations were prepared, as shown in Table 2. The polymers used were Boehringer Ingelheim Resomers RG755, RG503, R202H, RG502H, and RG502. The inherent viscosities were 0.6, 0.4, 0.2, 0.2, and 0.2 dl/g, respectively. The average molecular weights were 40000, 28300, 6500, 8400, and 11400 daltons, respectively.

TABLE 2

Triamcinolone Acetonide Formulations

| Formulation | Lot | TA (w/w) | Polymer | I.V. (dl/g) | Melt T | Extru T (core) | Nozzle | DDS Size |
|---|---|---|---|---|---|---|---|---|
| 1 | 453-96 | 50% | RG755 | 0.6 | 160° C. | 122° C. | 720 µm | 1 mg |
| 2 | 453-97 | 50% | RG503 | 0.4 | 150° C. | 116° C. | 720 µm | 1 mg |
| 3 | 453-112 | 50% | RG502 | 0.2 | 110° C. | 105° C. | 720 µm | 1 mg |
| 4 | 453-113 | 50% | RG502H | 0.2 | 110° C. | 90° C. | 720 µm | 1 mg |
| 5 | 453-114 | 50% | RG752 | 0.2 | 110° C. | 95° C. | 720 µm | 1 mg |
| 6 | 453-115 | 50% | R202H | 0.2 | 110° C. | 96° C. | 720 µm | 1 mg |
| 7 | 453-122 | 50% | (1:1)RG502H/RG752 | 0.2 | 110° C. | 83° C. | 720 µm | 1 mg |
| 8 | 453-123 | 50% | (1:1)RG502H/R202H | 0.2 | 110° C. | 85° C. | 720 µm | 1 mg |
| 9 | 453-125 | 60% | (3:1)RG502H/RG502 | 0.2 | 110° C. | 92° C. | 720 µm | 1 mg |
| 10 | 453-126 | 60% | (3:1)RG502H/R202H | 0.2 | 110° C. | 92° C. | 720 µm | 1 mg |
| 11 | 453-127 | 60% | (3:1)RG502H/RG752 | 0.2 | 110° C. | 95° C. | 720 µm | 1 mg |
| 12 | 453-132 | 60% | (1:1)RG502H/R202H | 0.2 | 110° C. | 108° C. | 720 µm | 1 mg |
| 13 | 453-133 | 50% | (1:1)RG502H/RG502 | 0.2 | 110° C. | 99° C. | 720 µm | 1 mg |
| 14 | 453-134 | 50% | (1:1)RG502H/RG755 | N/A | 110° C. | 110° C. | 720 µm | 1 mg |
| 15 | 453-135 | 50% | (1:1)RG502H/RG503 | N/A | 110° C. | 110° C. | 720 µm | 1 mg |
| 16 | 453-136 | 50% | (3:1)RG502H/RG502 | 0.2 | 110° C. | 88° C. | 720 µm | 1 mg |

TA = Triamcinolone Acetonide

I.V. = inherent viscosity

Melt T = melting temperature

Extru T = extrusion temperature

Nozzle = nozzle diameter (µm)

DDS size = drug delivery system size (i.e., the weight of an individual implant)

Figure 3:
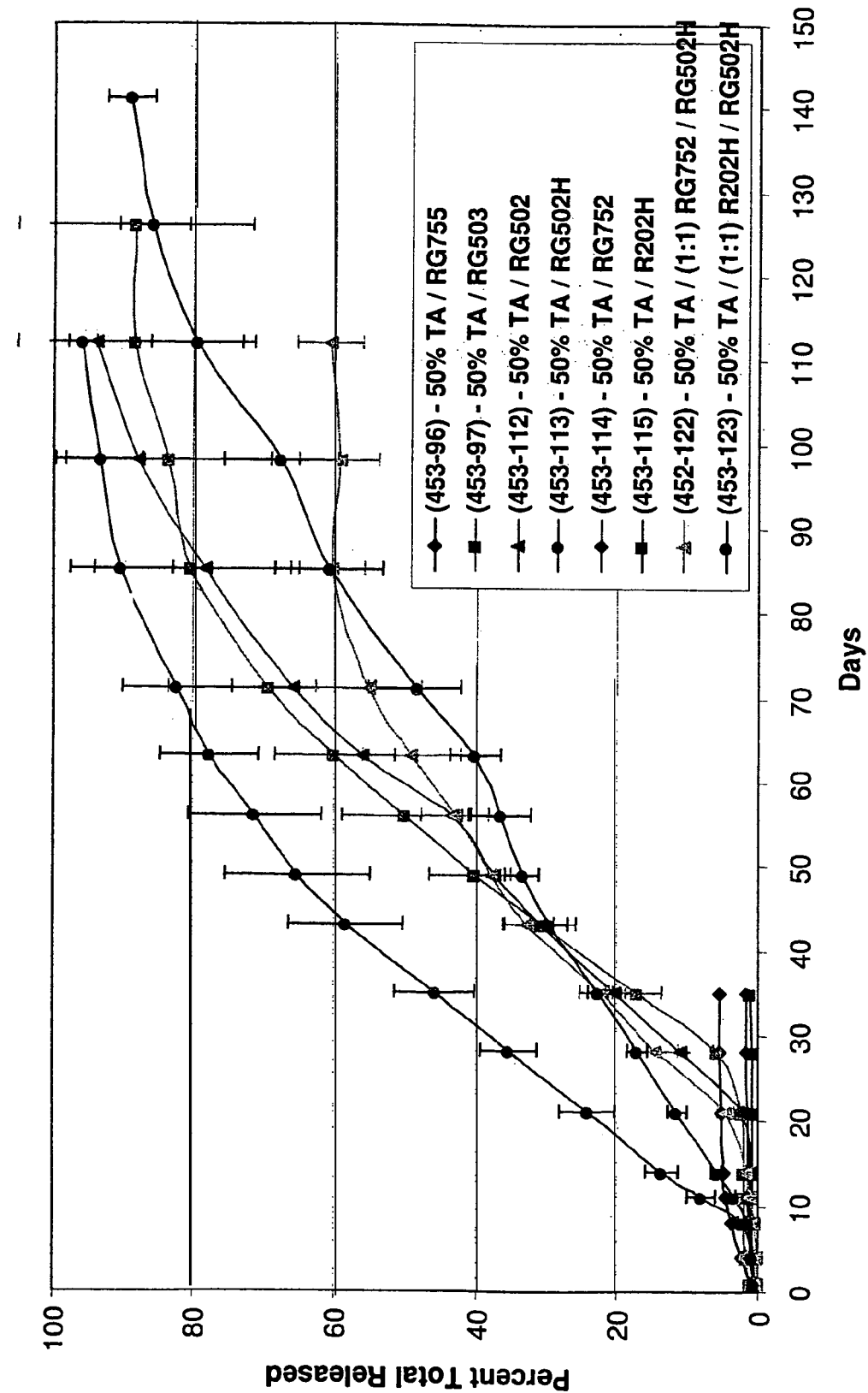
FIG. 3 is a graph similar to FIG. 1 showing the cumulative release profiles for biodegradable triamcinolone acetonide containing implants.
Figure 4:
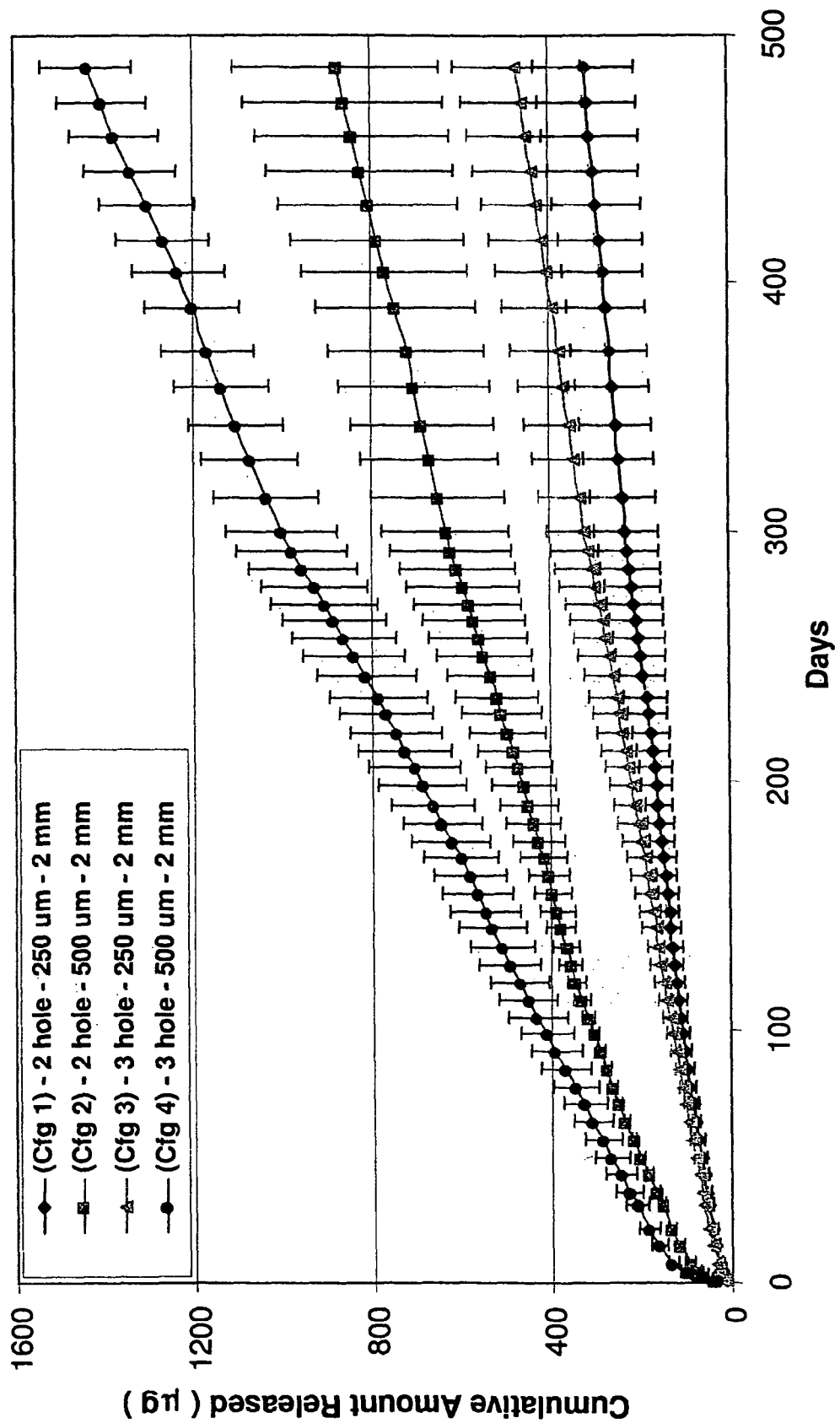
FIG. 4 is a graph showing the cumulative release profiles for non-sterile fluocinolone acetonide containing implants having different hole configurations.
Figure 5:
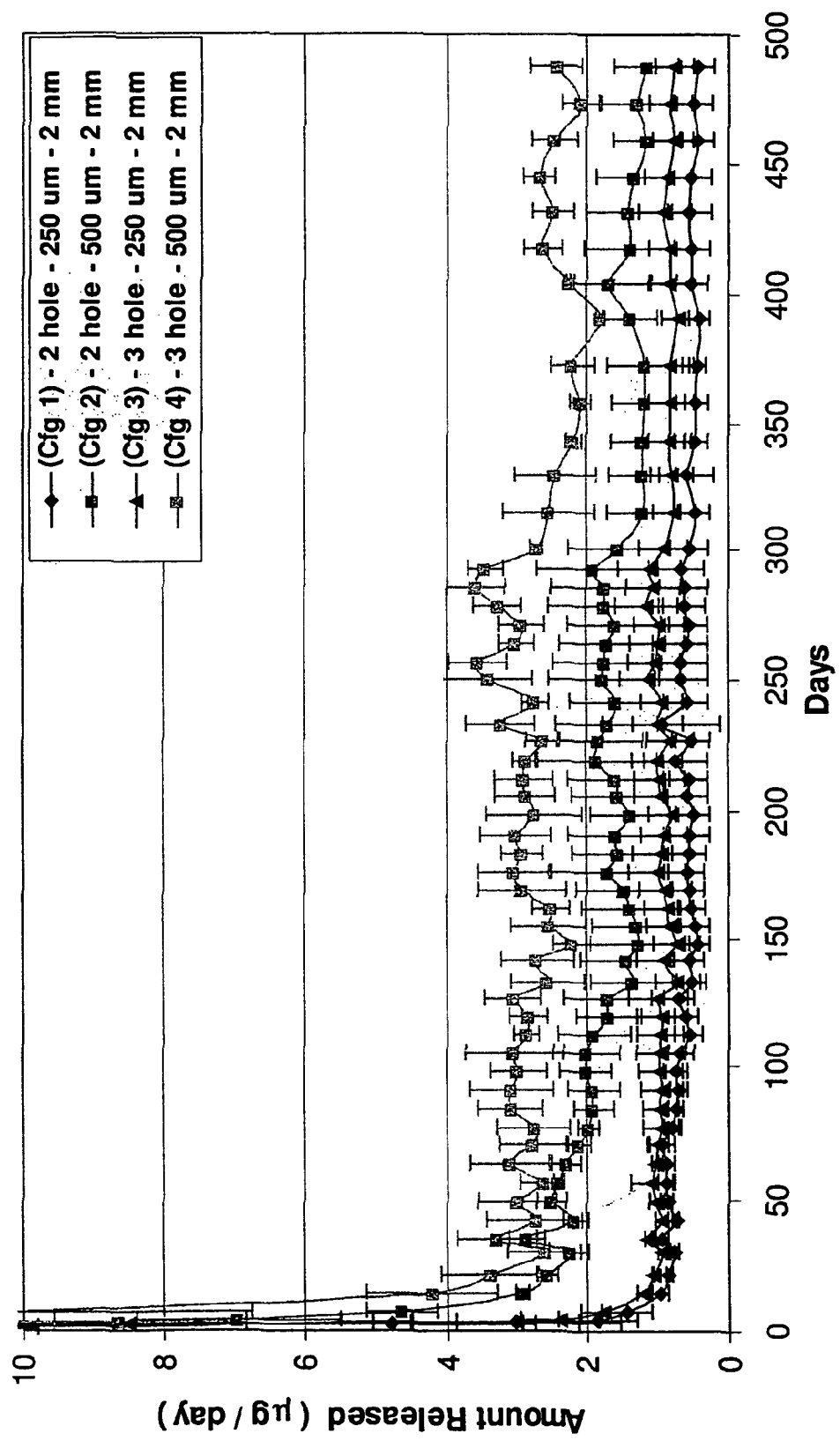
FIG. 5 is a graph showing the amount of fluocinolone released per day for the implants described in FIG. 4.
Figure 6:
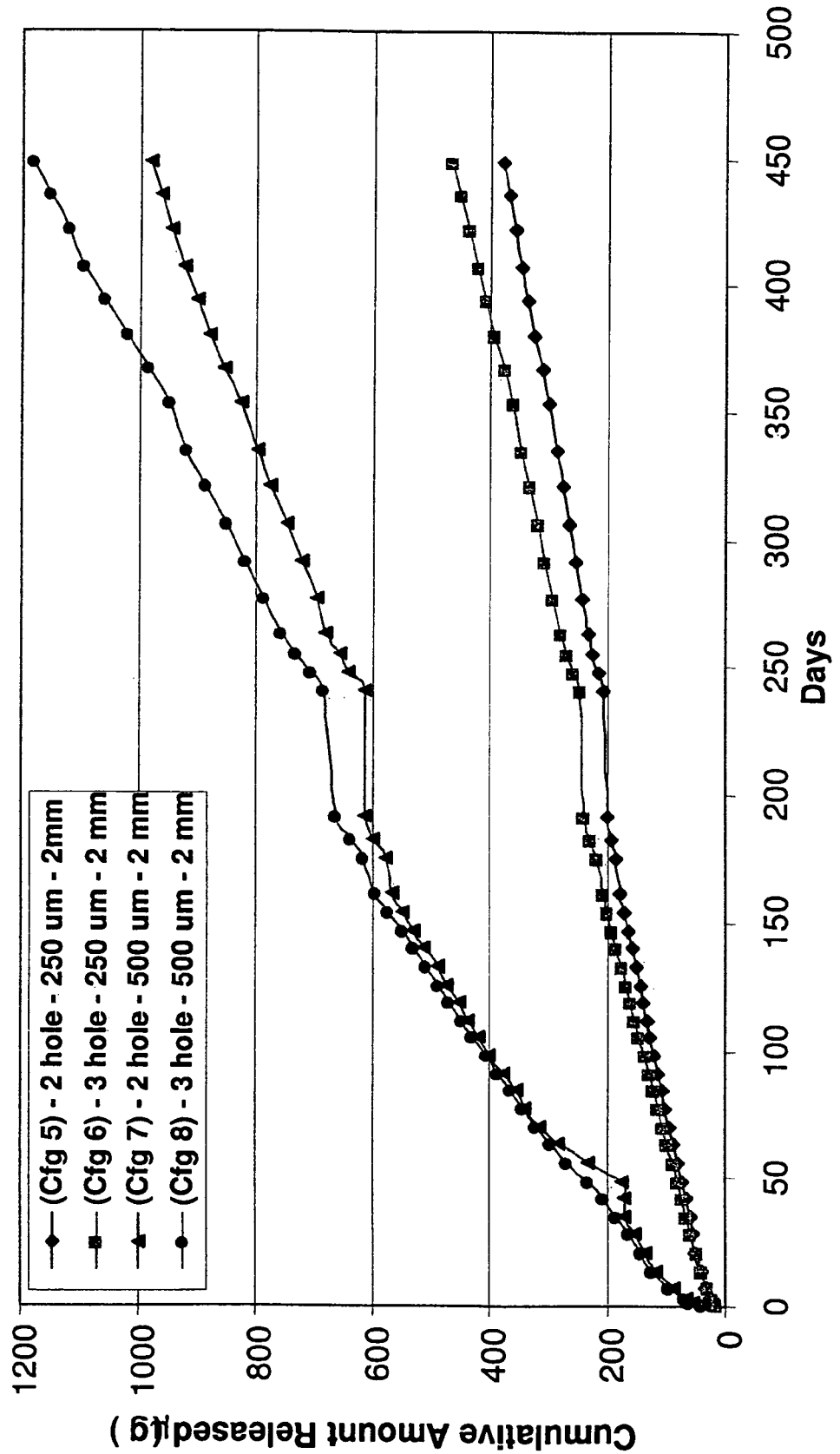
FIG. 6 is a graph showing the cumulative release profiles for sterile fluocinolone acetonide containing implants having different hole configurations.
Figure 7:
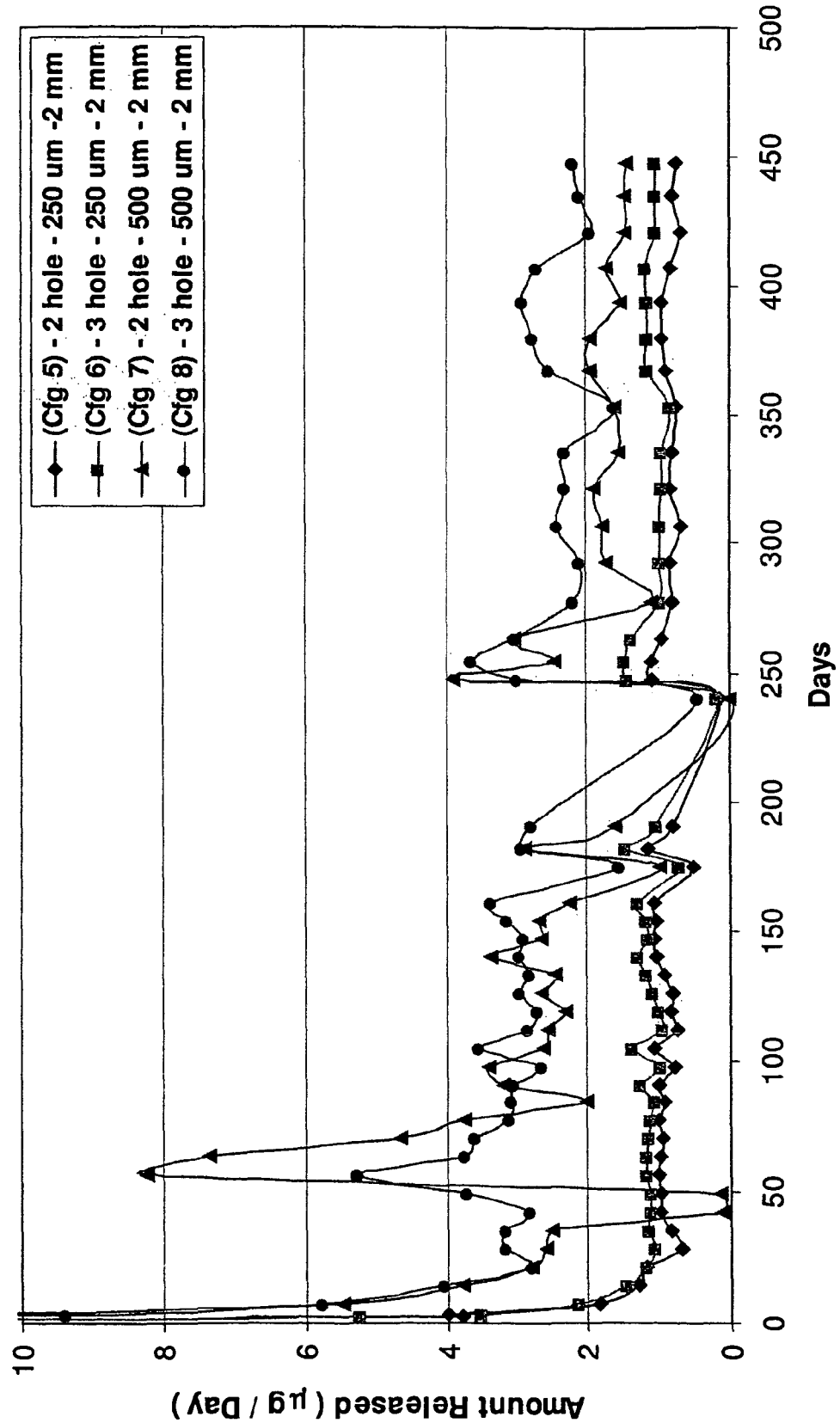
FIG. 7 is a graph showing the amount of fluocinolone released per day for the implants described in FIG. 6.
Figure 8:
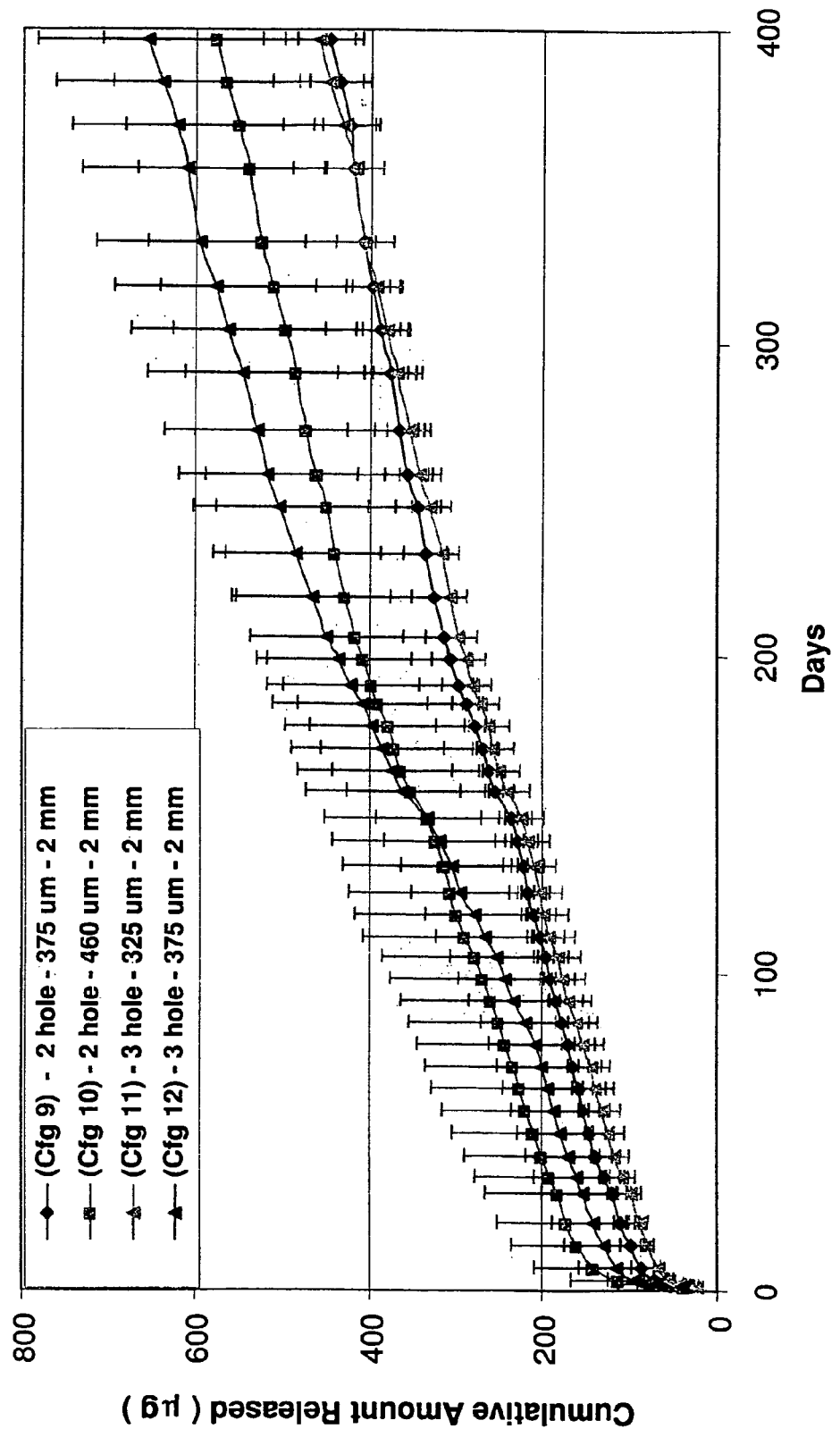
FIG. 8 is a graph showing the cumulative release profiles for non-sterile fluocinolone acetonide containing implants having different hole configurations than those described in FIG. 4.
Figure 9:
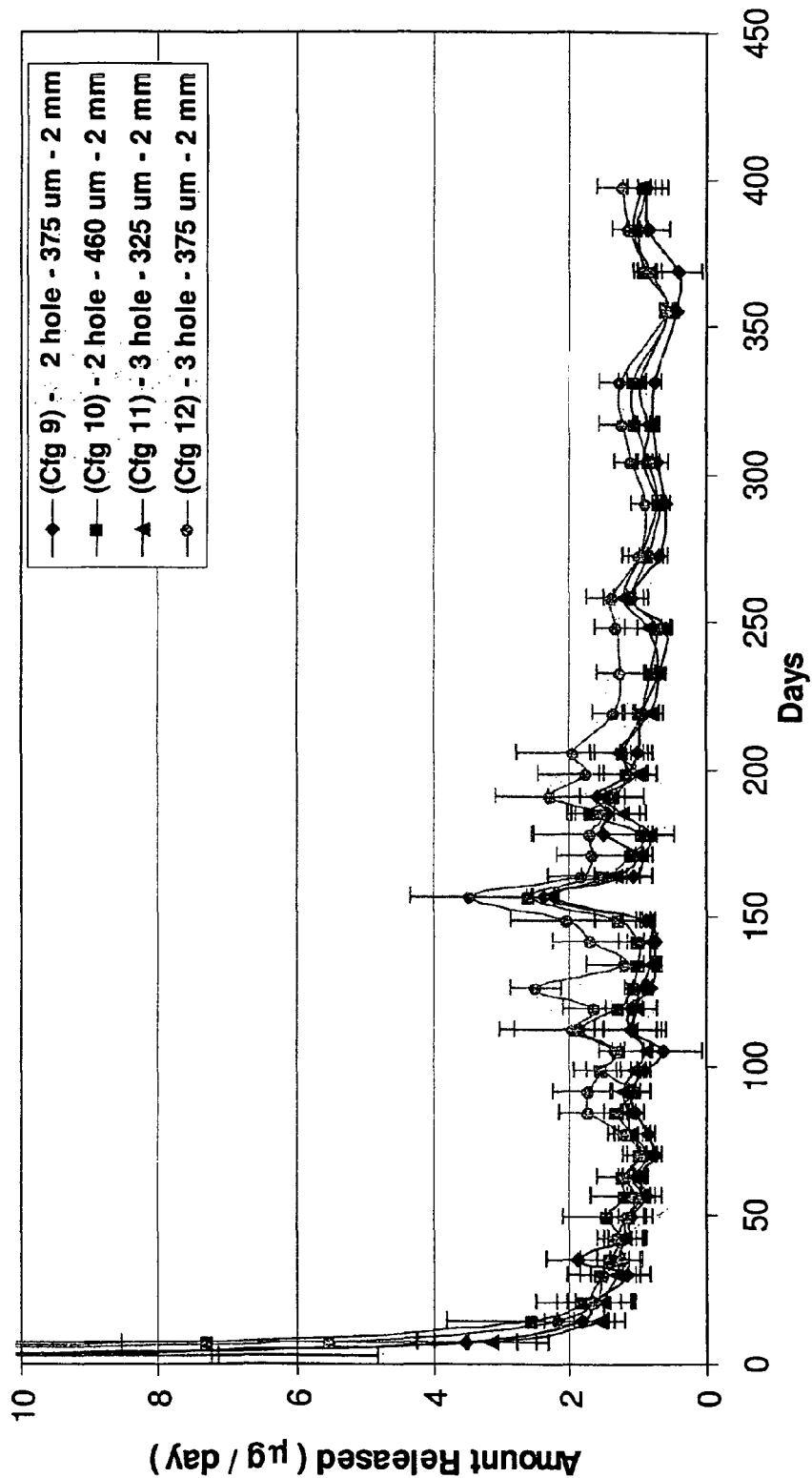
FIG. 9 is a graph showing the amount of fluocinolone released per day for the implants described in FIG. 8.
Figure 10:
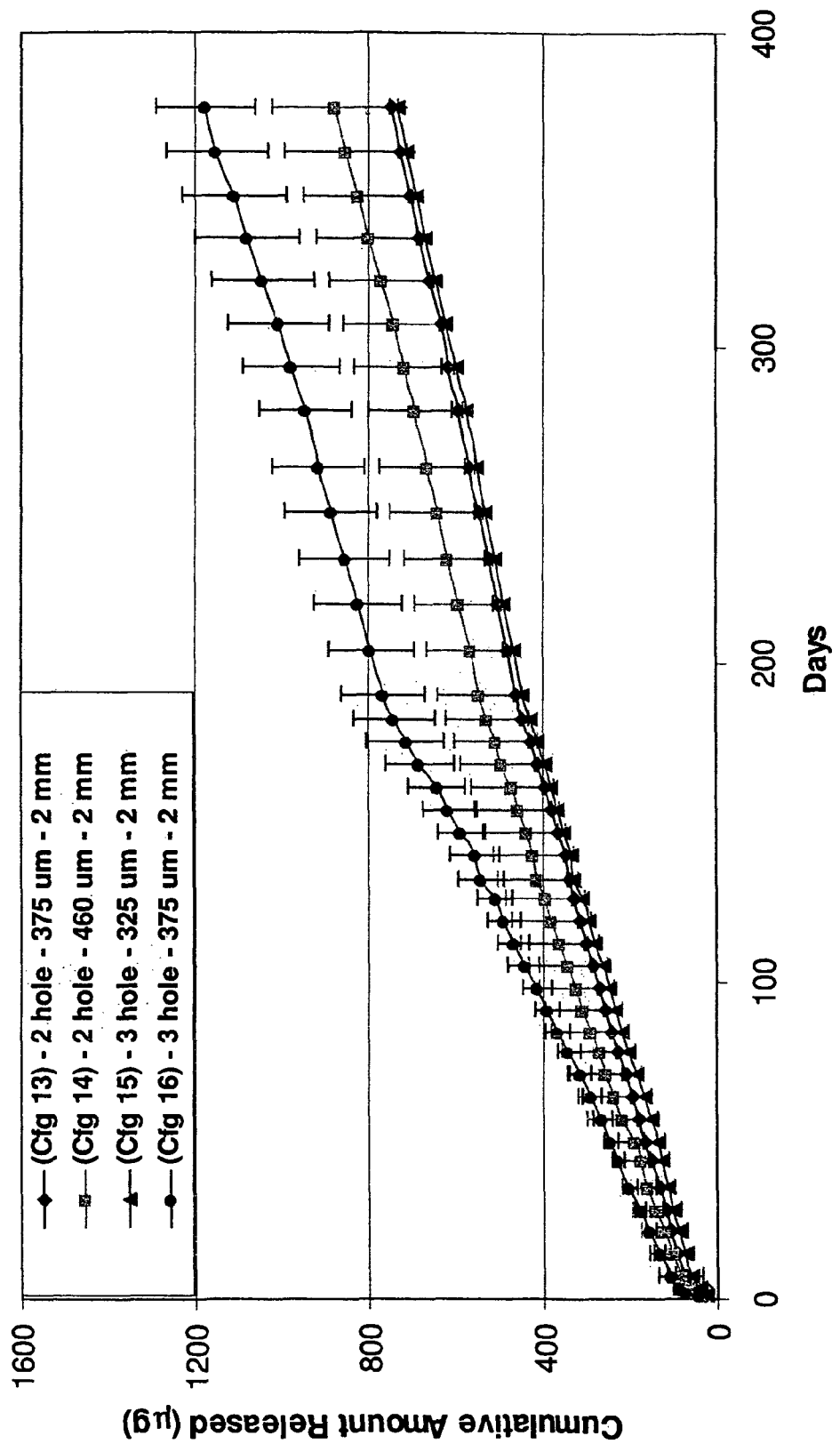
FIG. 10 is a graph showing the cumulative release profiles for sterile fluocinolone acetonide containing implants having hole configurations similar to those described in FIG. 8.
Figure 11:
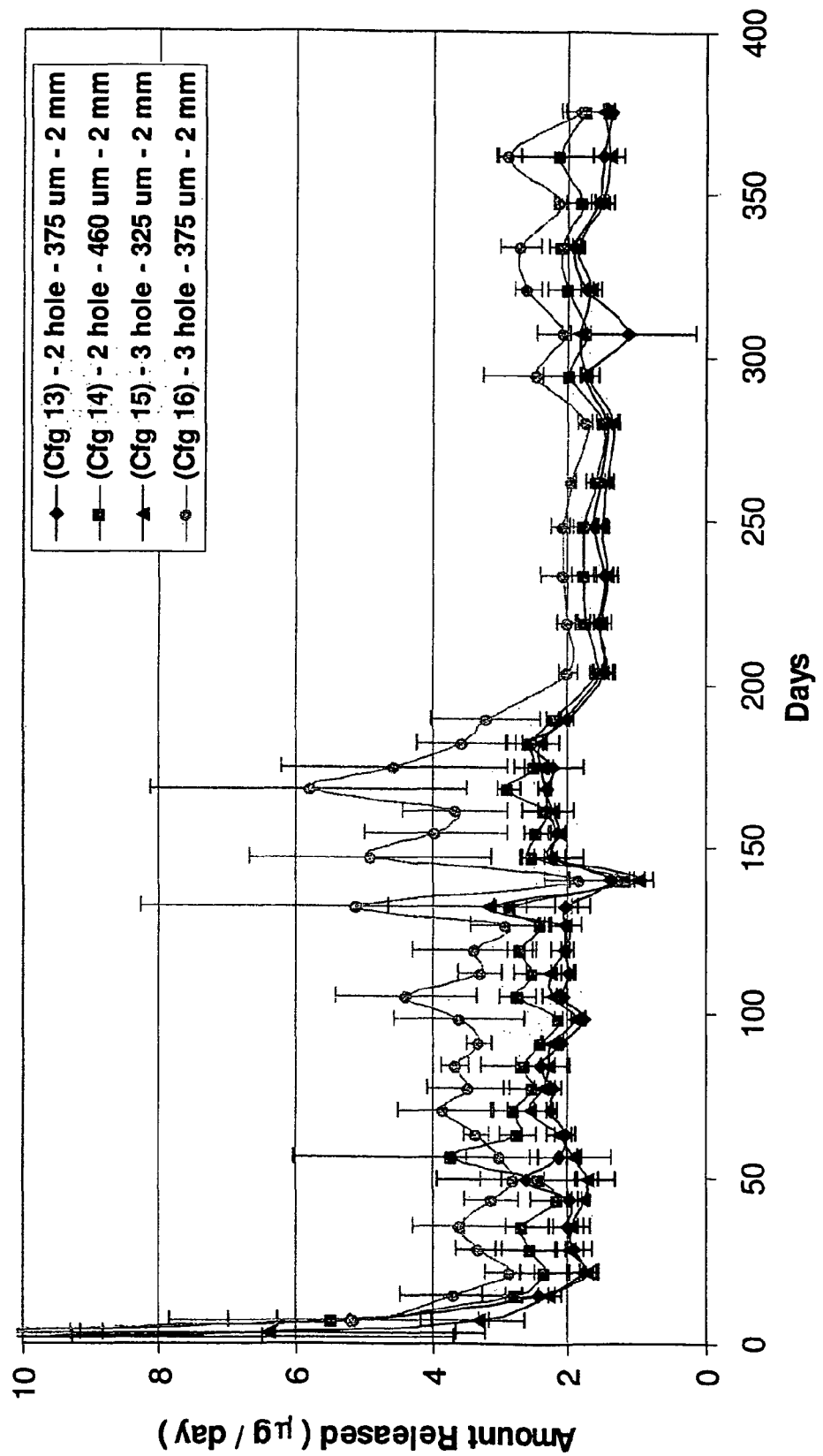
FIG. 11 is a graph showing the amount of fluocinolone released per day for the implants described in FIG. 10.

Of the 16 formulations prepared, 8 were screened for release testing (formulations #1-8). The same problem was encountered with the release medium as that of fluocinolone. The release medium was switched to 0.9% saline with 9 mL replacement at each time point. The release profiles are shown in FIG. 3.

Certain triamcinolone acetonide formulations had release periods of about 4-6 months. Of the eight formulations, five formulations exhibited 4 or more months of release, and two formulations exhibited release for more than 5 months.

Formulations prepared with RG755 (453-96), RG752 (453-114) and R202H (453-115) showed essentially zero to very slow release.

The formulation prepared with RG502H (453-113) had the fastest and perhaps smoothest release profile with minimal delay lasting close to 4 months.

The formulation prepared with RG502 (453-112) showed an equally fast release of 4 months, but there was a 2-3 weeks lag time.

The formulation prepared with RG503 (453-97) showed a release longer than 4 months, but it also had 4 weeks lag time.

Similar to the formulations in Example 1, the formulation prepared with a (1:1) mixture of RG502H and R202H lot (453-123) led to a desirable release profile approaching 5 to 6 months. This release profile was the most linear and the longest (>140 days).

Based on the data of Examples 1 and 2, polymer blends appeared to achieve a more desired controlled release rate relative to single polymers. Using a slow degrading poly(D, L-lactide), such as R202H, and mixing it with a fast degrading poly(D,L-lactide-co-glycolide), such as RG502H, is effective in controlling the release rate of both fluocinolone and triamcinolone acetonide.

Example 3

Manufacture and In Vitro Testing of Implants Containing Fluocinolone and a Polymeric Coating Silicone tubing (Specialty Silicone Fabricators, Inc, SSF-METN-755, P.N. OP-2) was cut to either 10 mm or 7 mm tubes to form an implant element. Holes of various sizes were drilled (Photomachining, Inc) in the cut tubes. The configuration of each tube was characterized by the number of holes, the diameter of holes and the distance between the holes, as well as the tube length and the sterility of the tube. Each drilled tube was glued on one end with silicone adhesive (Nusil Silicone Technology, MED-1511), and dried for 72 hours at ambient temperature and then packed with fluocinolone acetonide. Each of the 10 mm long tube contained 4 to 5 mg of fluocinolone, while each of the 7 mm long tubes contained 2 to 3 mg of fluocinolone. Finally, the other end of each tube was glued and dried for 72 hours. The implants did not include any additional excipients or release modifiers. A total of 30 different tube configurations were tested and are described in Table 3.

TABLE 3

Fluocinolone Reservoir Delivery Technology Configurations

| Configuration | Lot # | # Hole/Diam/Distance | Average Drug Load ($\mu$g) | Before or After $\gamma$ Sterilization | Tube Length | Number of Replicates |
|---|---|---|---|---|---|---|
| 1 | 257-172-1 | 2 hole - 250 $\mu$m - 2 mm | 4526 (n = 3) | BS | 1 cm | 3 |
| 2 | 257-172-4 | 2 hole - 500 $\mu$m - 2 mm | 4667 (n = 3) | BS | 1 cm | 3 |
| 3 | 257-172-7 | 3 hole - 250 $\mu$m - 2 mm | 4508 (n = 3) | BS | 1 cm | 3 |
| 4 | 257-172-10 | 3 hole - 500 $\mu$m - 2 mm | 4437 (n = 3) | BS | 1 cm | 3 |
| 5 | 267-33-1 | 2 hole - 250 $\mu$m - 2 mm | 4699 (n = 1) | AS | 1 cm | 1 |
| 6 | 267-33-2 | 3 hole - 250 $\mu$m - 2 mm | 4536 (n = 1) | AS | 1 cm | 1 |
| 7 | 267-33-3 | 2 hole - 500 $\mu$m - 2 mm | 4457 (n = 1) | AS | 1 cm | 1 |
| 8 | 267-33-4 | 3 hole - 500 $\mu$m - 2 mm | 4214 (n = 1) | AS | 1 cm | 1 |
| 9 | 267-140 | 2 hole - 375 $\mu$m - 2 mm | 5228 (n = 3) | BS | 1 cm | 3 |
| 10 | 267-140 | 2 hole - 460 $\mu$m - 2 mm | 4466 (n = 3) | BS | 1 cm | 3 |
| 11 | 267-140 | 3 hole - 325 $\mu$m - 2 mm | 4867 (n = 3) | BS | 1 cm | 3 |
| 12 | 267-140 | 3 hole - 375 $\mu$m - 2 mm | 4566 (n = 3) | BS | 1 cm | 3 |
| 13 | 285-1AS | 2 hole - 375 $\mu$m - 2 mm | 4663 (n = 3) | AS | 1 cm | 3 |
| 14 | 285-1AS | 2 hole - 460 $\mu$m - 2 mm | 4806 (n = 3) | AS | 1 cm | 3 |
| 15 | 285-1AS | 3 hole - 325 $\mu$m - 2 mm | 5168 (n = 3) | AS | 1 cm | 3 |
| 16 | 285-1AS | 3 hole - 375 $\mu$m - 2 mm | 4981 (n = 3) | AS | 1 cm | 3 |
| 17 | 285-54 | 2 hole - 250 $\mu$m - 2 mm | 2804 (n = 3) | AS | 0.7 cm | 3 |
| 18 | 285-54 | 2 hole - 500 $\mu$m - 2 mm | 2428 (n = 3) | AS | 0.7 cm | 3 |
| 19 | 285-54 | 3 hole - 375 $\mu$m - 2 mm | 3068 (n = 3) | AS | 0.7 cm | 3 |
| 20 | 285-54 | 3 hole - 500 $\mu$m - 2 mm | 2899 (n = 3) | AS | 0.7 cm | 3 |
| 21 | 285-126C | 2 hole - 250 $\mu$m - 1 mm | 2770 (n = 3) | BS | 0.7 cm | 3 |
| 22 | 285-126C | 2 hole - 375 $\mu$m - 1 mm | 2591 (n = 3) | BS | 0.7 cm | 3 |
| 23 | 285-126C | 2 hole - 375 $\mu$m - 2 mm | 3245 (n = 3) | BS | 0.7 cm | 3 |
| 24 | 285-126C | 2 hole - 500 $\mu$m - 1 mm | 2819 (n = 3) | BS | 0.7 cm | 3 |
| 25 | 285-126C | 3 hole - 500 $\mu$m - 1.5 mm | 2955 (n = 3) | BS | 0.7 cm | 3 |
| 26 | 285-126D | 2 hole - 250 $\mu$m - 1 mm | 2615 (n = 3) | AS | 0.7 cm | 3 |
| 27 | 285-126D | 2 hole - 375 $\mu$m - 1 mm | 2970 (n = 3) | AS | 0.7 cm | 3 |
| 28 | 285-126D | 2 hole - 375 $\mu$m - 2 mm | 2932 (n = 3) | AS | 0.7 cm | 3 |
| 29 | 285-126D | 2 hole - 500 $\mu$m - 1 mm | 2619 (n = 3) | AS | 0.7 cm | 3 |
| 30 | 285-126D | 3 hole - 500 $\mu$m - 1.5 mm | 2498 (n = 3) | AS | 0.7 cm | 3 |

Each of the 30 implants was placed into a 5 mL centrifuge vial with cap containing 1 mL of phosphate buffer-saline, pH 7.4 (PBS) at 37° C. Total replacement with equal volume of fresh medium was performed on day 1, 4, 7, 14, 28, and every week thereafter. Drug assay was performed on a Waters HPLC system, which included a 2690 (or 2696) Separation Module, and a 2996 Photodiode Array Detector. A Rainin C18, 4.6×100 mm column was used for separation and detector was set at 254 nm. The mobile phase was (50:50) acetonitrile-0.005M NaOAc/HOAc, pH 4.0 with flow rate of 1 mL/min and a total run time of 10 min per sample. Release rates were determined by calculating the amount of drug being released in a given volume of medium over time and expressed in μg/day. The release testing was performed on all 30 configurations in three replicates, except for configurations #5 to 8, for which only one sample of each was tested.

The implants studied varied in the number of holes (2 or 3), hole sizes (250, 325, 375, 460, or 500 μm), distance between the holes (1 mm, 1.5 mm, or 2 mm), length of the implant (1 cm or 0.7 cm), and before or after gamma sterilization, as presented in Table 3.

In general, all 30 implants exhibited an initial burst of drug release on the first day then tapered off to day 7 or later, and finally gradually settled into an equilibrium release range starting after day 14. The first eight configurations were 1 cm in length with drug load of approximately 4.5 mg±0.2 mg in each device, as shown in Table 3. Configurations 1 through 4 were non-sterile, while configurations 5 through 8 were sterile. The cumulative amount released (μg) as a function of time and the amount of release (μg) per day as a function of time are presented in FIGS. 4 through 7.

Configuration #1 (2 hole—250 μm), #2 (2 hole—500 μm), #3 (3 hole—250 μm), and #4 (3 hole—500 μm) gave an average release of 0.63±0.23, 1.72±0.52, 0.94±0.30, and 2.82 μg/day±0.41 μg/day, respectively from day 14 to day 487. These results were compared to their sterile counterparts, configuration #5, #6, #7, and #8, which gave an average release of 0.88, 1.10, 2.48, and 2.84 μg/day, respectively from day 14 to day 448. A good correlation between the number of holes in a configuration and its average daily release was observed for the first four configurations. For example, configuration #3 has 3 holes and configuration #1 has two holes of the same diameter as #3, and configuration #3 released 1½ times more fluocinolone per day than configuration #1. Similar results were obtained with configuration #4 and configuration #2.

In configuration #5 (2 hole—250 μm), #6 (2 hole—500 μm), #7 (3 hole—250 μm), and #8 (3 hole—500 μm), we see approximately a three fold increase in the release rates between configuration #7 and #5, and also between configuration #8 and #6. This was a two-fold increase comparing to the non-sterile counterparts. Configuration #5 (2 holes—250 μm) released an average of 1 μg/day, and configuration #7 (2 holes—500 μm) released an average of 3 μg/day.

Configurations #9 (2 hole—375 μm), #10 (2 hole—460 μm), #11 (3 hole—325 μm), and #12 (3 hole—375 μm) were made and were non-sterile, while configurations 13 through 16 were the sterile counterparts. The cumulative amount released (μg) as a function of time and the amount of release (μg) per day as a function of time are presented in FIGS. 8 through 11. Results from day 14 to day 397 showed an average release of 1.02±0.25, 1.22±0.29, 1.06±0.21, and 1.50±0.39 μg/day for configurations 9, 10, 11, and 12, respectively. Similarly, the data for configurations 13, 14, 15, and 16, which were the sterile counterparts, showed an average release of 1.92±0.23, 2.29±0.33, 1.94±0.18, and 3.15±0.64 μg/day, respectively. Each of the sterile configurations appeared to be releasing twice as fast as its non-sterile counterpart.

Configuration #13 (2 hole—375 μm-2 mm apart) exhibited an average release of 1.92±0.23 μg/day from day 14 through day 376. Likewise, configuration #15 (3 hole—325 μm-2 mm apart) achieved an average release of 1.94±0.18 μg/day from day 14 through day 376. In the same period of time, configurations #14 and #16 achieved an average release of 2.29 μg±0.33 μg/day and 3.15 μg±0.64 μg/day, respectively. Furthermore, configurations #13 and #15 achieved a total release of 16.02%±0.78% and 14.22%±1.13%, respectively, after 376 days. Based on the release rate, the predicted life span of configurations #13 and #15 are 6.4 and 7.24 years, respectively.

Figure 12:
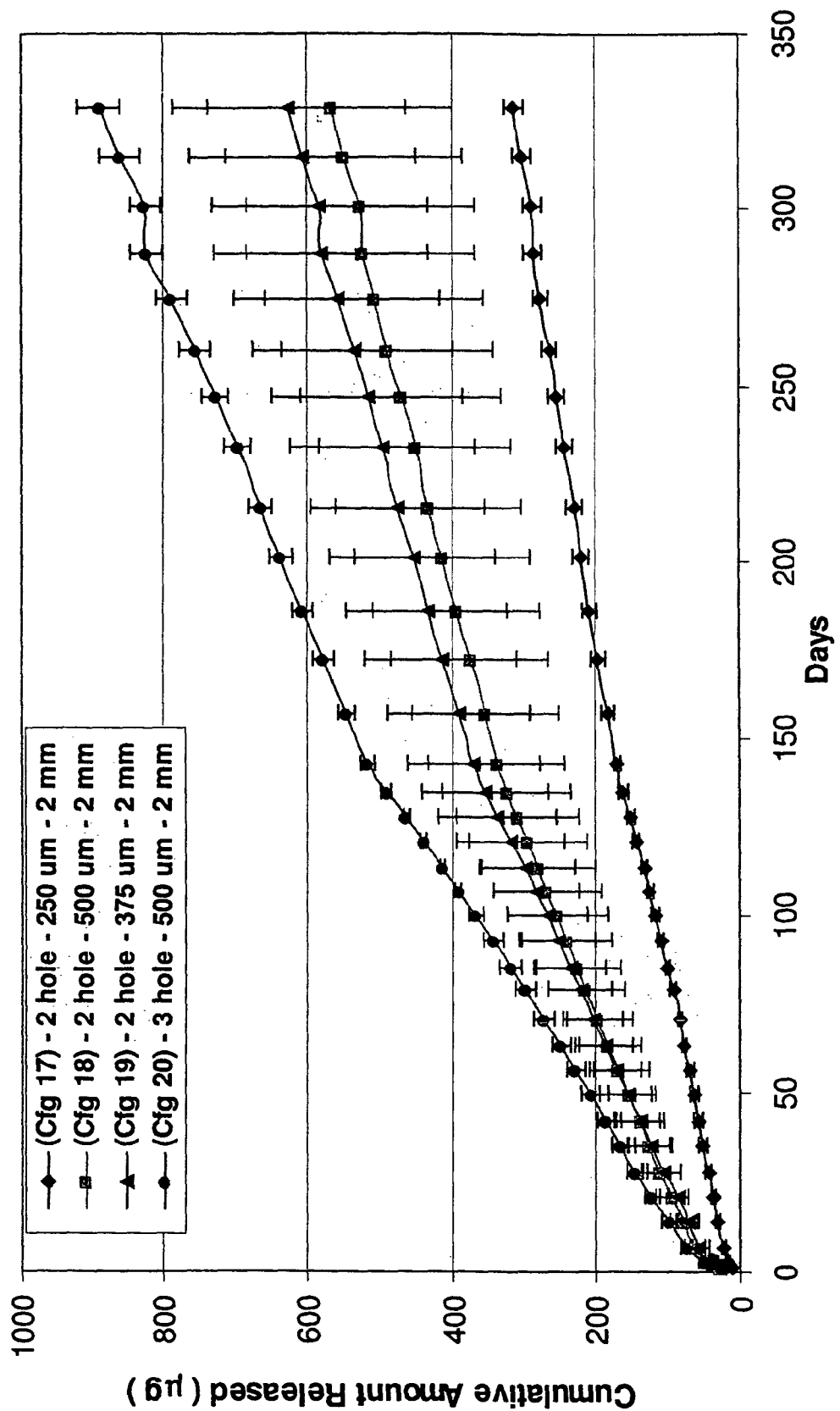
FIG. 12 is a graph showing the cumulative release profiles for sterile fluocinolone acetonide containing implants having different hole configurations.
Figure 13:
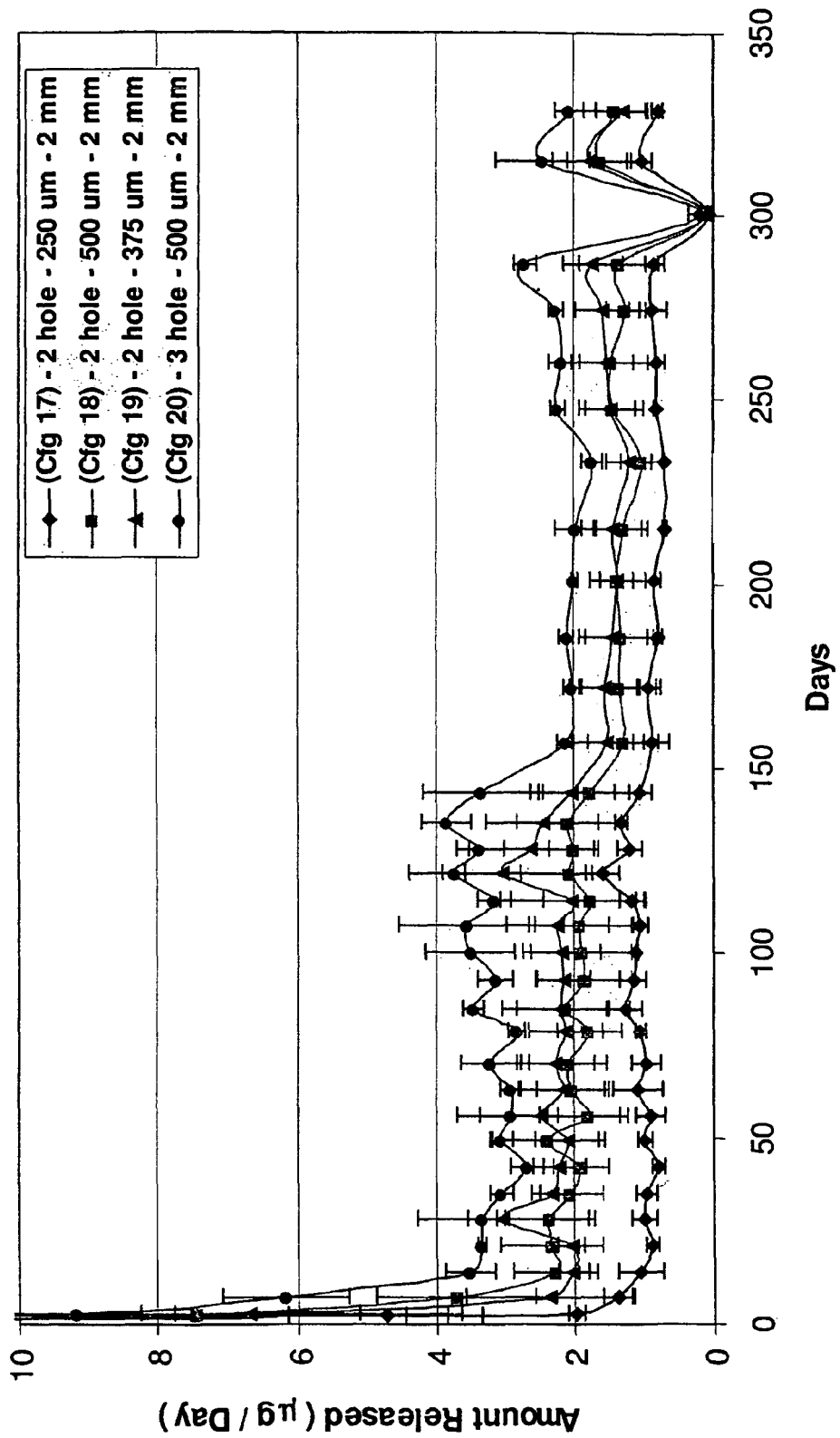
FIG. 13 is a graph showing the amount of fluocinolone released per day for the implants described in FIG. 12.
Figure 14:
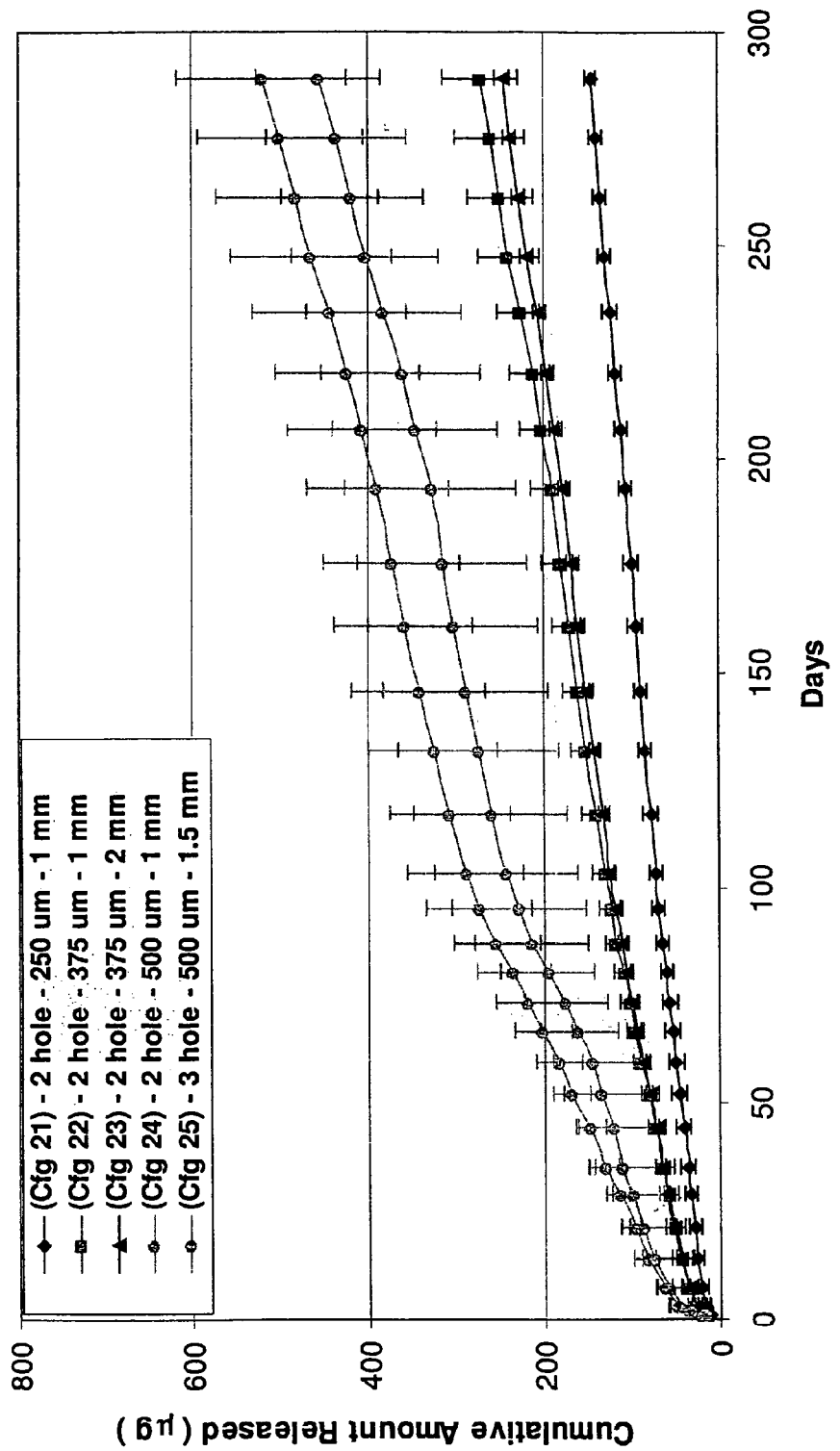
FIG. 14 is a graph showing the cumulative release profiles for non-sterile fluocinolone acetonide containing implants having different hole configurations.
Figure 15:
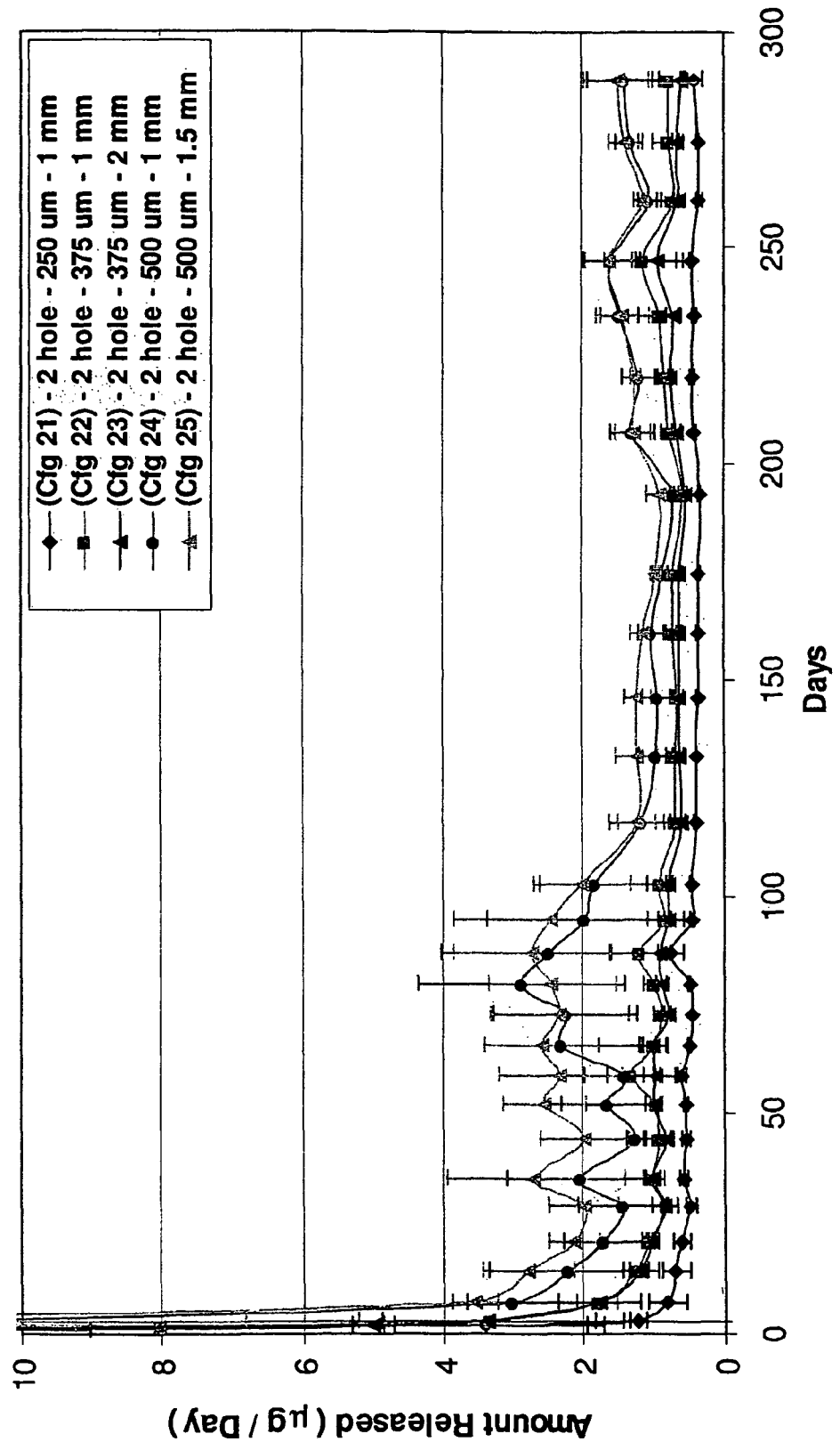
FIG. 15 is a graph showing the amount of fluocinolone released per day for the implants described in FIG. 14.
Figure 16:
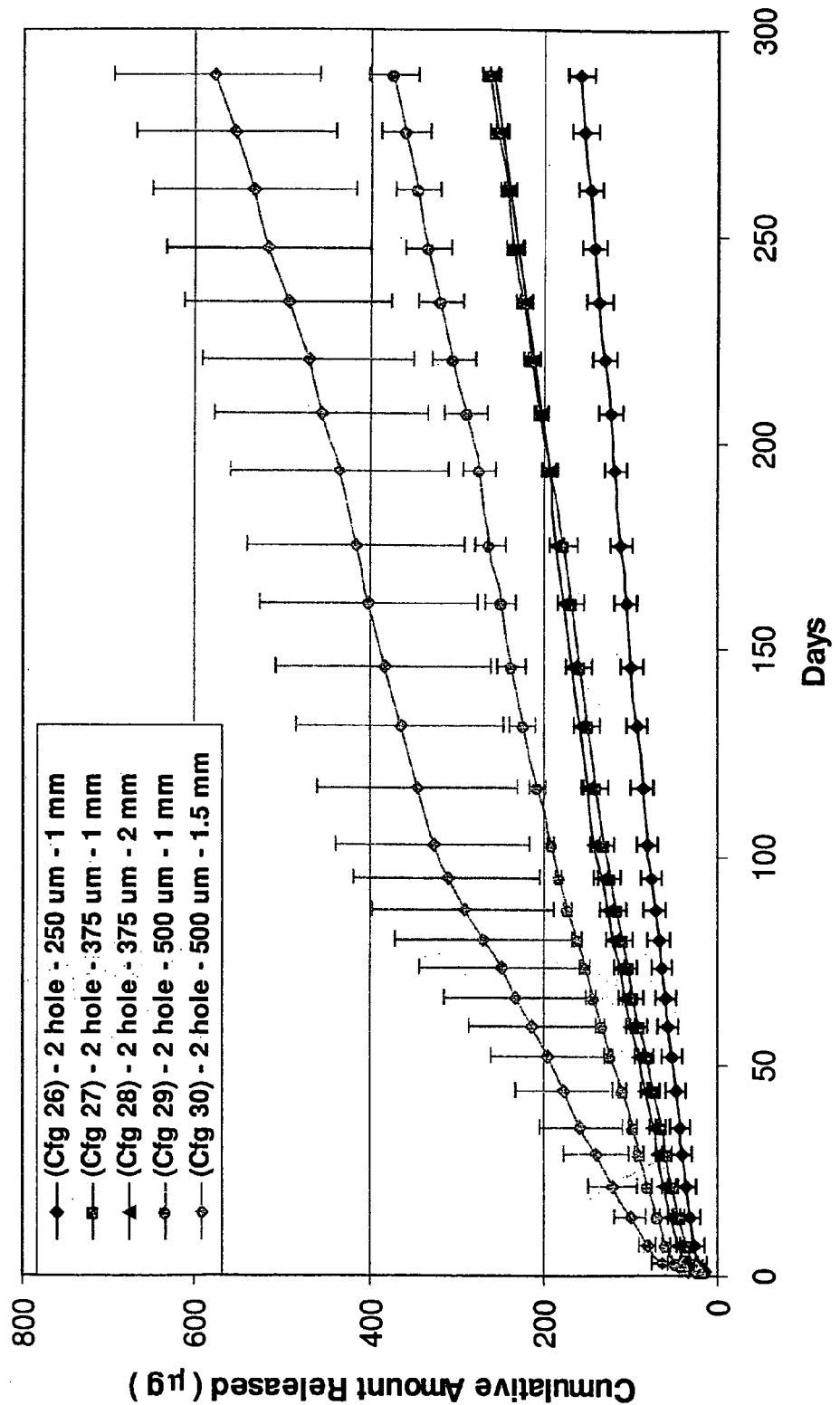
FIG. 16 is a graph showing the cumulative release profiles for sterile fluocinolone acetonide containing implants described in FIG. 14.
Figure 17:
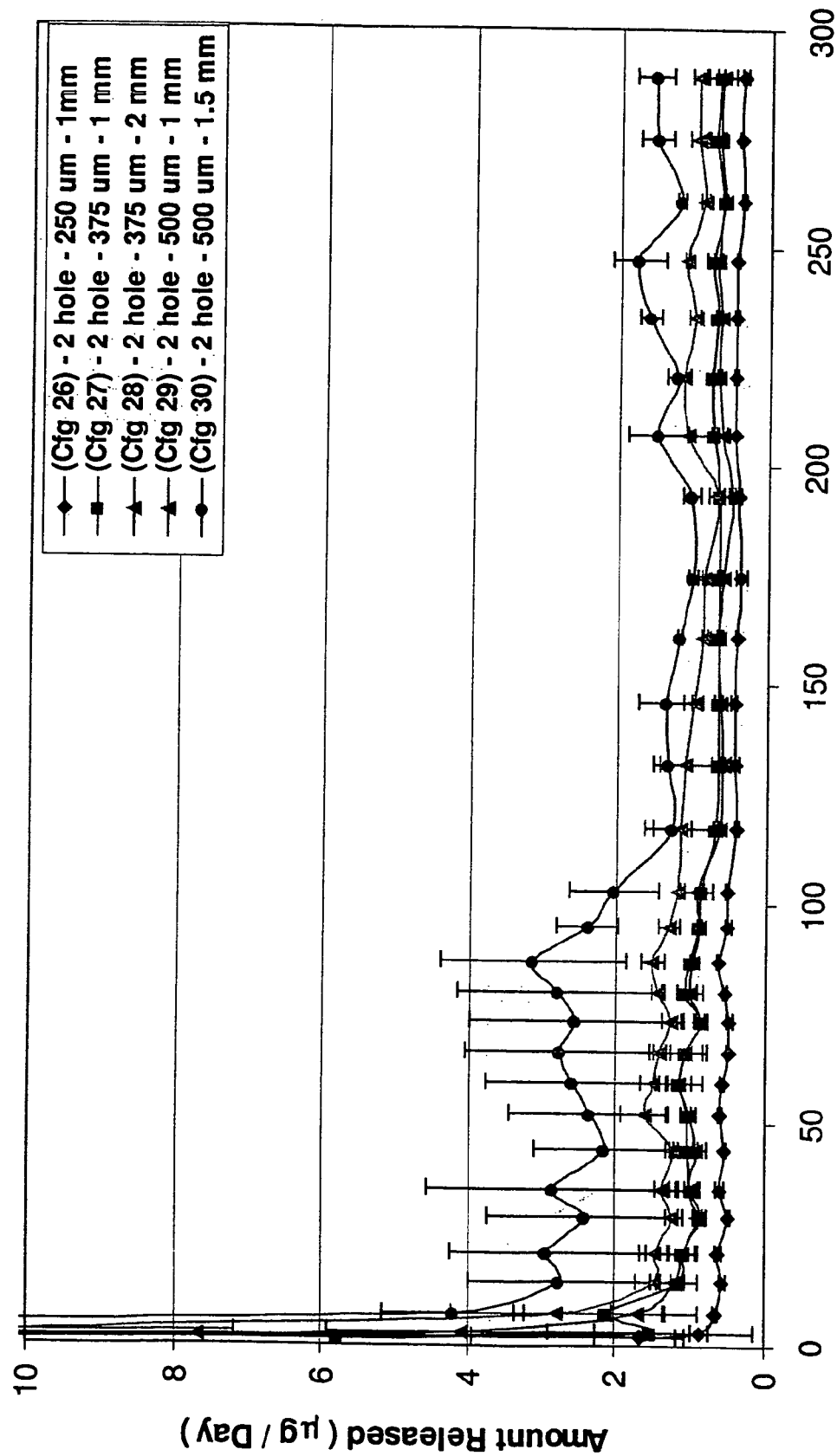
FIG. 17 is a graph showing the amount of fluocinolone released per day for the implants described in FIG. 16.
Figure 18:
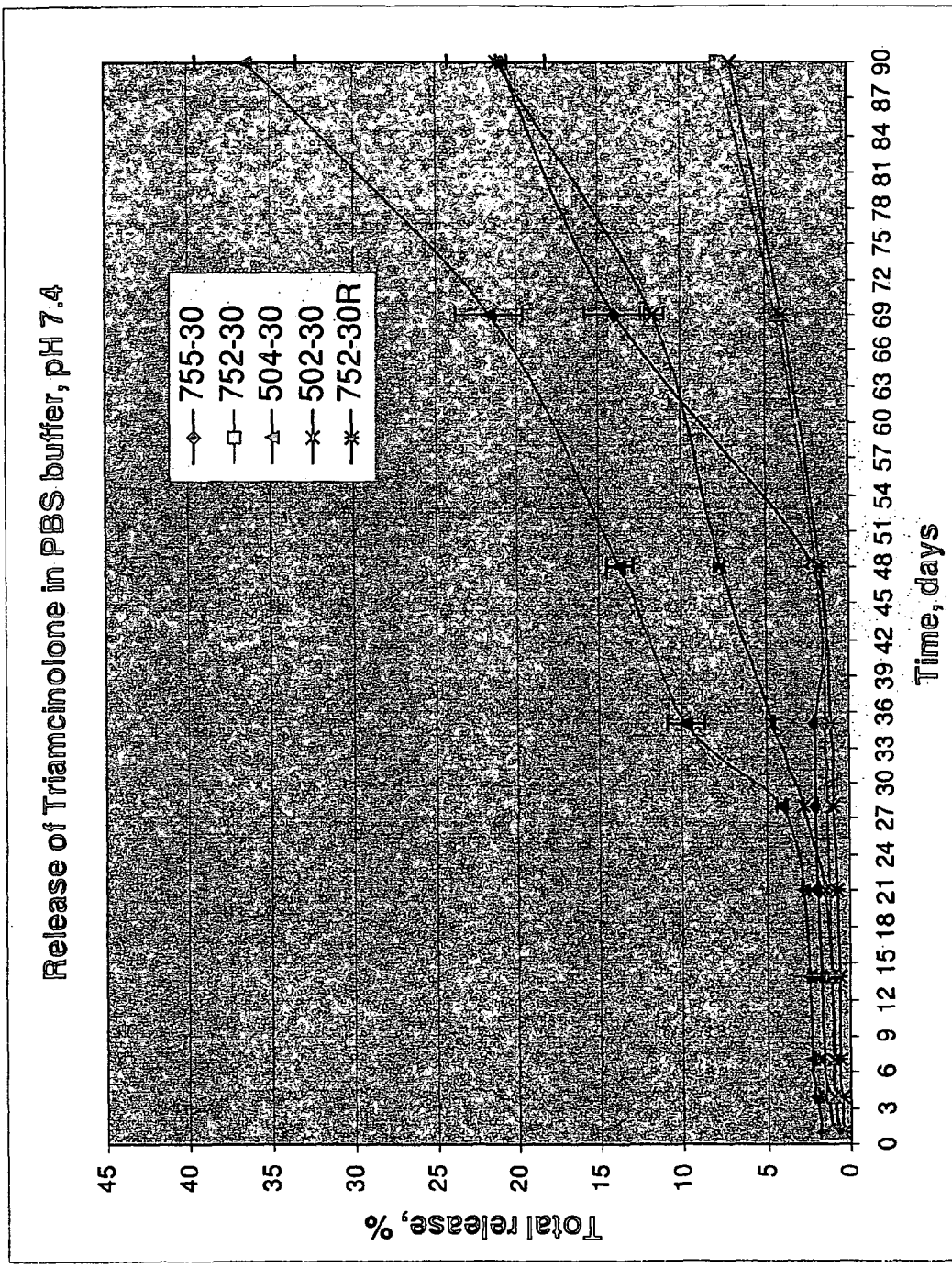
FIG. 18 is a graph showing the total percent release of triamcinolone as a function of time in phosphate buffered saline for implants containing 30% triamcinolone.
Figure 19:
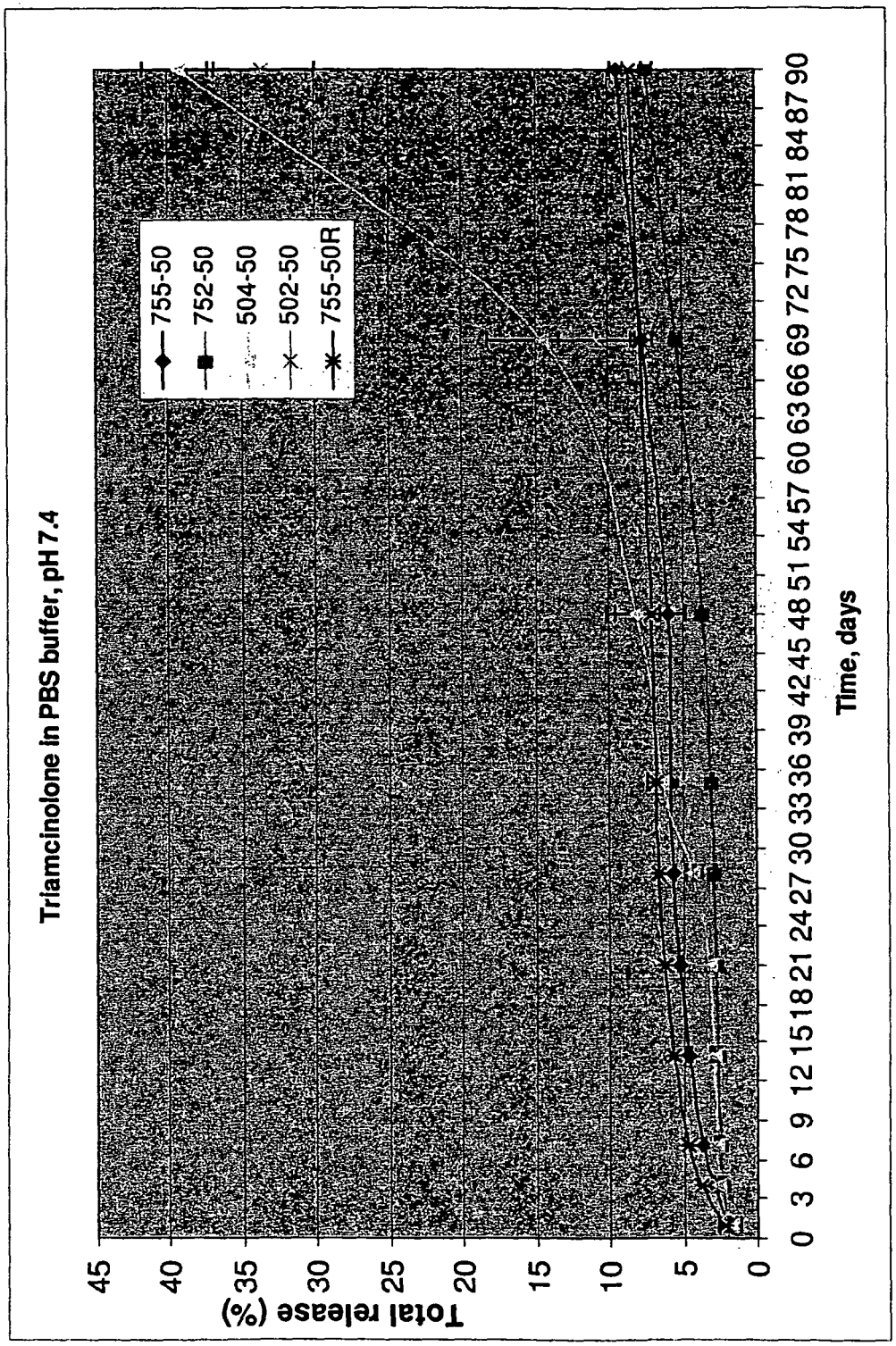
FIG. 19 is a graph showing the total percent release of triamcinolone as a function of time in phosphate buffered saline for implants containing 50% triamcinolone.
Figure 20:
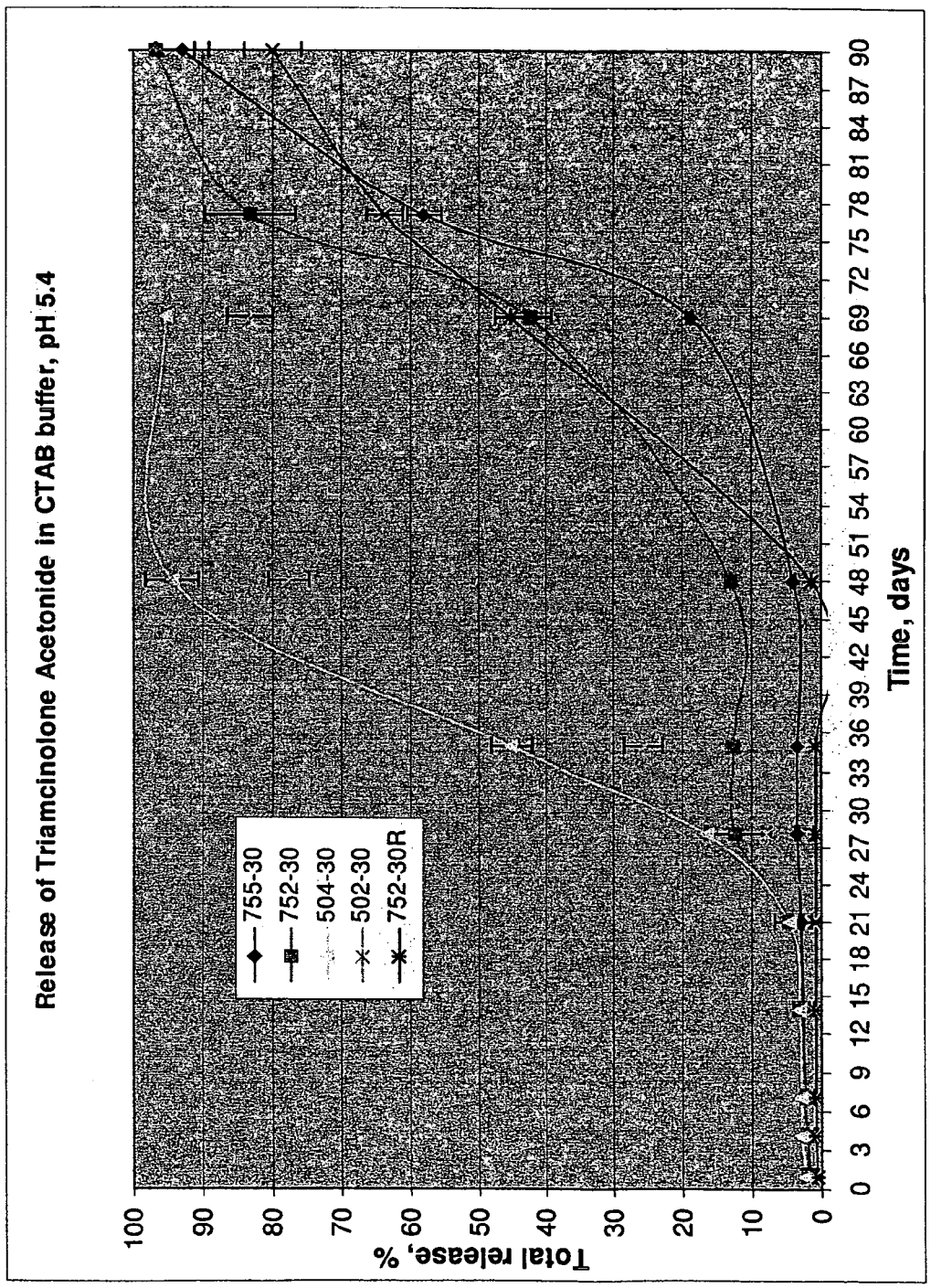
FIG. 20 is a graph showing the total percent release of triamcinolone as a function of time in citrate phosphate buffer for implants containing 30% triamcinolone.
Figure 21:
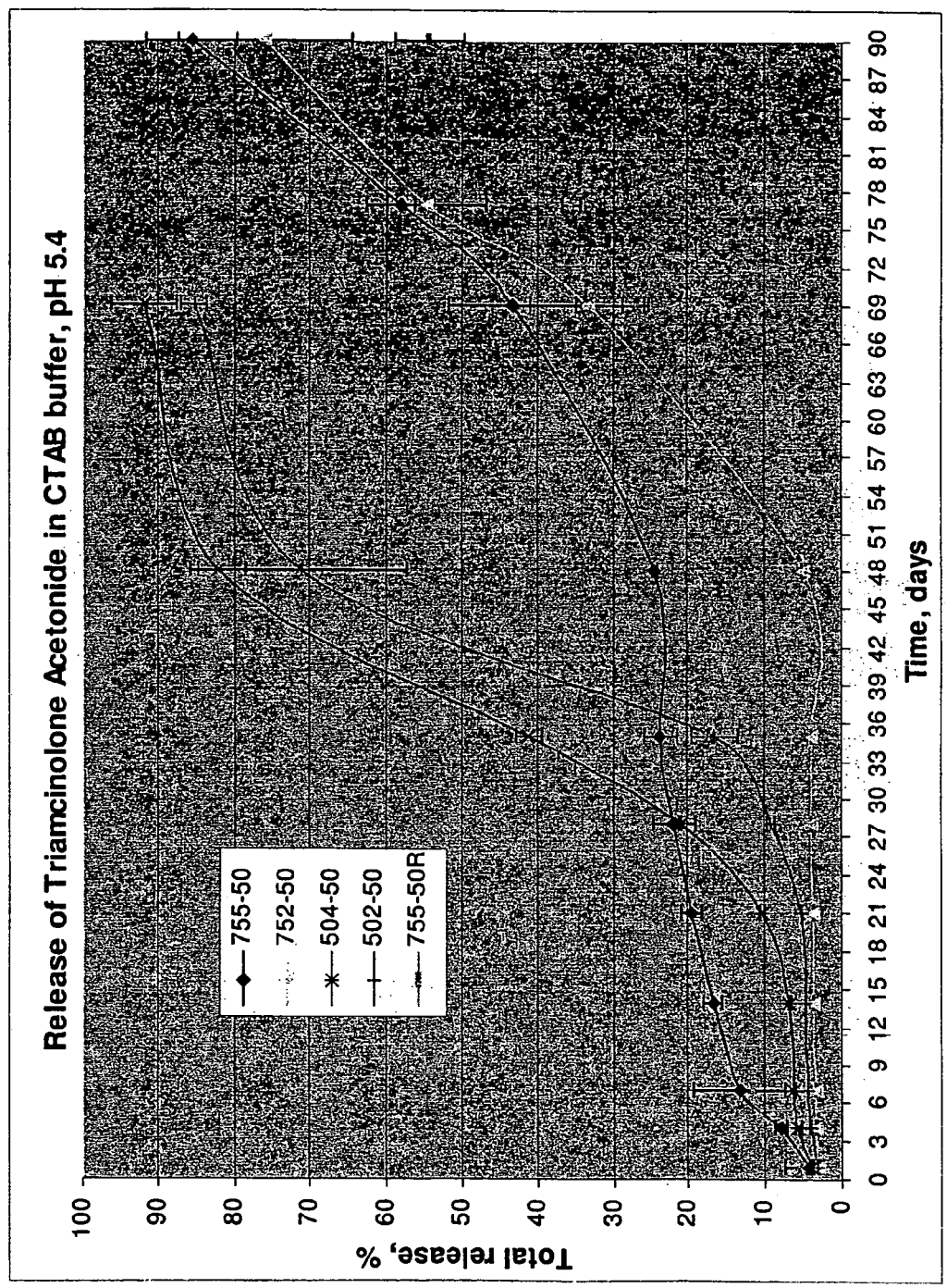
FIG. 21 is a graph showing the total percent release of triamcinolone as a function of time in citrate phosphate buffer for implants containing 50% triamcinolone.
Figure 22:
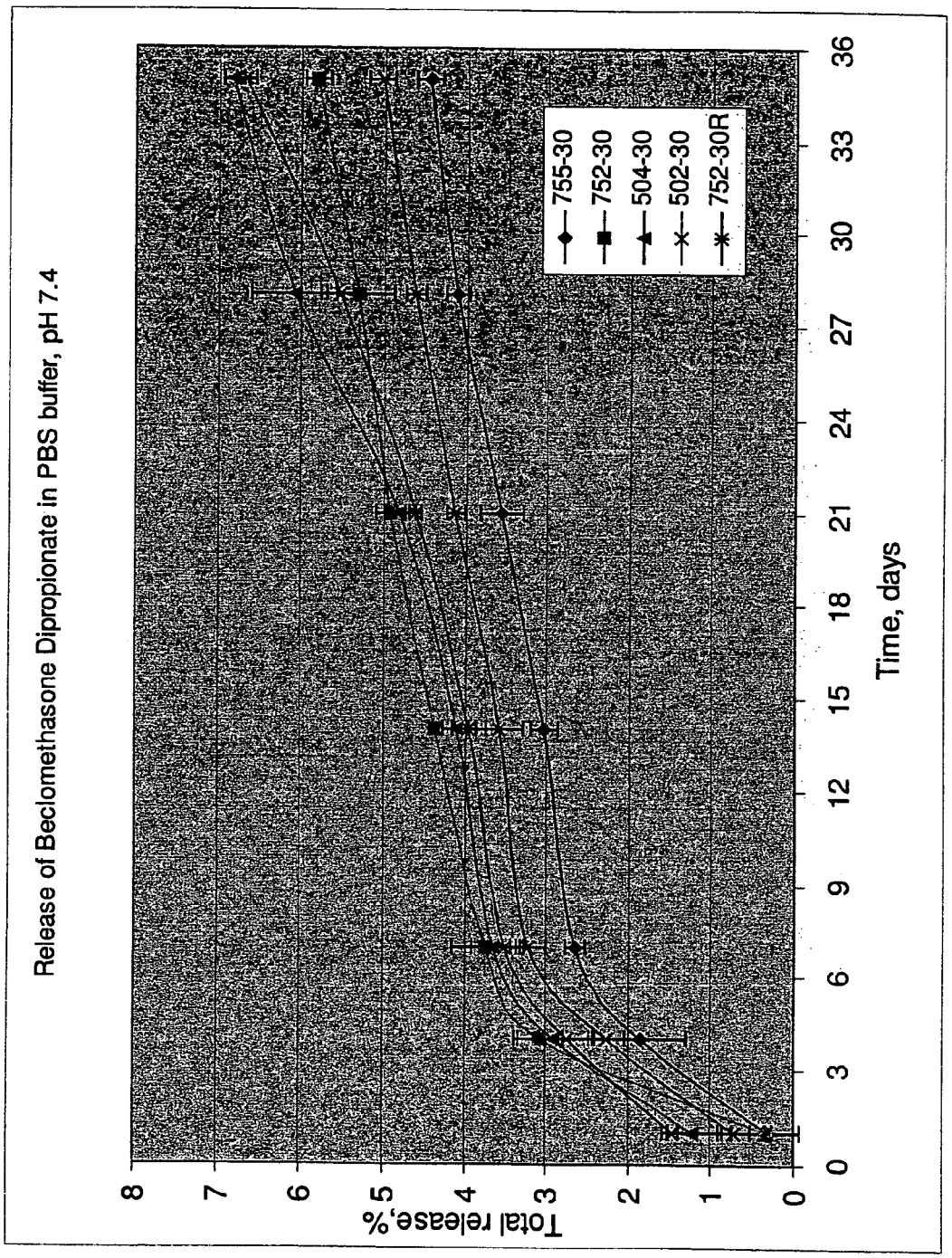
FIG. 22 is a graph showing the total percent release of beclomethasone propionate as a function of time in phosphate buffered saline for implants containing 30% triamcinolone.
Figure 23:
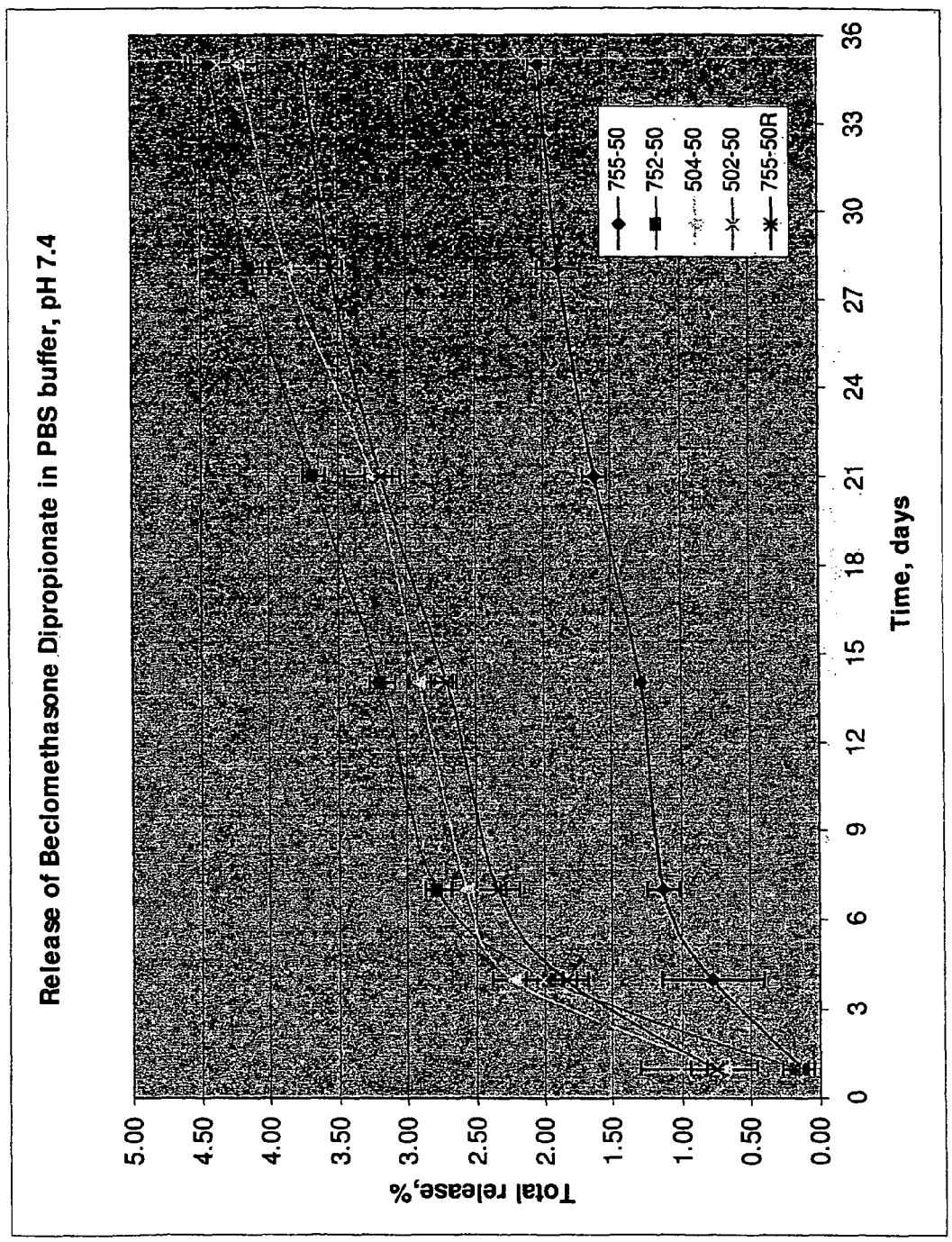
FIG. 23 is a graph showing the total percent release of beclomethasone propionate as a function of time in phosphate buffered saline for implants containing 50% triamcinolone.
Figure 24:
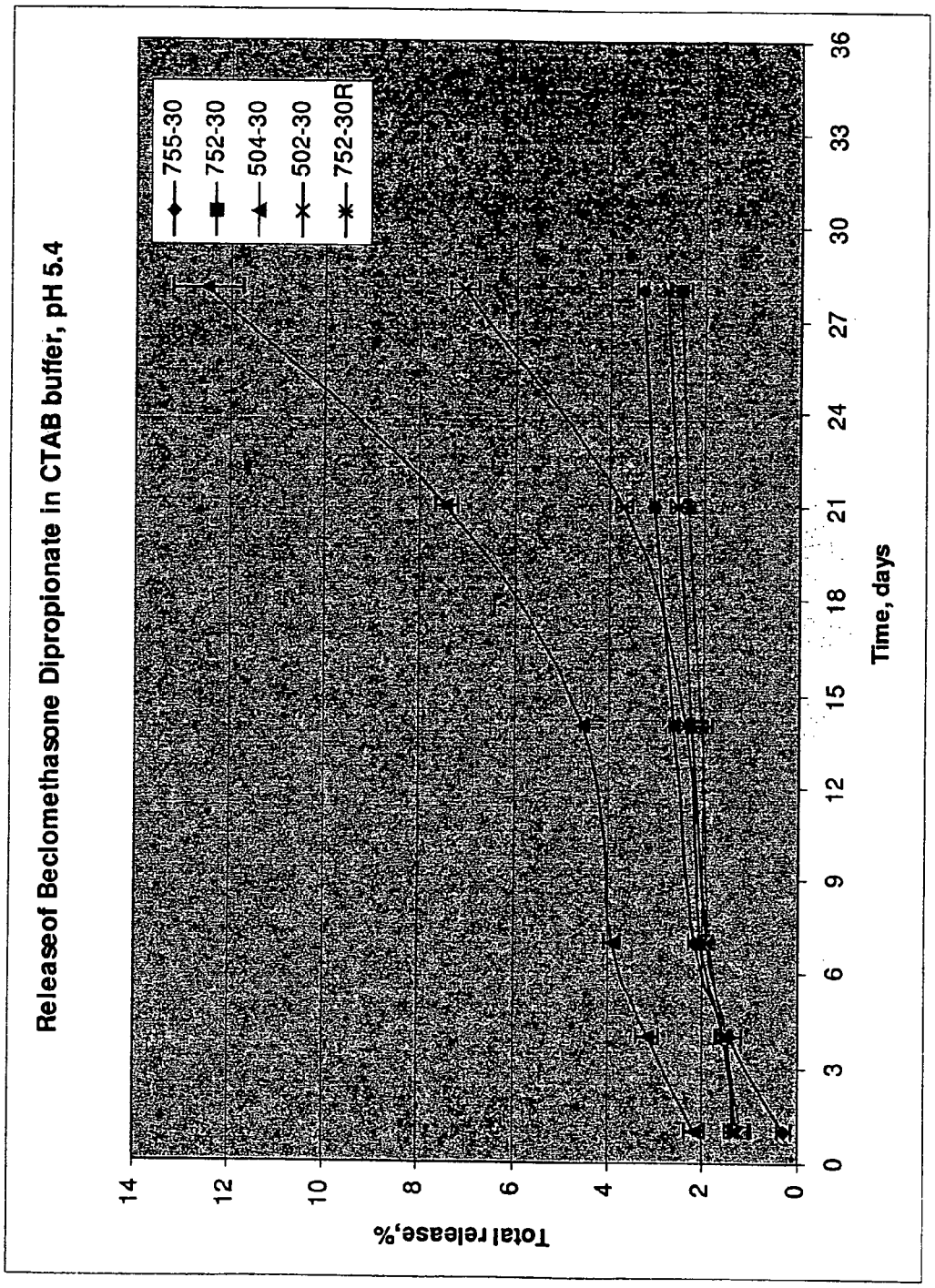
FIG. 24 is a graph showing the total percent release of beclomethasone propionate as a function of time in citrate phosphate buffer for implants containing 30% triamcinolone.
Figure 25:
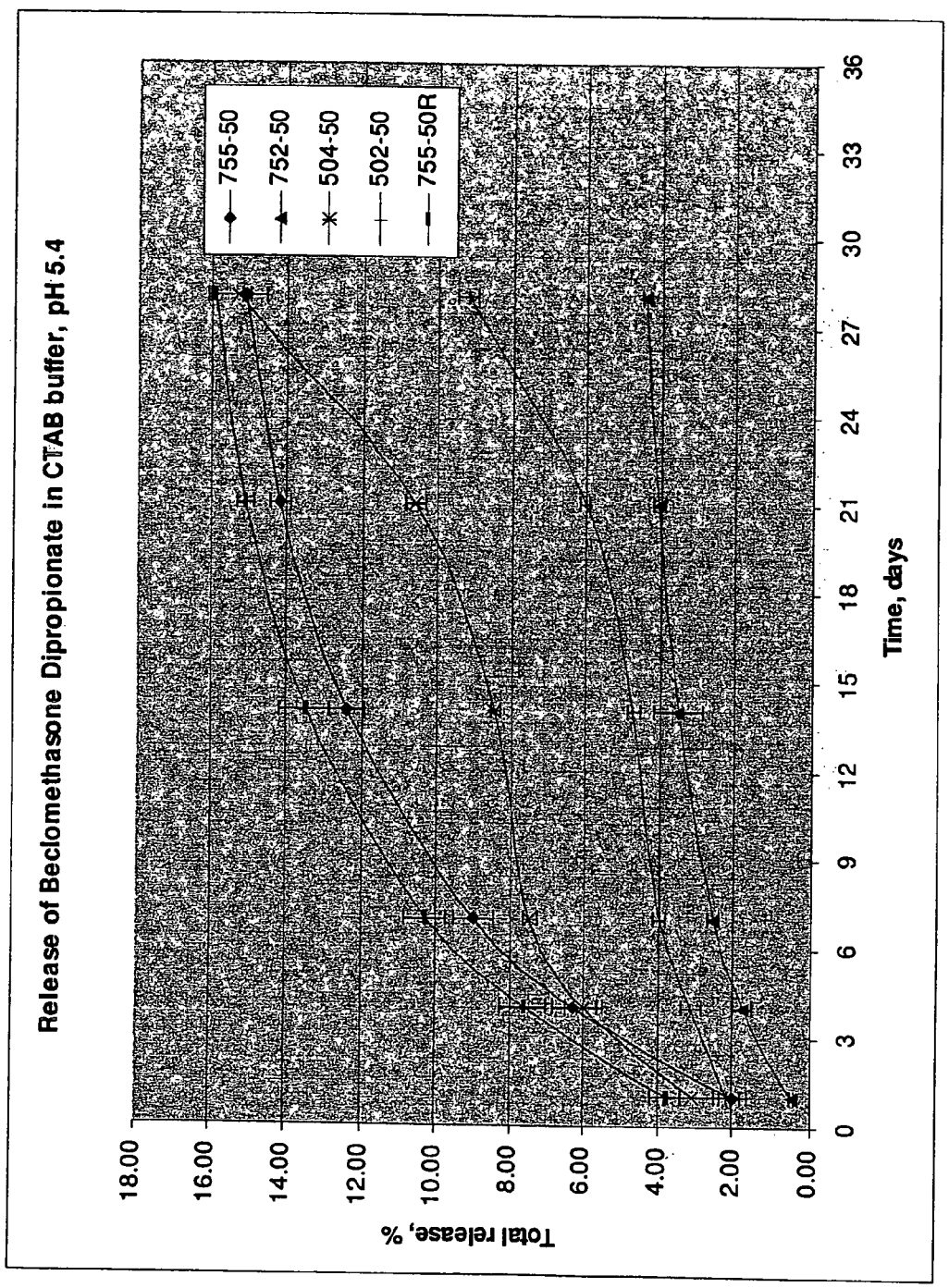
FIG. 25 is a graph showing the total percent release of beclomethasone propionate as a function of time in citrate phosphate buffer for implants containing 50% triamcinolone.

Implants were also manufactured to provide a fluocinolone release rate of about 0.5 μg/day. Tubular implants were manufactured to have a length of about 0.7 cm filled with approximately 2.8 mg±0.34 mg of drug and are identified as configurations 17, 18, 19, and 20. The cumulative amount of fluocinolone released (μg) as a function of time and the amount of release (μg) per day as a function of time are presented in FIGS. 12 and 13, respectively.

The results showed an average release of 0.95±0.14, 1.71±0.55, 1.93±0.56, and 2.76±0.27 μg/day, for configurations 17, 18, 19, and 20, respectively, from day 14 through day 329. Since the length of the tube for configurations 17, 18, 19, and 20 was shortened from 1.0 cm to 0.7 cm, approximately 0.15 cm of silicone tubing was removed from both ends. As a result, the holes became much closer to the end of the tube, to the extent that the glue almost touched the circumference of the holes during preparation. It was not clear whether this affected the release profiles. To circumvent this potential problem, configurations with holes much closer to each other toward the center and away from the ends were prepared.

The last ten configurations were 0.7 cm in length with drug load of approximately 2.69 mg±0.36 mg in each device. Configurations 21 through 25 were pre-sterile, while configurations 26 through 30 were sterile. The cumulative amount released (μg) as a function of time and the amount of release (μg) per day as a function of time are presented in FIGS. 14 through 17.

Results from day 14 to day 289 showed an average release of 1.01±0.23, 1.76±0.57, 1.73±0.30, 3.0±1.26, and 3.32±1.06 μg/day for configurations 21, 22, 23, 24, and 25, respectively. Similarly, the data for configurations 26, 27, 28, 29, and 30, which were the sterile counterparts, showed an average release of 0.48±0.03, 0.85±0.09, 0.82±0.08, 1.19±0.15, and 1.97±0.69 μg/day, respectively, from day 14 through day 289. Configuration #26 (2 holes—250 μm-1 mm apart) achieved an average release of 0.5 μg/day (e.g., 0.48±0.03 μg/day from day 14 through day 289) and a total release of 5.76%±0.32% over 289 days or close to 9½ months. Based on its release rate, it has a life span of 13.75 years. In general, the non-sterile configurations are approximately twice as fast as the sterile counterparts.

Example 4

Manufacture and In Vivo Testing of Intraocular Implants Containing Fluocinolone and a Polymer Coating An in vivo study was conducted with an implant as shown by configuration #29 in Example 3. The implant was manufactured as described in Example 3. Configuration #29 achieved an average release of 1.19±0.15 μg/day, and a total release of 14.28%±1.59% over 289 days when tested in vitro.

The in vivo study was conducted on four rabbits. The fluocinolone-containing implants were surgically implanted into the posterior segment (i.e., the vitreous) of the right eye (OD) and left eye (OS) of each rabbit. The aqueous humor (15-20 μL) and the vitreous humor (150-200 μL) were withdrawn for the first two rabbits, while the sampling for the remaining two rabbits was determined by a sampling schedule wherein the sampling days were days 7, 14, 21, 40, and 60, 90, and 120. The results of the in vivo study are shown in Table 4.

TABLE 4

Fluocinolone acetonide Levels in Vitreous Humor of Rabbit Eyes Posterior Segment

| | Fluocinolone (ng/mL) Day | | | | | | |
|---|---|---|---|---|---|---|---|
| | 7 | 14 | 21 | 40 | 60 | 90 | 120 |
| 8408D | 242.00 | | | | | | |
| 8408S | 88.60 | | | | | | |
| 8399D | 9.08 | 6.84 | 3.06 | | 4.56 | 10.26 | 15.18 |
| 8399S | 44.00 | 74.20 | 85.80 | | 83.60 | 75.60 | 44.00 |
| 8407D | | 105.80 | 87.20 | | 135.80 | 68.60 | 57.20 |
| 8407S | | 16.64 | 6.78 | | 14.92 | 6.62 | 3.46 |
| 8397D | | | | 44.00 | 42.20 | 32.40 | 24.20 |
| 8397S | | | | 40.80 | 22.60 | 23.00 | 24.80 |
| Average | 95.92 | 50.87 | 45.71 | 42.40 | 50.61 | 36.08 | 28.14 |
| SD | 102.68 | 47.16 | 47.13 | 2.26 | 50.19 | 29.46 | 19.49 |

The mean vitreous levels of fluocinolone were relatively higher in the first week and then remained at approximately between 30 and 50 ng/mL beyond the second week. Fluocinolone acetonide was not detected at any time point in the anterior chamber of all eyes.

Thus, by way of Examples 3 and 4, implants have been developed that can deliver fluocinolone at a substantially constant release rate of 2 μg/day or 0.5 μg/day for extended periods of time (e.g., for over 1-2 years).

Configuration #29 (2 hole—500 μm-1 mm) was used in the in vivo study and fluocinolone acetonide concentrations were measured between 0.026 μg/mL to 0.096 μg/mL over 120 days in the vitreous, while essentially no level was found in the aqueous humor.

It was noticed that the release profiles differed depending on when the implants were sterilized. For some configurations, the before sterilization release rates are about twice as fast as the after sterilization ones, and in other configurations, the reverse was observed. It is possible that sterilization may change the size of the holes in the implants. Two animals developed cataracts after day 120.

Example 5

Treatment of Uveitis with an Intraocular Implant Containing Fluocinolone Associated with a Biodegradable Polymer Matrix A 48 year old female presents with posterior uveitis. She complains of sensitivity to light and ocular pain. An implant containing 250 μg of fluocinolone acetonide and 250 μg of a combination of biodegradable polymers (R502H and R202H at a 1:2 ratio, as described above in Example 1) is placed in the vitreous of both of the woman's eyes using a trocar. After about 2 days, the woman begins to notice a decrease in ocular pain and light sensitivity. She also notices a decreased blurring of vision, and a decrease in floaters. Substantial relief from the uveitis symptoms is obtained within about 7 days, and persists for about three months.

Example 6

Treatment of Uveitis with an Intraocular Implant Containing Fluocinolone Associated with a Polymeric Coating A 62 year old male presents with posterior uveitis. An implant containing 250 μg of fluocinolone acetonide with a polymeric coating having two 500 μm diameter holes spaced 1 mm apart is implanted into the vitreous of both of the patient's eyes using a trocar. The patient reports a decrease in pain and improvement in vision within a week after implantation. The improvements persist for about two years. No cataracts develop over that time.

Example 7

Treatment of Macular Edema with a Steroid Containing Intraocular Implant

A 53 year old male with macular edema is treated by injecting a biodegradable implant into the vitreous of each of the patient's eyes using a syringe with a needle. The implants contain 500 μg of fluocinolone acetonide and 500 μg of PLGA. The patient reports a decrease in pain and improvement in vision within a week after implantation. The improvements persist for about two years. No cataracts develop over that time.

Example 8

Treatment of Macular Degeneration with a Steroid Containing Intraocular Implant

A 82 year old female diagnosed with macular degeneration in her right eye is treated by intravitreal placement of a biodegradable implant containing 600 μg of fluocinolone acetonide and 500 μg of PLGA. The implant is placed near the fovea without interfering with the patient's vision. Further ophthalmic diagnosis indicates that macular degeneration is suspended, and the patient does not perceive further vision loss associated with macular degeneration. Throughout the treatment, intraocular pressure remains within acceptable limits.

Example 9

Effects of Polymer Properties and Drug Load on Intraocular Implants

This example describes effects of poly (lactide-co-glycolide) (PLGA) polymer properties and drug load on in-vitro drug release profiles of steroids from polymeric implants. More specifically, this example describes the effects of polymer molecular weight (MW), lactide-glycolide (LG) ratio, and steroid load on the release profile of triamcinalone acetonide (TA) or beclomethasone dipropionate (BD) from poly (D,L-lactide-co-glycolide) polymer implants containing triamcinalone acetonide (TA) or beclomethasone dipropionate (BD).

Drug release profiles of the present implants are related to the molecular weight (MW) of the polymer, such as PLGA in this example, the lactide-glycolide ratio (LG) of the polymer, and the drug load or amount of drug in the implant. Steroid release from the implants was examined in phosphate buffered saline (pH 7.4; PBS) or citrate phosphate buffer containing 0.1% cetyltrimethylammonium bromide (pH 5.4; CTAB).

In short, the implants were made by melt extrusion, and the steroid release from the implant was assayed by HPLC after incubation at 37° C. in phosphate buffered saline pH 7.4 or citrate phosphate buffer with 0.1% cetyltrimethylammonium bromide pH 5.4. Triamcinalone release from the implants was monitored for 90 days, and beclomethasone dipropionate release from implants was monitored for 35 days.

The results of these experiments show that both steroids release much faster in the citrate buffer compared to the phosphate buffer. During the first 30 days, the release profiles of the two steroids are very similar even though triamcinalone acetonide is about 150 times more water soluble than beclomethasone dipropionate. Polymer properties have a minor effect on the release profile in this time frame or portion of the release profile (e.g., within approximately the first 30 days). In this early phase, the release appears to be controlled by the drug dissolution. The polymer properties become more important after the first 30 days or during a second time frame or portion of the release profile as the polymer's hydrolysis rate differences become more important.

Triamcinalone acetonide was obtained from Pharmacia Upjohn Co. Beclamethasone dipropionate was obtained from Sigma. PLGA polymers RG502, RG504, RG752, and RG755 were obtained from Boehringer-Ingelheim Pharma GmbH & Co. (Germany). Saline solution (0.9% NaCl) was obtained from VWR Scientific. Cetyltrimethylammonium bromide (CTAB) was obtained from Aldrich.

The following equipment was used: a ball mill (model mm200; F. Kurt Retsch GmbH & Co., Germany); a turbula shaker (model T2F Nr.990720, Glen Mills, Inc., New Jersey); a piston extruder obtained from APS Engineering, Inc.; a compactor (model A-1024, Jamesville Tool & Manufacturing, Inc., Milton Wis.); a shaking water bath (model 50, Precision Scientific, Winchester, Va.); a high pressure liquid chromatograph (HPLC, model Alliance 2695, Equipped with a Waters 2497 Dual Wavelength Absorbance Detector, Waters, Inc., Milford, Mass.); and an oven (model 1330F, VWR Scientific, Cornelius, Oreg.).

In this example, implants were produced by an extrusion process. Steroids and polymer(s) were combined in a stainless steel ball-mill capsule along with two stainless steel mixing balls. The capsule was placed on the ball mill for five minutes at 20 cps. The capsule was removed from the ball mill and the content was stirred with a spatula; then placed back on the ball mill. This was repeated for two more five-minute cycles. The ball-mill capsule was then placed on a Turbula mixer for five minutes at 20 cps. The content of the capsule was transferred in small increments to an extruder barrel fitted with a die using a spatula and a small stainless steel funnel. After each increment, the powder was compacted in the extruder barrel with the compactor set at 50 psi. When the extruder barrel was full, it is transferred to the extruder and the extruder was heated to temperature and allowed to equilibrate. The polymer steroid mixture was extruded through the die at 0.025 in/min.; the resulting filament was cut into approximately four-inch lengths and placed into a 60-mL screw cap vial, which was placed in a laminated foil pouch with a desiccant pack.

The experimental conditions for the extrusions are shown in Table 5 and Table 6 for triamcinalone acetonide and beclamethasone dipropionate, respectively.

TABLE 5

Triamcinalone Acetonide/PLGA Extrusion Parameters

| Polymer | Polymer ratio, % | Drug Load, % | Compactor Press, psi | Diameter of Die, um | Extrusion Speed, "/min | Extrusion Temp, ° C. |
|---|---|---|---|---|---|---|
| RG752 | 100 | 30 | 50 | 720 | 0.0025 | 95 |
| RG752 | 100 | 50 | 50 | 720 | 0.0025 | 96 |
| RG755 | 100 | 30 | 50 | 720 | 0.0025 | 97 |
| RG755 | 100 | 50 | 50 | 720 | 0.0025 | 96 |
| RG502 | 100 | 30 | 50 | 720 | 0.0025 | 97 |
| RG502 | 100 | 50 | 50 | 720 | 0.0025 | 98 |
| RG504 | 100 | 30 | 50 | 720 | 0.0025 | 94 |
| RG504 | 100 | 50 | 50 | 720 | 0.0025 | 98 |
| RG755 | 100 | 50 | 50 | 720 | 0.0025 | 101 |
| RG752 | 100 | 30 | 50 | 720 | 0.0025 | 87 |

TABLE 6

Beclomethasone/PLGA Extrusion Parameters

| Polymer | Polymer ratio, % | Drug Loading, % | Compactor Press, psi | Diameter of Die, um | Extrusion Speed, "/min | Extrusion Temp*, ° C. |
|---|---|---|---|---|---|---|
| RG755 | 100 | 30 | 50 | 720 | 0.0025 | 94 |
| RG755 | 100 | 50 | 50 | 720 | 0.0025 | 99-109 |
| RG752 | 100 | 30 | 50 | 720 | 0.0025 | 95-100 |
| RG752 | 100 | 50 | 50 | 720 | 0.0025 | 96 |
| RG504 | 100 | 30 | 50 | 720 | 0.0025 | 98 |
| RG504 | 100 | 50 | 50 | 720 | 0.0025 | 104-114 |
| RG502 | 100 | 30 | 50 | 720 | 0.0025 | 89-99 |
| RG502 | 100 | 50 | 50 | 720 | 0.0025 | 95-96 |
| RG755 | 100 | 50 | 50 | 720 | 0.0025 | 95 |
| RG752 | 100 | 30 | 50 | 720 | 0.0025 | 95 |

*The mixture of API (the active pharmaceutical ingredient, that is the drug used) and polymer were left in the extruder at 90° C. for 10 min before extrusion was started.

The extruded filaments were cut into 1-mg weight rod-shaped implants (rods). Each rod was placed in a 60-mL vial with 50 mL of phosphate buffered saline pH 7.4 or citrate phosphate buffer pH 5.4 with 0.1% cetyltrimethylammonium bromide (CTAB) in an oscillating water bath (50 rpm) at 37° C. At each time point, the released steroid was assayed (n=6) by HPLC, and the solution was removed from the vial and replaced with fresh buffer. The steroid release was measured after the following days: 1, 4, 7, 14, 21, 28, 35, 48 69, 77, and 90.

Triamcinalone acetonide (TA) released from the PLGA (poly(lactide-co-glycolide) polymer implant was assayed by HPLC (Waters, Milford, Mass.) employing a Waters Symmetry C18, 4.6×75 mm, 3 µm column. The mobile phase was acetonitrile-water (35:65, v/v) with a flow rate of 1.0 mL/min and an injection volume of 20 µL. Ultraviolet detection of TA was done at 243 nm. The total run time was 10 min and the TA retention time was 4.0 min. Quantization was based on peak area and a triamcinalone acetonide standardization curve.

Beclomethasone dipropionate (BD) released from the PLGA polymer implant was assayed by HPLC (Waters, Milford, Mass.) employing a Discovery HS F5 C18, 4.6×150 mm, 5 µm column. The mobile phase was acetonitrile-water (85:15), v/v) with a flow rate of 0.8 mL/min and an injection volume of 30 µL. Ultraviolet detection of BD was done at 240 nm. The total run time was 5 min and BD retention time was 2.5 min. Quantization was based on peak area and a BD standardization curve.

The results from the design were analyzed qualitatively at three times during the dissolution—early, middle and late.

The triamcinalone acetonide release results are shown in Tables 7-10 and in FIGS. 18 to 21, respectively.

As shown, TA released into the CTAB buffer faster than it was released into the PBS buffer. Drug release rate can also be effected by pH and surfactant which can alter the polymer's hydrolysis rate and therefore the drug release rate.

The drug load in the polymer has the largest positive effect on the drug release rate compared to MW and LG ratio for the first 30 days. After the first 30 days, the LG ratio dominated the drug release rate and showed a negative effect. In other words, a higher LG ratio resulted in a slower drug release. Without wishing to be bound by any particular theory or mechanism of action, these effects may be related to high drug loading early in the dissolution resulting in more available drug at the polymeric implant's surface. As drug becomes less available, the drug release rate may be controlled by the hydrolysis of the polymer, which is faster for the lower LG ratio polymer.

Molecular weight of the polymer had a positive effect on drug release rate especially later in the dissolution—faster release was observed with higher MW polymers. While not wishing to be bound by any particular theory or mechanism of action, this may occur because the lower MW polymer pack more densely, and the higher MW polymer hydrolyze faster. Overall, the data show that early drug release is controlled by the drug load but the later in time drug release rate is controlled by the polymer hydrolysis rate.

TABLE 7

Triamcinalone Release Results in Phosphate Buffered Saline pH 7.4 for 30% Drug Load

| | 755-30 | 752-30 | 504-30 | 502-30 | 752-30R |
|---|---|---|---|---|---|
| | Total release (%) | | | | |
| 1 | 1.08 | 0.81 | 1.75 | 0.74 | 0.46 |
| 4 | 1.40 | 1.02 | 2.13 | 0.94 | 0.49 |
| 7 | 1.56 | 1.08 | 2.29 | 1.00 | 0.59 |
| 14 | 1.70 | 1.10 | 2.47 | 1.11 | 0.60 |
| 21 | 1.92 | 1.28 | 2.86 | 1.47 | 0.69 |
| 28 | 2.05 | 1.37 | 4.14 | 2.77 | 0.97 |
| 35 | 2.08 | 1.41 | 9.73 | 4.60 | 1.06 |
| 48 | 2.22 | 1.98 | 13.74 | 7.73 | 1.65 |
| 69 | 14.03 | 4.42 | 21.70 | 11.70 | 3.98 |
| 90 | 20.94 | 7.82 | 36.46 | 21.22 | 7.05 |
| | Standard Deviation | | | | |
| 1 | 0.08 | 0.12 | 0.14 | 0.04 | 0.09 |
| 4 | 0.05 | 0.11 | 0.13 | 0.04 | 0.03 |
| 7 | 0.04 | 0.04 | 0.06 | 0.04 | 0.03 |
| 14 | 0.03 | 0.02 | 0.07 | 0.05 | 0.02 |
| 21 | 0.03 | 0.03 | 0.03 | 0.01 | 0.04 |
| 28 | 0.05 | 0.03 | 0.19 | 0.02 | 0.11 |
| 35 | 0.02 | 0.03 | 1.09 | 0.09 | 0.05 |
| 48 | 0.12 | 0.03 | 0.83 | 0.33 | 0.10 |
| 69 | 1.87 | 0.06 | 2.09 | 0.73 | 0.25 |
| 90 | 0.34 | 0.94 | 3.05 | 3.10 | 0.53 |

TABLE 8

Triamcinalone Release Results in Phosphate Buffered Saline pH 7.4 for 50% Drug Load

| | 755-50 | 752-50 | 504-50 | 502-50 | 755-50R |
|---|---|---|---|---|---|
| | Total release (%) | | | | |
| 1 | 1.83 | 2.01 | 1.88 | 1.97 | 2.20 |
| 4 | 2.93 | 2.32 | 2.56 | 2.57 | 3.75 |
| 7 | 3.68 | 2.44 | 2.74 | 2.84 | 4.62 |
| 14 | 4.66 | 2.58 | 2.93 | 3.09 | 5.68 |
| 21 | 5.23 | 2.73 | 3.16 | 3.46 | 6.21 |
| 28 | 5.60 | 2.87 | 4.29 | 4.23 | 6.62 |
| 35 | 5.75 | 2.98 | 6.37 | 4.92 | 6.84 |
| 48 | 5.92 | 3.70 | 8.07 | 7.44 | 7.04 |
| 69 | 7.69 | 5.35 | 14.47 | 10.79 | 7.84 |
| 90 | 9.42 | 7.38 | 39.38 | 33.66 | 8.59 |
| | Standard Deviation | | | | |
| 1 | 0.35 | 0.15 | 0.72 | 0.09 | 0.16 |
| 4 | 0.09 | 0.05 | 0.32 | 0.08 | 0.14 |
| 7 | 0.15 | 0.05 | 0.10 | 0.04 | 0.16 |
| 14 | 0.12 | 0.06 | 0.08 | 0.05 | 0.11 |
| 21 | 0.09 | 0.03 | 0.09 | 0.03 | 0.04 |
| 28 | 0.05 | 0.06 | 0.56 | 0.08 | 0.05 |
| 35 | 0.01 | 0.05 | 1.01 | 0.04 | 0.03 |
| 48 | 0.04 | 0.09 | 1.58 | 2.65 | 0.03 |
| 69 | 0.79 | 0.25 | 3.75 | 2.60 | 0.08 |
| 90 | 0.47 | 0.37 | 2.45 | 3.63 | 0.08 |

TABLE 9

Triamcinalone Release Results in Citrate Phosphate Buffer pH 5.4 for 30% Drug Load

| | 755-30 | 752-30 | 504-30 | 502-30 | 752-30R |
|---|---|---|---|---|---|
| | Total release (%) | | | | |
| 1 | 1.79 | 1.93 | 2.50 | 1.07 | 0.69 |
| 4 | 2.18 | 1.93 | 2.85 | 1.12 | 0.74 |
| 7 | 2.35 | 2.22 | 3.03 | 1.13 | 0.86 |
| 14 | 2.61 | 3.05 | 3.23 | 1.21 | 0.94 |
| 21 | 3.00 | 4.62 | 4.73 | 1.59 | 0.96 |
| 28 | 3.45 | 12.44 | 16.60 | 7.99 | 1.00 |
| 35 | 3.57 | 12.59 | 45.16 | 25.70 | 1.00 |
| 48 | 4.05 | 12.99 | 94.39 | 77.56 | 1.46 |
| 69 | 18.96 | 42.24 | 95.24 | 83.21 | 45.40 |
| 77 | 58.09 | 83.17 | | | 63.83 |
| 90 | 92.97 | 96.82 | | | 79.93 |
| | Standard Deviation | | | | |
| 1 | 0.19 | 1.11 | 0.12 | 0.05 | 0.05 |
| 4 | 0.03 | 0.00 | 0.02 | 0.04 | 0.03 |
| 7 | 0.06 | 0.26 | 0.04 | 0.02 | 0.01 |
| 14 | 0.05 | 1.18 | 0.02 | 0.03 | 0.03 |
| 21 | 0.21 | 2.06 | 0.04 | 0.02 | 0.02 |
| 28 | 0.27 | 3.92 | 0.27 | 0.64 | 0.03 |
| 35 | 0.07 | 0.06 | 2.99 | 2.69 | 0.00 |
| 48 | 0.27 | 0.04 | 3.90 | 2.92 | 0.04 |
| 69 | 0.48 | 3.20 | 0.50 | 3.24 | 2.29 |
| 77 | 2.48 | 6.49 | | | 2.71 |
| 90 | 3.88 | 5.73 | | | 4.08 |

TABLE 10

Triamcinalone Release Results in Citrate Phosphate Buffer pH 5.4 for 50% Drug Load

| | 755-50 | 752-50 | 504-50 | 502-50 | 755-50R |
|---|---|---|---|---|---|
| | Total release (%) | | | | |
| 1 | 4.32 | 3.14 | 4.10 | 3.10 | 5.63 |
| 4 | 7.96 | 3.38 | 5.77 | 4.08 | 9.39 |
| 7 | 13.26 | 3.46 | 6.24 | 4.42 | 11.52 |
| 14 | 16.75 | 3.60 | 6.79 | 4.77 | 14.79 |
| 21 | 19.60 | 3.80 | 10.34 | 5.25 | 16.43 |
| 28 | 21.91 | 3.90 | 20.94 | 9.17 | 17.21 |
| 35 | 23.75 | 4.02 | 41.21 | 16.58 | 17.59 |
| 48 | 24.50 | 5.02 | 82.11 | 71.13 | 18.38 |

TABLE 10-continued

Triamcinalone Release Results in Citrate Phosphate Buffer pH 5.4 for 50% Drug Load

|    | 755-50 | 752-50 | 504-50 | 502-50 | 755-50R |
|----|--------|--------|--------|--------|---------|
| 69 | 43.48  | 33.38  | 91.91  | 85.27  | 27.09   |
| 77 | 58.17  | 54.68  |        |        | 35.62   |
| 90 | 85.58  | 75.87  |        |        | 54.43   |
| Standard Deviation | | | | | |
| 1  | 1.01   | 0.63   | 0.14   | 0.14   | 1.76    |
| 4  | 0.76   | 0.09   | 0.36   | 0.08   | 0.09    |
| 7  | 5.93   | 0.05   | 0.17   | 0.03   | 0.07    |
| 14 | 1.16   | 0.03   | 0.13   | 0.03   | 0.15    |
| 21 | 1.23   | 0.03   | 0.32   | 0.03   | 0.12    |
| 28 | 2.78   | 0.02   | 0.14   | 0.55   | 0.11    |
| 35 | 2.20   | 0.03   | 1.66   | 3.08   | 0.06    |
| 48 | 0.34   | 0.19   | 3.58   | 13.62  | 0.10    |
| 69 | 8.47   | 7.52   | 4.47   | 1.67   | 1.65    |
| 77 | 1.78   | 7.97   |        |        | 1.13    |
| 90 | 5.86   | 11.33  |        |        | 4.57    |

The beclomethasone dipropionate release results are shown in Tables 11-14 are plotted in FIGS. 22 to 25, respectively.

In these experiments, beclomethasone dipropionate release was examined for about one month. In this early timeframe (e.g., within about 1 month), the release profiles for BD and TA were similar even though BD is about 150 times less soluble than TA. Changing to an acidic media increased the amount of released BD slightly but not as much as the same medium change did for TA. The BD release did not increase with increase drug load in the phosphate buffer, but did in the CTAB buffer. The response to increasing LG ratio was the same for both steroids for the first month. The effect is relatively small in the first 30 days but increasing the LG ratio decreases the amount of drug released. The effect of MW was different for the two steroids; triamcinalone's release increased slightly with higher MW in both media, whereas beclomethasone's release decreased in PBS and increased in CTAB with increasing MW.

TABLE 11

Beclomethasone Dipropionate Release Results in Phosphate Buffered Saline pH 7.4 for 30% Drug Load

|    | 755-30 | 752-30 | 504-30 | 502-30 | 752-30R |
|----|--------|--------|--------|--------|---------|
| Total release (%) | | | | | |
| 1  | 0.31   | 0.34   | 1.23   | 1.46   | 0.72    |
| 4  | 1.86   | 3.07   | 2.90   | 2.75   | 2.27    |
| 7  | 2.64   | 3.74   | 3.64   | 3.52   | 3.22    |
| 14 | 3.03   | 4.36   | 4.12   | 3.95   | 3.58    |
| 21 | 3.56   | 4.92   | 4.80   | 4.61   | 4.13    |
| 28 | 4.11   | 5.32   | 6.09   | 5.53   | 4.62    |
| 35 | 4.45   | 5.80   | 6.82   | 6.68   | 5.03    |
| 48 | | | | | |
| 69 | | | | | |
| 90 | | | | | |
| Standard Deviation | | | | | |
| 1  | 0.05   | 0.41   | 0.35   | 0.06   | 0.19    |
| 4  | 0.57   | 0.28   | 0.48   | 0.34   | 0.22    |
| 7  | 0.12   | 0.43   | 0.28   | 0.26   | 0.22    |
| 14 | 0.17   | 0.09   | 0.16   | 0.21   | 0.28    |
| 21 | 0.27   | 0.18   | 0.18   | 0.08   | 0.11    |
| 28 | 0.14   | 0.44   | 0.51   | 0.16   | 0.12    |
| 35 | 0.16   | 0.16   | 0.13   | 0.11   | 0.15    |
| 48 | | | | | |
| 69 | | | | | |
| 90 | | | | | |

TABLE 12

Beclomethasone Dipropionate Release Results in Phosphate Buffered Saline pH 7.4 for 50% Drug Load

|    | 755-50 | 752-50 | 504-50 | 502-50 | 755-50R |
|----|--------|--------|--------|--------|---------|
| Total release (%) | | | | | |
| 1  | 0.11   | 0.18   | 0.70   | 1.01   | 0.75    |
| 4  | 0.78   | 1.95   | 2.22   | 2.00   | 1.84    |
| 7  | 1.13   | 2.78   | 2.57   | 2.50   | 2.34    |
| 14 | 1.29   | 3.19   | 2.91   | 2.75   | 2.72    |
| 21 | 1.62   | 3.68   | 3.25   | 3.21   | 3.20    |
| 28 | 1.88   | 4.15   | 3.87   | 3.72   | 3.56    |
| 35 | 2.02   | 4.42   | 4.22   | 4.36   | 3.75    |
| 48 | | | | | |
| 69 | | | | | |
| 90 | | | | | |
| Standard Deviation | | | | | |
| 1  | 0.07   | 0.09   | 0.24   | 0.30   | 0.07    |
| 4  | 0.37   | 0.19   | 0.16   | 0.14   | 0.17    |
| 7  | 0.12   | 0.10   | 0.30   | 0.18   | 0.16    |
| 14 | 0.04   | 0.09   | 0.08   | 0.08   | 0.08    |
| 21 | 0.09   | 0.08   | 0.20   | 0.10   | 0.04    |
| 28 | 0.15   | 0.11   | 0.12   | 0.16   | 0.08    |
| 35 | 0.08   | 0.17   | 0.15   | 0.19   | 0.03    |
| 48 | | | | | |
| 69 | | | | | |
| 90 | | | | | |

TABLE 13

Beclomethasone Dipropionate Release Results in Citrate Phosphate Buffer pH 5.4 for 30% Drug Load

|    | 755-30 | 752-30 | 504-30 | 502-30 | 752-30R |
|----|--------|--------|--------|--------|---------|
| Total release (%) | | | | | |
| 1  | 0.28   | 1.20   | 2.16   | 1.28   | 1.37    |
| 4  | 1.44   | 1.54   | 3.16   | 1.59   | 1.50    |
| 7  | 2.15   | 1.87   | 3.90   | 2.04   | 1.93    |
| 14 | 2.62   | 2.06   | 4.53   | 2.39   | 2.27    |
| 21 | 3.05   | 2.35   | 7.45   | 3.68   | 2.54    |
| 28 | 3.32   | 2.50   | 12.51  | 7.09   | 2.82    |
| Standard Deviation | | | | | |
| 1  | 0.16   | 0.22   | 0.23   | 0.25   | 0.10    |
| 4  | 0.24   | 0.11   | 0.22   | 0.16   | 0.11    |
| 7  | 0.15   | 0.09   | 0.17   | 0.03   | 0.08    |
| 14 | 0.09   | 0.21   | 0.08   | 0.11   | 0.06    |
| 21 | 0.09   | 0.05   | 0.24   | 0.16   | 0.16    |
| 28 | 0.10   | 0.22   | 0.74   | 0.29   | 0.07    |

TABLE 14

Beclomethasone Dipropionate Release Results in Citrate Phosphate Buffer pH 5.4 for 50% Drug Load

|    | 755-50 | 752-50 | 504-50 | 502-50 | 755-50R |
|----|--------|--------|--------|--------|---------|
| Total release (%) | | | | | |
| 1  | 2.01   | 0.47   | 3.07   | 2.16   | 3.80    |
| 4  | 6.26   | 1.77   | 6.01   | 3.16   | 7.64    |
| 7  | 9.00   | 2.55   | 7.48   | 3.98   | 10.30   |
| 14 | 12.40  | 3.51   | 8.45   | 4.73   | 13.49   |
| 21 | 14.16  | 4.06   | 10.59  | 6.04   | 15.06   |
| 28 | 15.07  | 4.44   | 15.31  | 9.21   | 15.95   |
| Standard Deviation | | | | | |
| 1  | 0.36   | 0.06   | 0.74   | 0.37   | 0.42    |
| 4  | 0.63   | 0.24   | 0.51   | 0.27   | 0.61    |
| 7  | 0.54   | 0.18   | 0.17   | 0.16   | 0.58    |
| 14 | 0.49   | 0.66   | 0.15   | 0.18   | 0.65    |

TABLE 14-continued

Beclomethasone Dipropionate Release Results in Citrate
Phosphate Buffer pH 5.4 for 50% Drug Load

|    | 755-50 | 752-50 | 504-50 | 502-50 | 755-50R |
|----|--------|--------|--------|--------|---------|
| 21 | 0.26   | 0.15   | 0.28   | 0.12   | 0.22    |
| 28 | 0.13   | 0.12   | 0.79   | 0.29   | 0.08    |

Based on these results, the release of low water soluble steroids from PLGA implants is primarily limited by the dissolution of the steroid in the first thirty days, and not the loading or amount of the steroid, or the polymer matrix properties. In the early part of the dissolution (e.g., during the first portion of the drug release profile), the release rates of the two steroids are very similar even though their solubilities are quite different. During this period the drug release rate appears to be controlled by the steroid dissolution with the polymer properties having a minor effect. Later in the dissolution (e.g., during a second portion of the drug release profile), the steroid release is more dependent on polymer properties as the hydrolysis rates of the polymers become more important. Changing to a lower pH media with a lower surface tension increases the amount released for both steroids.

Example 10

Treatment of Uveitis with an Intraocular Implant
Comprising Fluocinolone and Timolol Although the patient of Example 5 experiences relief from the symptoms of uvetitis with the implant containing fluocinololone acetonide, the intraocular pressure in the eye of the patient increases with time.

An implant containing 250 µg of fluocinolone acetonide, 250 µg of a combination of biodegradable polymers (R502H and R202H in a 1:2 ratio) and 500 µg of timolol, an antiglaucoma drug, is substituted for the implant of Example 5 that contains fluocinololone acetonide without an antiglaucoma drug. The patient experiences relief from the symptoms of uvetitis, and the intraocular pressure of the patient remains within acceptable limits. The implant comprising a steroid and an antiglaucoma drug, timolol, provides relief from the symptoms of uvetitis while maintaining acceptable intraocular pressure over extended periods of time.

Example 11

Treatment of Macular Edema with a First Intraocular
Implant Comprising Fluocinolone and a Second
Intraocular Implant Comprising Timolol Although the patient of Example 7 experiences a decrease in pain and improvement in vision after implantation of the implant containing fluocinolone acetonide and PLGA, the intraocular pressure in the eye of the patient increases over time.

A second implant containing 1 mg of timolol and 250 µg of combination of biodegradable polymers (R502H and R202H in a 1:2 ratio) is implanted in the eye of the patient. The intraocular pressure of the patient decreases, and the patient continues to have improvement in vision and decrease in pain.

Example 12

Treatment of Uveitis with an Intraocular Implant
Comprising Alternating Layers of Fluocinolone and
Timolol A 56 year old male presents with posterior uveitis. An implant containing alternating layers of fluocinololone acetonide and brimonidine is formed, where the implant contains a total of 250 µg of flucinololone associated with 250 µg of a combination of biodegradable polymers (R502H and R202H in a 1:2 ratio) and 500 µg of timolol associated with 500 µg of PLGA.

The implant is injected into the vitreous of each of the patient's eyes using a syringe with a needle. The patient reports improvement in vision, and the intraocular pressure remains within acceptable limits.

Example 13

Treatment of Anterior Uveitis with an Intraocular
Implant Comprising Dexamethasone and a Second
Implant Comprising Timolol Uveitis, a term originally coined to describe inflammation of the uveal tract (iris, ciliary body, choroid, the middle layer of the eye), comprises a group of diverse disease affecting not only the uvea, but also the retinal, optic nerve and vitreous. The current International Uveitits Study Group classification separates uveitis by anatomical location of the disease according to the major visible signs. One of the most common forms of uveitis is anterior uveitis, which affects the area of the iris (irititis), cilary body (cyclitis) and aqueous humor. Uveitis can also be classified by its duration as acute or chronic (more than three months in duration) and recurrent. The causes of uveitis are diverse and include infection (viral, parasitic, fungal and bacterial), traumatic injury to the eye, and systemic or local autoimmune diseases, although most cases are idiopathic.

Although the topical administration of steroids is the current mainstay of therapy for anterior uveitis, a periocular injection of steroids may also be added in the patient is not responding adequately or in the disease is severe. Additionally, oral corticosteroids may be given if topical administration is ineffective.

Adverse effects from topical steroid use include elevated IOP, optic nerve damage, and cataract formation or progression. Additional risks from periocular injection include globe rupture, fibrosis of the extraocular muscles, and ptosis (eyelid droop) with repeated injections. Systemic absorption from depot periocular administration does occur as well. Side effects of systemic steroid treatment include hypertension, hyperglycemia, gastrointestinal hemorrhage, osteoporosis, and psychosis.

A 52 year old female presents with persistent, non-infectious posterior uveitis in the right eye. Following diagnosis, the patient is given ophthalmic gatifloxacin at an antibacterial concentration, and told to instill a drop on the right eye 4 times a day (QID) for 3 days. On the third day, the patient is administered a first biodegradable polymeric implant containing 700 µg of micronized dexamethasone in a 60:40 weight ration of drug to polymer. The polymer portion of the implant comprises a combination of biodegradable polymers (R502H and R202H in a 1:2 ratio).

At the same time, the patient is also co-administered a first biodegradable polymeric implant containing 700 µg of micronized brimonidine tartrate in a 60:40 weight ration of drug to polymer (R502H and R202H in a 1:2 ratio). The second biodegradable polymeric implant is associated with a polymer coating that is impermeable to the vitreous and containing a plurality of holes, drilled through the polymer coating with a laser, to allow the brimonidine to permeate into the vitreous.

Both implants are simultaneously injected into the eye of the female patient by intracameral injection through the pars plana using an applicator system comprising a 22 gauge needle.

The patient is then monitored weekly for six weeks following implantation of the dexamethasone and brimonidine implants. At each monitoring visit the patient's right eye is carefully examined for signs or abnormalities; the features observed include the eyelid, conjunctiva, cornea, anterior chamber, iris color, lens status, vitreous cells, and retina, including macula, and the optic nerve. The patient's intraocular pressure is also monitored.

At the end of the six week period, the patient has improved vision compared to her situation prior to the insertion of the implants, and the inflammation associated with the uveal tract is absent. The intraocular pressure in the eye of the patient remains within normal levels; no significant increase in degeneration of the retina or optic nerve is seen during the treatment regimen.

Example 14

Treatment of Anterior Uveitis with an Intraocular Implant Comprising Alternating Layers of Dexamethasone and Timolol Intermediate uveitis is characterized by inflammation of the middle of the eye, including the vitreous and peripheral retina. Pars planitis is considered a subset of intermediate uveitis and is characterized by the presence of "snowbanking" over the pars plana and ora serrata. Some ophthalmologists believe that patients with pars planitis have a more severe disease, for example with more macular edema, than other patients with intermediate uveitis.

Vision loss associated with intermediate uveitis is usually due to cystoid macular edema, inflammatory vitreal haze and debris, and cataract. The former two conditions are usually responsive to treatment with anti-inflammatory agents, including anti-inflammatory steroids.

A 56 year old male presents with intermediate uveitis in both eyes, in each case showing involvement of the vitreous (vitreal haze). Following diagnosis, the patient is given ophthalmic gatifloxacin at an antibacterial concentration, and told to instill a drop on the right eye 4 times a day (QID) for 3 days. On the third day, the patient is administered a biodegradable polymeric implant containing 500 µg of micronized dexamethasone and 500 µg brimonidine in a 60:40 weight ration of drug to polymer, and comprising interleaved alternative layers of drug. The polymer portion of the implant comprises a combination of biodegradable polymers (R502H and R202H in a 1:2 ratio).

The implant is injected through the pars plana into the vitreous of each of the patient's eyes using an applicator with a 22 gauge needle. The patient is monitored weekly for six weeks following administration of the implant. The primary indication of efficacy is clearing of vitreal haze, giving rise to increased visual acuity.

At the end of the six-week monitoring period the patient reports improvement in vision, and tests an improvement of 3 lines in visual acuity. Observation shows no trace of vitreal haze remaining, and the intraocular pressure remains within acceptable limits.

The present invention also encompasses the use of any and all possible combinations of the therapeutic agents disclosed herein in the manufacture of a medicament, such as a drug delivery system or composition comprising such a drug delivery system, to treat one or more ocular conditions, including those identified above.

All references, articles, publications and patents and patent applications cited herein are incorporated by reference in their entireties.

While this invention has been described with respect to various specific examples and embodiments, it is to be understood that the invention is not limited thereto and that it can be variously practiced within the scope of the following claims.

We claim:

1. A biodegradable intraocular implant, comprising:
   a steroid; and
   an auxiliary agent, wherein the steroid and the auxiliary agent are associated with a biodegradable polymer in the form of an intraocular implant.

2. The implant of claim 1, wherein the steroid is selected from the group consisting of dexamethasone, fluocinolone, fluocinolone acetonide, triamcinolone, triamcinolone acetonide, salts thereof, and mixtures thereof.

3. The implant of claim 1, wherein the biodegradable polymer is a poly (lactide-co-glycolide) polymer.

4. The implant of claim 1, wherein the auxiliary agent is selected from the group consisting of a parasympathomimetic, a sympathomimetic, an alpha agonist, a beta blocker, a carbonic anhydrase inhibitor, a prostaglandin analog, a neuroprotectant, and mixtures thereof.

5. The implant of claim 1, wherein the auxiliary agent is selected from the group consisting of pilocarpine, carbachol, echothiophate, epinephrine, dipivefrin, apraclonidine, brimonidine, clonidine, apraclonidine, p-aminoclonidine, oxymetazoline, epinephrine, norepinephrine, cirazoline, dexmedetomidine, mivazerol, xylazine, medetomidine, memantine, timolol, levobunolol, metipranolol, carteolol, betaxolol, dorzolamine, brinzolamide, dichlorphenamide, latanoprost, bimatoprost, travoprost, unoprostone, and mixtures thereof.

6. The implant of claim 1, wherein the implant comprises a polymeric outer layer which is impermeable to an intraocular fluid.

7. The implant of claim 6, wherein the outer layer comprises a plurality of openings or holes in the polymeric outer layer.

8. A biodegradable intraocular implant system, comprising:
   a steroid associated with a biodegradable polymer in the form of a first intraocular implant; and
   an auxiliary agent associated with a biodegradable polymer in the form of a second intraocular implant.

9. A biodegradable intraocular implant system, comprising:
   a steroid associated with a biodegradable polymeric component in the form of an intraocular implant structured for intravitreal placement in an eye of an individual, the steroid being present in an amount effective in treating an ocular condition of the eye with a reduced toxicity relative to intravitreal injection of a liquid composition containing the same steroid; and
   an auxiliary agent associated with a biodegradable polymeric component in the form of an intraocular implant structured for intravitreal placement in an eye of an individual, the auxiliary agent being present in an amount effective to reduce the occurrence of at least one side effect present upon otherwise identical administration of the steroid alone.

10. The implant system of claim 9, wherein the steroid is selected from the group consisting of dexamethasone, fluocinolone, fluocinolone acetonide, triamcinolone, triamcinolone acetonide, salts thereof, and mixtures thereof.

11. The implant system of claim 9, wherein the auxiliary agent comprises an antiglaucoma drug selected from the group consisting of a parasympathomimetic, a sympathomimetic, an alpha agonist, a beta blocker, a carbonic anhydrase inhibitor, a prostaglandin analog, a neuroprotectant, and mixtures thereof.

12. The implant system of claim 9, wherein the implant comprises steroid and auxiliary agent in alternating layers.

13. The implant system of claim 9, wherein the steroid and the auxiliary agent are comprised in the same implant.

14. The implant system of claim 9, wherein the steroid and the auxiliary agent are released from the implant at different times.

15. The implant system of claim 9, wherein the steroid and the auxiliary agent are released from the implant intermittently.

* * * * *

UNITED STATES PATENT AND TRADEMARK OFFICE
CERTIFICATE OF CORRECTION

PATENT NO. : 8,147,865 B2
APPLICATION NO. : 11/474149
DATED : April 3, 2012
INVENTOR(S) : Glenn T. Huang et al.

It is certified that error appears in the above-identified patent and that said Letters Patent is hereby corrected as shown below:

On the first page, in field (56), under "Other Publications", in column 2, line 2, delete "Oththalmology," and insert -- Ophthalmology, --, therefor.

On page 4, in column 1, under "Other Publications", line 3, delete "triaminolone" and insert -- triamcinolone --, therefor.

On page 4, in column 1, under "Other Publications", line 7, delete "Afymetrix" and insert -- Affymetrix --, therefor.

On page 4, in column 1, under "Other Publications", line 16, delete "Ophthalmololgy," and insert -- Ophthalmology, --, therefor.

On page 4, in column 1, under "Other Publications", line 52, delete "5-Fluorouacil"," and insert -- 5-Fluorouracil", --, therefor.

On page 4, in column 2, under "Other Publications", line 45, delete "Ophtalmol," and insert -- Ophthalmol, --, therefor.

On page 4, in column 2, under "Other Publications", line 55, delete "2-methoxyoestradiol" and insert -- 2-methoxyestradiol --, therefor.

On page 4, in column 2, under "Other Publications", line 63, delete "Dermotol.," and insert -- Dermatol., --, therefor.

On page 4, in column 2, under "Other Publications", line 70, delete "BiodegadablePolymers" and insert -- Biodegradable Polymers --, therefor.

On page 5, in column 1, under "Other Publications", line 10, delete ""Polyactic" and insert -- "Polylactic --, therefor.

Signed and Sealed this
Third Day of July, 2012

David J. Kappos
*Director of the United States Patent and Trademark Office*

CERTIFICATE OF CORRECTION (continued)
U.S. Pat. No. 8,147,865 B2

On page 5, in column 1, under "Other Publications", line 11, delete "Steriods"" and insert -- Steroids" --, therefor.

In column 36, line 13, delete "96RPM" and insert -- 96 RPM --, therefor.

In column 42, line 55, delete "poly (lactide" and insert -- poly(lactide --, therefor.

In column 42, line 60, delete "triamcinalone" and insert -- triamcinolone --, therefor.

In column 42, line 62, delete "poly (D,L-lactide" and insert -- poly(D,L-lactide --, therefor.

In column 42, line 63, delete "triamcinalone" and insert -- triamcinolone --, therefor.

In column 43, line 4, delete "cetytrimethylammonium" and insert -- cetyltrimethylammonium --, therefor.

In column 43, line 9, delete "Triamcinalone" and insert -- Triamcinolone --, therefor.

In column 43, line 16, delete "triamcinalone" and insert -- triamcinolone --, therefor.

In column 43, line 26, delete "Triamcinalone" and insert -- Triamcinolone --, therefor.

In column 43, line 27, delete "Beclamethasone" and insert -- Beclomethasone --, therefor.

In column 43, line 66, delete "triamcinalone" and insert -- triamcinolone --, therefor.

In column 43, lines 66-67, delete "beclamethasone" and insert -- beclomethasone --, therefor.

In column 44, in TABLE 5, line 1, delete "Triamcinalone" and insert -- Triamcinolone --, therefor.

In column 44, line 47, delete "Triamcinalone" and insert -- Triamcinolone --, therefor.

In column 44, line 56, delete "triamcinalone" and insert -- triamcinolone --, therefor.

In column 45, line 1, delete "triamcinalone" and insert -- triamcinolone --, therefor.

In column 45, in TABLE 7, line 1, delete "Triamcinalone" and insert -- Triamcinolone --, therefor.

In column 45, In TABLE 8, line 1, delete "Triamcinalone" and insert -- Triamcinolone --, therefor.

In column 46, in TABLE 8-continued, line 1, delete "Triamcinalone" and insert -- Triamcinolone --, therefor.

In column 46, in TABLE 9, line 1, delete "Triamcinalone" and insert -- Triamcinolone --, therefor.

CERTIFICATE OF CORRECTION (continued)

In column 46, in TABLE 10, line 1, delete "Triamcinalone" and insert -- Triamcinolone --, therefor.

In column 47, in TABLE 10-continued, line 1, delete "Triamcinalone" and insert -- Triamcinolone --, therefor.

In column 47, line 22, delete "are" and insert -- and are --, therefor.

In column 47, line 36, delete "triamcinalone's" and insert -- triamcinolone's --, therefor.

In column 49, line 30, delete "uvetitis" and insert -- uveitis --, therefor.

In column 49, lines 30-31, delete "fluocinololone" and insert -- fluocinolone --, therefor.

In column 49, line 37, delete "fluocinololone" and insert -- fluocinolone --, therefor.

In column 49, line 39, delete "uvetitis," and insert -- uveitis, --, therefor.

In column 49, line 42, delete "uvetitis" and insert -- uveitis --, therefor.

In column 49, line 67, delete "flucinololone" and insert -- fluocinolone --, therefor.

In column 50, line 2, delete "flucinololone" and insert -- fluocinolone --, therefor.

In column 50, line 22, delete "Uveitits" and insert -- Uveitis --, therefor.

In column 50, line 26, delete "(irititis), cilary" and insert -- (iritis), ciliary --, therefor.

In column 52, line 22, in claim 3, delete "poly (lactide" and insert -- poly(lactide --, therefor.